US012586181B2

(12) United States Patent
Lee et al.

(10) Patent No.: US 12,586,181 B2
(45) Date of Patent: Mar. 24, 2026

(54) FUNCTIONAL IMAGING FEATURES FROM COMPUTED TOMOGRAPHY IMAGES

(71) Applicant: Oxford University Innovation Limited, Oxford (GB)

(72) Inventors: Regent Lee, Oxford (GB); Anirudh Chandrashekar, Oxford (GB); Vicente Grau, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 617 days.

(21) Appl. No.: 17/924,382

(22) PCT Filed: May 12, 2021

(86) PCT No.: PCT/GB2021/051141
§ 371 (c)(1),
(2) Date: Nov. 10, 2022

(87) PCT Pub. No.: WO2021/229223
PCT Pub. Date: Nov. 18, 2021

(65) Prior Publication Data
US 2024/0242338 A1     Jul. 18, 2024

(30) Foreign Application Priority Data
May 15, 2020    (GB) ..................................... 2007256

(51) Int. Cl.
| | |
|---|---|
| *G06T 7/00* | (2017.01) |
| *G06T 7/11* | (2017.01) |
| *G06V 20/69* | (2022.01) |
| *G16H 50/20* | (2018.01) |

(52) U.S. Cl.
CPC .............. *G06T 7/0012* (2013.01); *G06T 7/11* (2017.01); *G06V 20/698* (2022.01); *G16H 50/20* (2018.01);
(Continued)

(58) Field of Classification Search
USPC .......................................................... 382/128
See application file for complete search history.

(56) References Cited

U.S. PATENT DOCUMENTS

| | | | | | |
|---|---|---|---|---|---|
| 2012/0003160 | A1* | 1/2012 | Wolf | ........................ | B82Y 5/00 424/9.3 |
| 2014/0249408 | A1* | 9/2014 | Collins | .................. | A61B 6/032 600/407 |

(Continued)

FOREIGN PATENT DOCUMENTS

EP          3 460 751 A1     3/2019

OTHER PUBLICATIONS

International Search Report and Written Opinion for WO 2021/229223 (PCT/GB2021/051141), dated Aug. 16, 2021, pp. 1-10.
(Continued)

*Primary Examiner* — Darryl V Dottin
(74) *Attorney, Agent, or Firm* — Thomas|Horstemeyer, LLP

(57) ABSTRACT

Methods, apparatus and computer readable media are provided for identifying functional features from a computed tomography (CT) image. The CT image may be a contrast-enhanced CT image or a non-contrast CT image. According to some examples, methods, apparatus and computer readable media are also provided for using machine learning to identify functional features from CT images. According to some examples, simulated functional image datasets such as simulated PET images or simulated SUV images are generated from a received CT image.

19 Claims, 50 Drawing Sheets

Specification includes a Sequence Listing.

(52) U.S. Cl.
CPC .............. *G06T 2207/10081* (2013.01); *G06T 2207/10104* (2013.01); *G06T 2207/20084* (2013.01); *G06T 2207/30096* (2013.01)

(56) References Cited

U.S. PATENT DOCUMENTS

| | | | |
|---|---|---|---|
| 2017/0337681 A1 | 11/2017 | Lure et al. | |
| 2019/0333219 A1* | 10/2019 | Xu ....................... | G06N 3/0464 |
| 2019/0357870 A1 | 11/2019 | Madabhushi et al. | |
| 2020/0104995 A1* | 4/2020 | Akahori ................... | G06T 7/11 |
| 2020/0254037 A1* | 8/2020 | Gansert ............. | C07K 16/2827 |

OTHER PUBLICATIONS

UK Search Report for GB 2007256.7, dated Oct. 12, 2020, pp. 1-4.
Avi Ben-Cohen et al: "Virtual PET Images from CT Data Using Deep Convolutional Networks: Initial Results", Arxiv .Org, Cornell University Li Bra Ry, 201 Olin Library Cornell University Ithaca, NY 14853, Jul. 30, 2017 (Jul. 30, 2017).
Martin Vallieres et al.: "Radiomics strategies for risk assessment of tumour failure in head-and-neck cancer", arxiv.org, Cornell University Library, 201 Olin Library Cornell University Ithaca, NY 14853, Mar. 24, 2017 (Mar. 24, 2017).
Vallieres Martin et al: "Supplementary Information Radiomics strategies for risk assessment of tumour failure in head and neck cancer", Jul. 10, 2017 (Jul. 10, 2017), pp. 1-41.
International Preliminary Report on Patentability for WO 2021/229223 (PCT/GB2021/051141), dated Nov. 15, 2022, pp. 1-8.

* cited by examiner

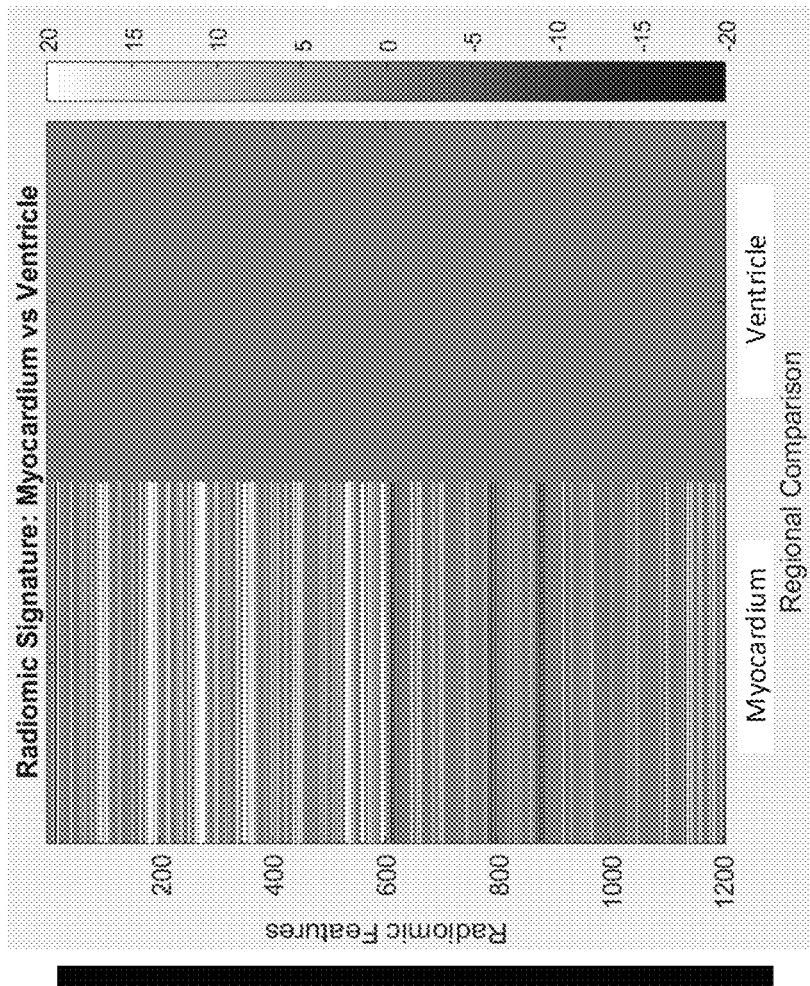
*FIG. 4A*
*FIG. 4B*

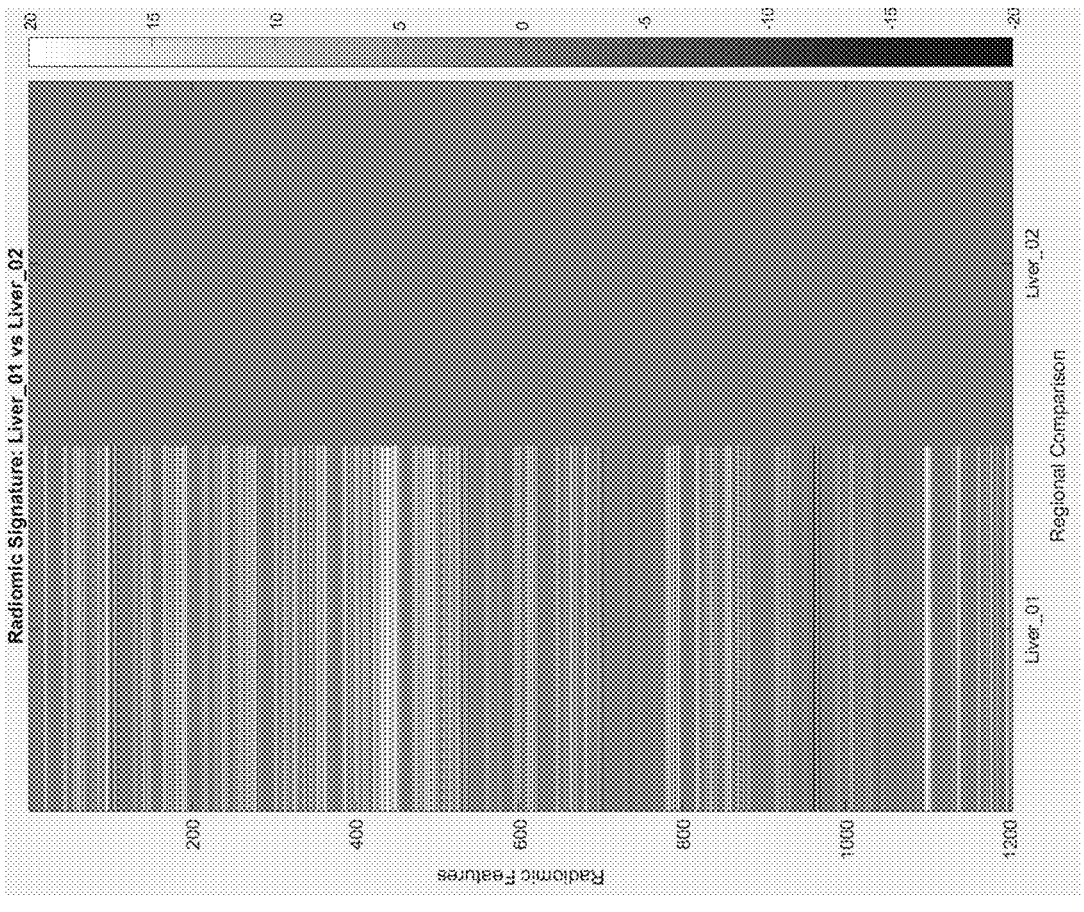
*FIG. 8B*
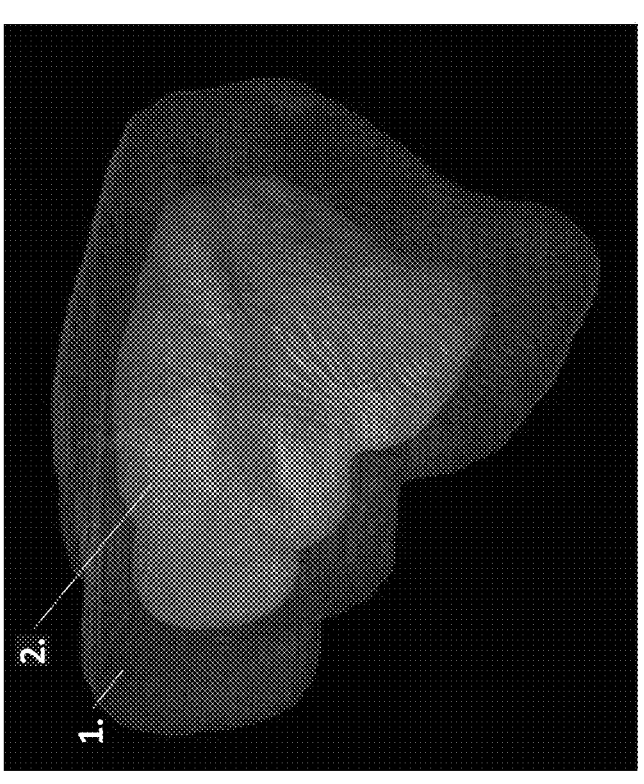
*FIG. 8A*

*FIG. 9A*
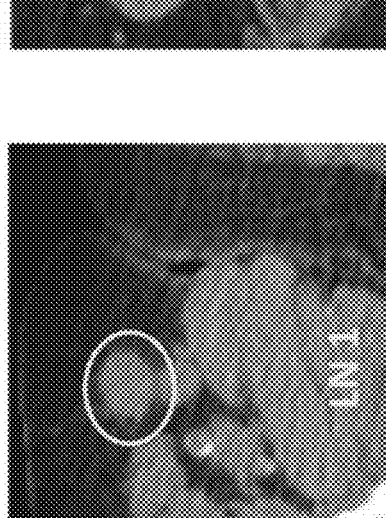
*FIG. 9B*
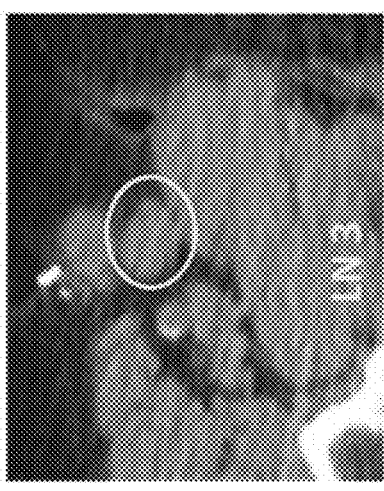
*FIG. 9C*
Lymph Nodes Positive for FDG uptake
*FIG. 9D*
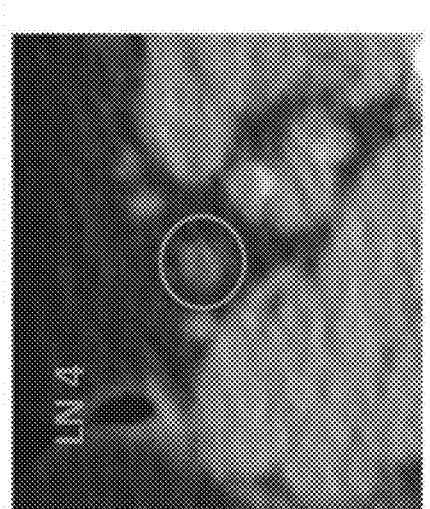
*FIG. 9E*
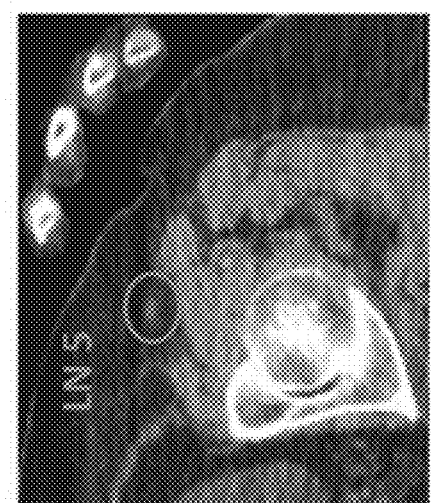
*FIG. 9F*
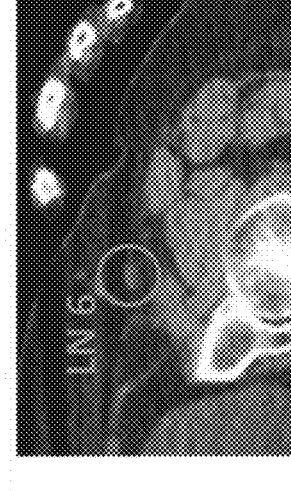
Lymph Nodes Negative for FDG uptake

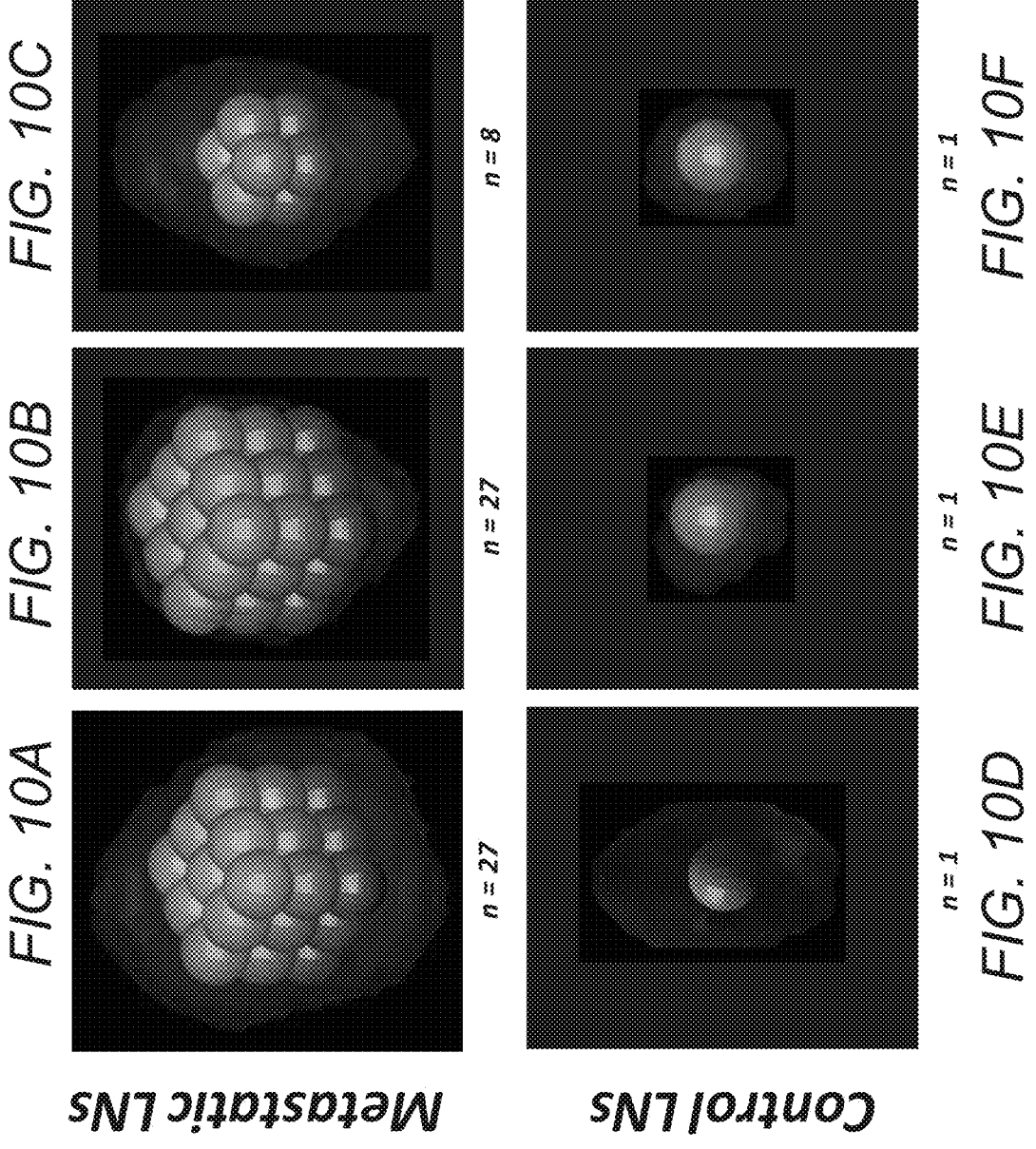

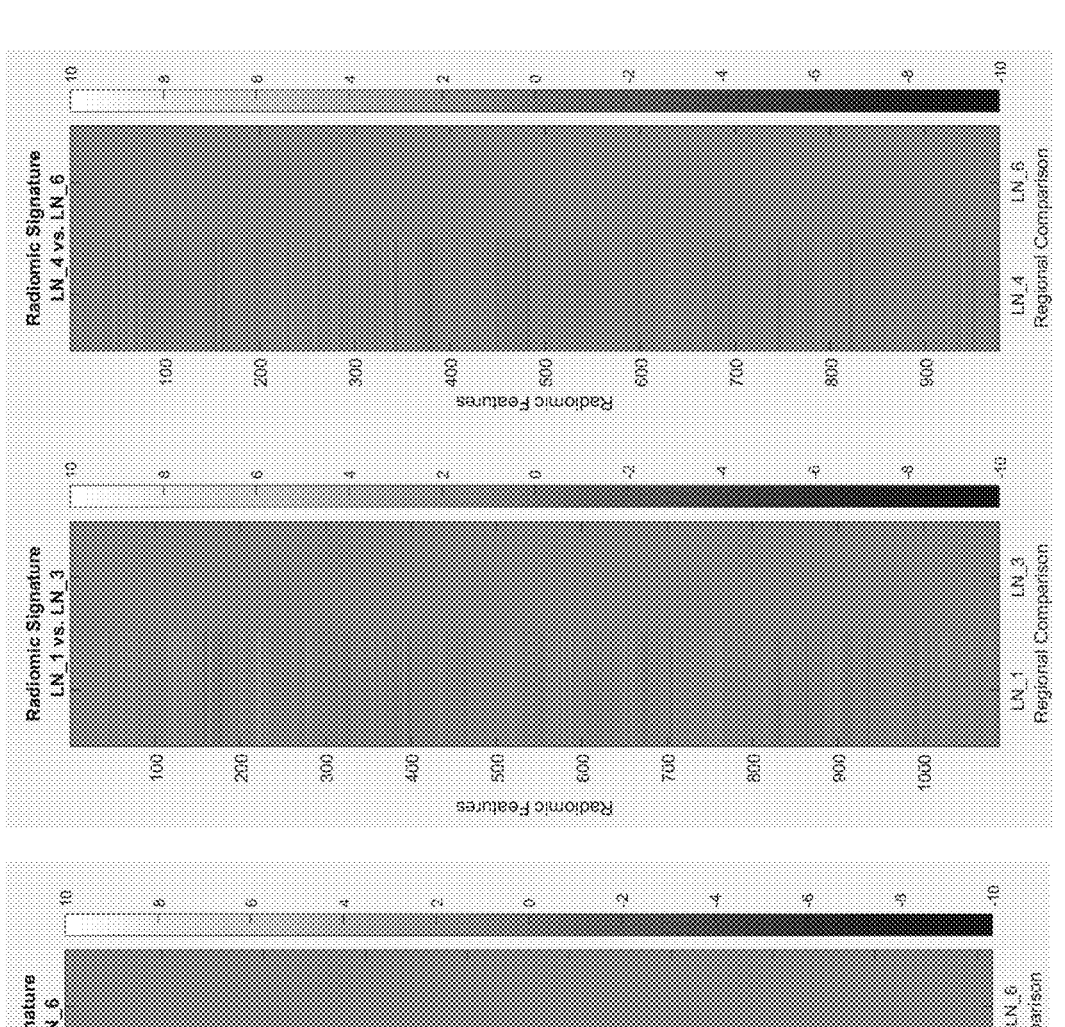
*FIG. 12B*
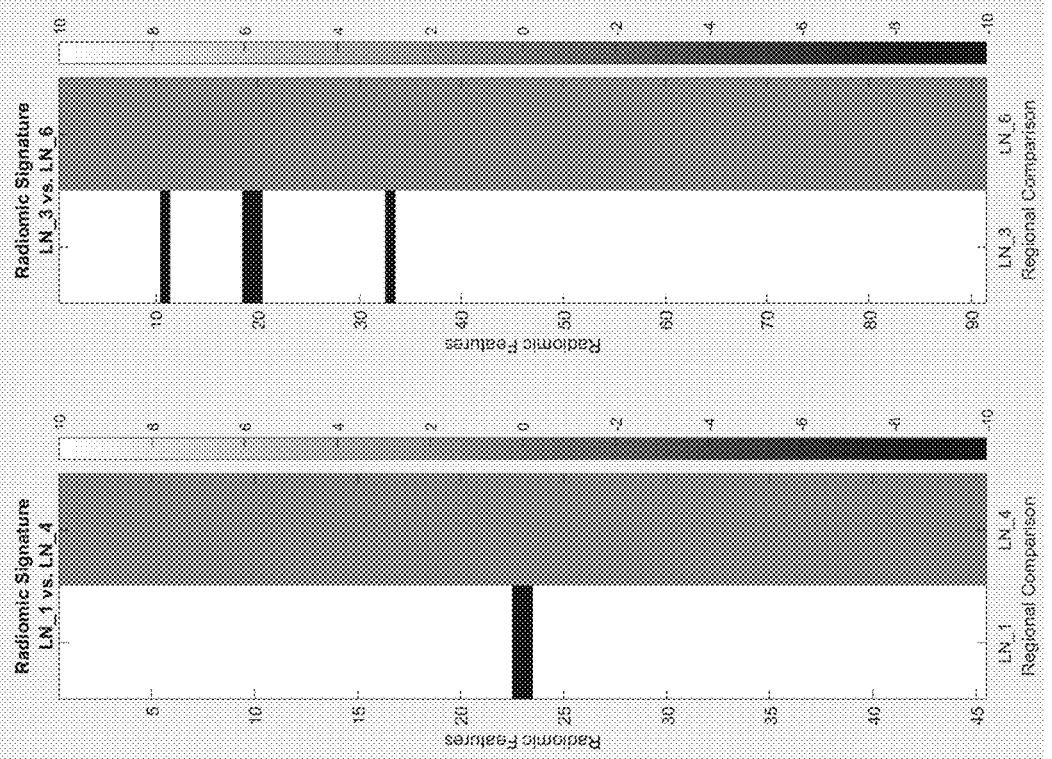
*FIG. 12A*

| | Radiomics Features (n=6) |
|---|---|
| 1 | wavelet-HHL_glszm_SmallAreaEmphasis |
| 2 | wavelet-HHL_glszm_SmallAreaLowGrayLevelEmphasis |
| 3 | wavelet-LHH_glszm_SmallAreaEmphasis |
| 4 | wavelet-LHH_glszm_SmallAreaHighGrayLevelEmphasis |
| 5 | wavelet-LHH_glszm_SmallAreaLowGrayLevelEmphasis |
| 6 | wavelet-LLH_glszm_SmallAreaHighGrayLevelEmphasis |

FIG. 15

Lymph Node 1

Non-contrast CT

FDG-PET
(Ground Truth)

Simulated PET

Lymph Node 2
Simulated PET
*FIG. 18C*
FDG-PET
(Ground Truth)
*FIG. 18B*
Non-contrast CT
*FIG. 18A*

Lymph Node 3

Non-contrast CT

FDG-PET
(Ground Truth)

Simulated PET

Lymph Node 4
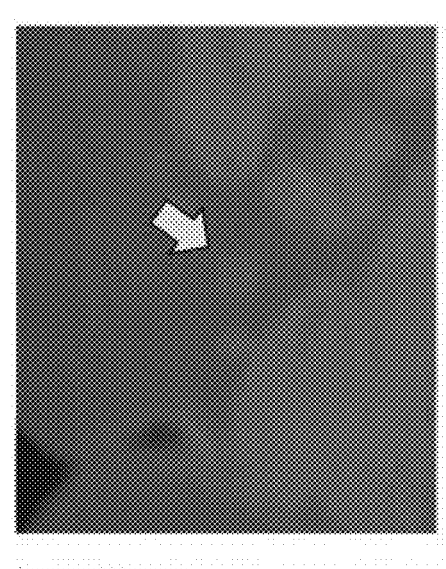
Simulated PET
*FIG. 20C*
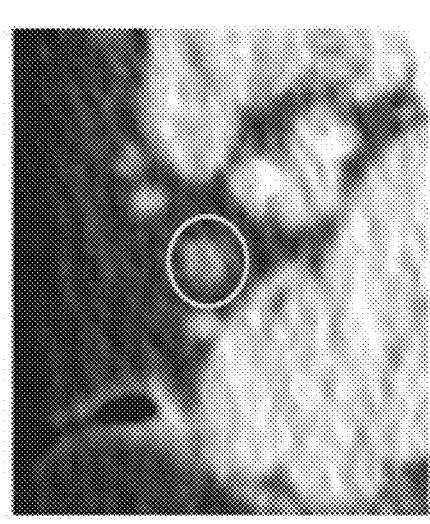
FDG-PET
(Ground Truth)
*FIG. 20B*
Non-contrast CT
*FIG. 20A*

Lymph Node 5
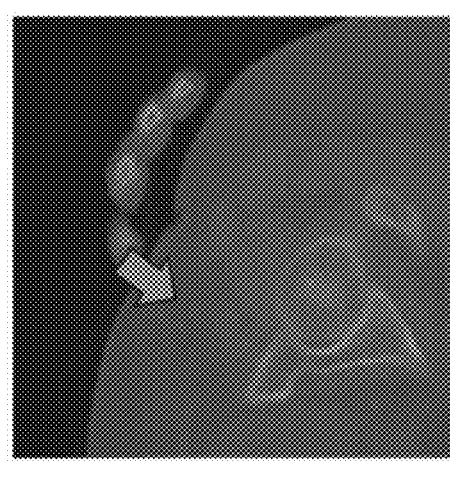
Simulated PET
*FIG. 21C*
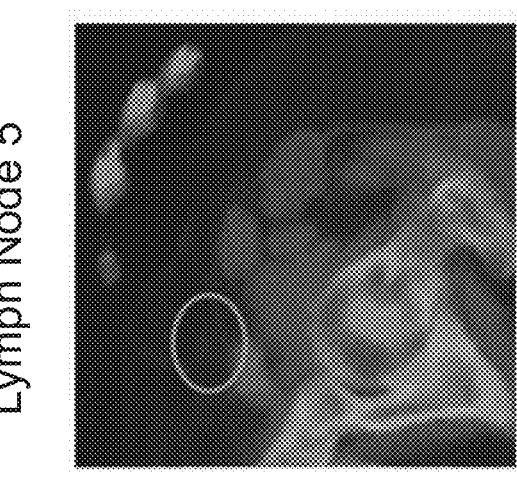
FDG-PET
(Ground Truth)
*FIG. 21B*
Non-contrast CT
*FIG. 21A*

Lymph Node 6
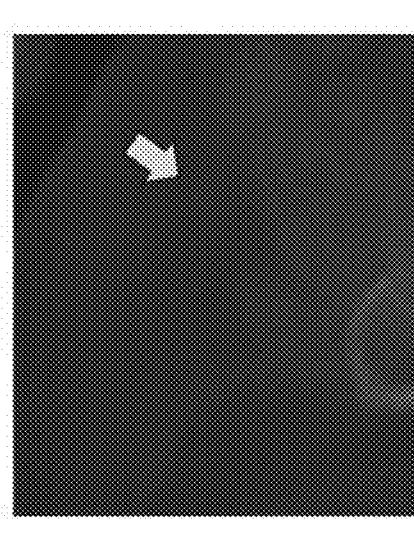
Simulated PET
*FIG. 22C*
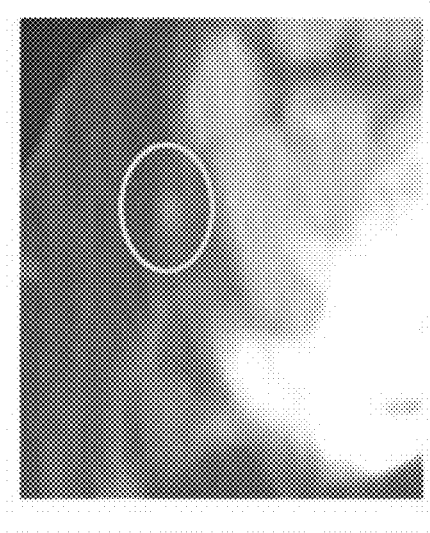
FDG-PET
(Ground Truth)
*FIG. 22B*
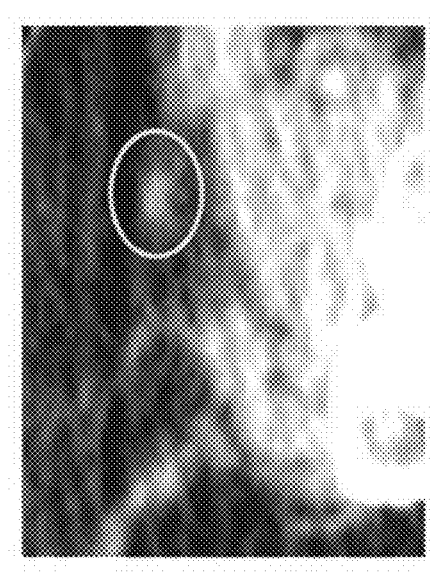
Non-contrast CT
*FIG. 22A*

Non-Contrast
CT (NCT)

SUV Map
(Inverted)

Overlayed

Receive a plurality of CT images, each showing a target region of a subject          3810

Receive a plurality of functional image datasets indicating functional features in a target region represented in one or more CT images          3820

Map each functional dataset to the one or more CT images          3830

Generate a functional feature identifier for each CT image          3840

FIG. 39

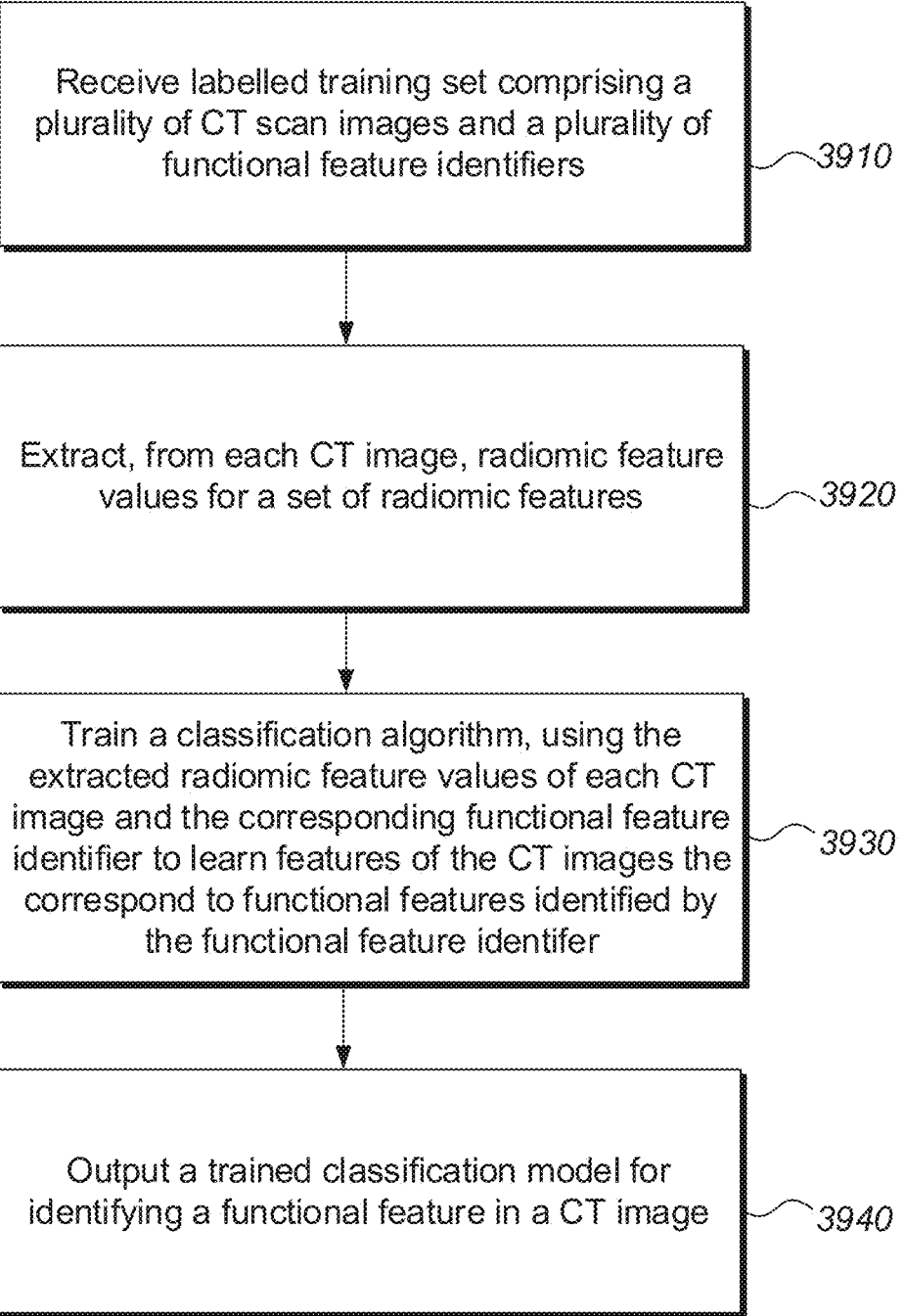

Receive labelled training set comprising a plurality of CT scan images and a plurality of functional feature identifiers          3910

Extract, from each CT image, radiomic feature values for a set of radiomic features          3920

Train a classification algorithm, using the extracted radiomic feature values of each CT image and the corresponding functional feature identifier to learn features of the CT images the correspond to functional features identified by the functional feature identifer          3930

Output a trained classification model for identifying a functional feature in a CT image          3940

FIG. 40

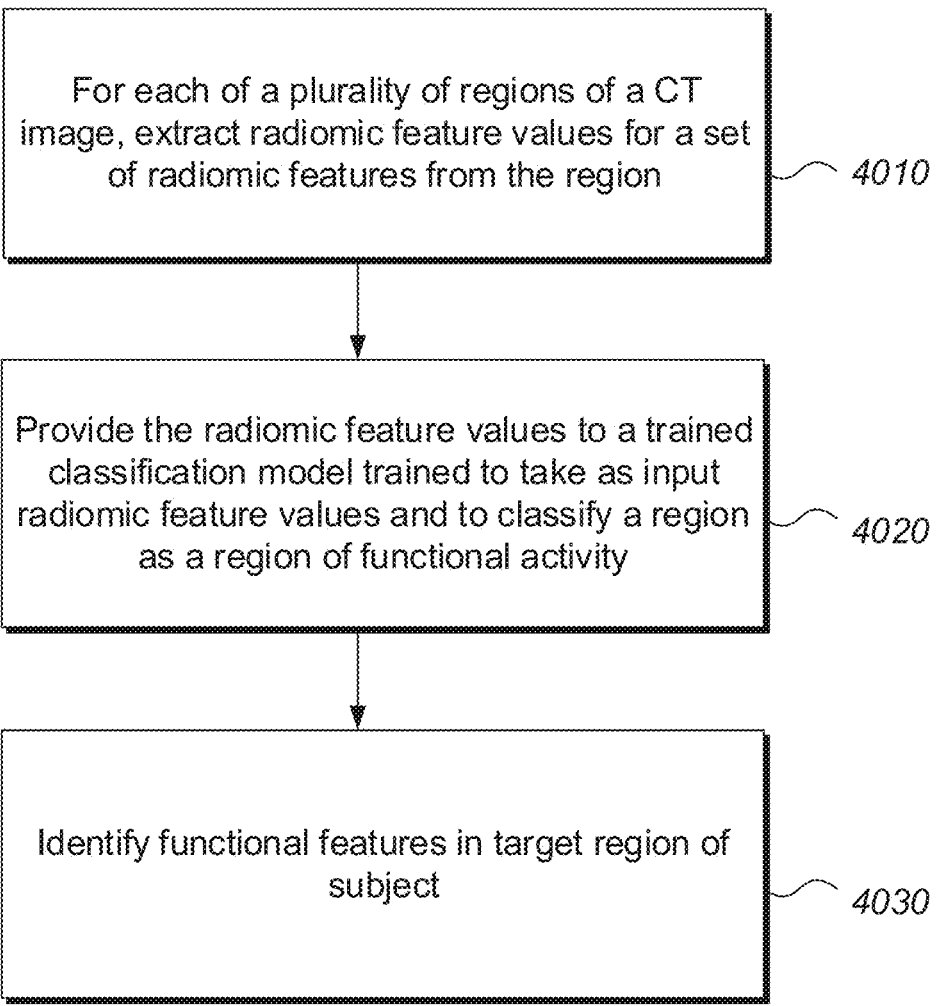

For each of a plurality of regions of a CT image, extract radiomic feature values for a set of radiomic features from the region — 4010

Provide the radiomic feature values to a trained classification model trained to take as input radiomic feature values and to classify a region as a region of functional activity — 4020

Identify functional features in target region of subject — 4030

Receive a training set comprising a plurality of CT images and a plurality of functional image datasets     ~4210

Train a Generative Adversarial Network     ~4220

Output a trained generator model     ~4230

Provide a CT image to a trained generator model — 4310

Generate a visualisation identifying functional features and structural features in the CT image — 4320

SEQUENCE LISTING

```
<160> NUMBER OF SEQ ID NOS: 41

<210> SEQ ID NO 1
<211> LENGTH: 188
<212> TYPE: PRT
<213> ORGANISM: Homo sapiens

<400> SEQUENCE: 1

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125
```

-continued

```
Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 2
<211> LENGTH: 189
<212> TYPE: PRT
<213> ORGANISM: Homo sapiens

<400> SEQUENCE: 2

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
                100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 3
<211> LENGTH: 189
<212> TYPE: PRT
<213> ORGANISM: Homo sapiens

<400> SEQUENCE: 3

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80
```

-continued

```
Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
            165                 170                 175

Gly Thr Gln Gly Cys Met Gly Leu Pro Cys Val Val Met
            180                 185
```

<210> SEQ ID NO 4
<211> LENGTH: 117
<212> TYPE: PRT
<213> ORGANISM: Artificial Sequence
<220> FEATURE:
<223> OTHER INFORMATION: Anti-pan RAS intracellular single domain
      antibody iDAb RAS

<400> SEQUENCE: 4

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Thr Phe Ser Met Asn Trp Val Arg Gln Ala Pro Gly Lys Gly Leu Glu
        35                  40                  45

Trp Val Ser Tyr Ile Ser Arg Thr Ser Lys Thr Ile Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Arg Phe Phe Asp Tyr Trp Gly Gln Gly Thr Leu
            100                 105                 110

Val Thr Val Ser Ser
        115
```

<210> SEQ ID NO 5
<211> LENGTH: 335
<212> TYPE: PRT
<213> ORGANISM: Artificial Sequence
<220> FEATURE:
<223> OTHER INFORMATION: Chimaeric protein UBOX-iDAb RAS

<400> SEQUENCE: 5

```
Met Arg Leu Asn Phe Gly Asp Asp Ile Pro Ser Ala Leu Arg Ile Ala
1               5                   10                  15

Lys Lys Lys Arg Trp Asn Ser Ile Glu Glu Arg Arg Ile His Gln Glu
            20                  25                  30

Ser Glu Leu His Ser Tyr Leu Ser Arg Leu Ile Ala Ala Glu Arg Glu
        35                  40                  45

Arg Glu Leu Glu Glu Cys Gln Arg Asn His Glu Gly Asp Glu Asp Asp
    50                  55                  60

Ser His Val Arg Ala Gln Gln Ala Cys Ile Glu Ala Lys His Asp Lys
```

-continued

```
65                    70                   75                    80

Tyr Met Ala Asp Met Asp Glu Leu Phe Ser Gln Val Asp Glu Lys Arg
                85                   90                   95

Lys Lys Arg Asp Ile Pro Asp Tyr Leu Cys Gly Lys Ile Ser Phe Glu
            100                 105                 110

Leu Met Arg Glu Pro Cys Ile Thr Pro Ser Gly Ile Thr Tyr Asp Arg
            115                 120                 125

Lys Asp Ile Glu Glu His Leu Gln Arg Val Gly His Phe Asp Pro Val
        130                 135                 140

Thr Arg Ser Pro Leu Thr Gln Glu Gln Leu Ile Pro Asn Leu Ala Met
145                 150                 155                 160

Lys Glu Val Ile Asp Ala Phe Ile Ser Glu Asn Gly Trp Val Glu Asp
                165                 170                 175

Tyr Leu Glu Gly Gly Gly Gly Ser Ala Ala Ala Met Asp Tyr Lys Asp
            180                 185                 190

Asp Asp Asp Lys Thr Ser Met Ala Glu Val Gln Leu Leu Glu Ser Gly
            195                 200                 205

Gly Gly Leu Val Gln Pro Gly Gly Ser Leu Arg Leu Ser Cys Ala Ala
        210                 215                 220

Ser Gly Phe Thr Phe Ser Thr Phe Ser Met Asn Trp Val Arg Gln Ala
225                 230                 235                 240

Pro Gly Lys Gly Leu Glu Trp Val Ser Tyr Ile Ser Arg Thr Ser Lys
            245                 250                 255

Thr Ile Tyr Tyr Ala Asp Ser Val Lys Gly Arg Phe Thr Ile Ser Arg
            260                 265                 270

Asp Asn Ser Lys Asn Thr Leu Tyr Leu Gln Met Asn Ser Leu Arg Ala
            275                 280                 285

Glu Asp Thr Ala Val Tyr Tyr Cys Ala Arg Gly Arg Phe Phe Asp Tyr
        290                 295                 300

Trp Gly Gln Gly Thr Leu Val Thr Val Ser Ser Lys Leu Asn Pro Pro
305                 310                 315                 320

Asp Glu Ser Gly Pro Gly Cys Met Ser Cys Lys Cys Val Leu Ser
            325                 330                 335
```

<210> SEQ ID NO 6
<211> LENGTH: 157
<212> TYPE: PRT
<213> ORGANISM: Artificial Sequence
<220> FEATURE:
<223> OTHER INFORMATION: Anti-KRAS DARPin K19

<400> SEQUENCE: 6

```
Met Asp Leu Gly Lys Lys Leu Leu Glu Ala Ala Arg Ala Gly Gln Asp
1               5                   10                  15

Asp Glu Val Arg Ile Leu Met Ala Asn Gly Ala Asp Val Asn Ala Ser
            20                  25                  30

Asp Arg Trp Gly Trp Thr Pro Leu His Leu Ala Ala Trp Trp Gly His
        35                  40                  45

Leu Glu Ile Val Glu Val Leu Leu Lys Arg Gly Ala Asp Val Ser Ala
    50                  55                  60

Ala Asp Leu His Gly Gln Ser Pro Leu His Leu Ala Ala Met Val Gly
65                  70                  75                  80

His Leu Glu Ile Val Glu Val Leu Leu Lys Tyr Gly Ala Asp Val Asn
                85                  90                  95

Ala Lys Asp Thr Met Gly Ala Thr Pro Leu His Leu Ala Ala Arg Ser
```

-continued

```
                    100                    105                    110
Gly His Leu Glu Ile Val Glu Glu Leu Leu Lys Asn Gly Ala Asp Met
          115                    120                    125

Asn Ala Gln Asp Lys Phe Gly Lys Thr Thr Phe Asp Ile Ser Thr Asp
      130                    135                    140

Asn Gly Asn Glu Asp Leu Ala Glu Ile Leu Gln Lys Leu
145                    150                    155
```

```
<210> SEQ ID NO 7
<211> LENGTH: 471
<212> TYPE: DNA
<213> ORGANISM: Artificial Sequence
<220> FEATURE:
<223> OTHER INFORMATION: DNA encoding DARPin K19

<400> SEQUENCE: 7
atggatctgg gaaaaaaact gctggaagcc gcgcgtgccg ggcaggacga tgaggtccgt        60
attcttatgg cgaatggtgc agatgttaac gcgagcgatc gttggggttg gacgccgctg       120
cacctggcag cgtggtgggg tcacctcgaa attgtggaag tgctgttgaa gcgcggtgca       180
gatgttagcg cggcagatct gcacggtcaa tcgccgctgc atctggcagc gatggtcggc       240
cacctcgaaa ttgtggaagt gctgttgaag tacggtgcag atgttaacgc gaaagatacg       300
atgggtgcaa cgccgctgca cctggcagcg cgaagcggtc acctcgaaat tgtggaagag       360
ctgttgaaga acggtgcaga tatgaatgct caggataagt ttggcaaaac cacgtttgat       420
atctccactg ataatggcaa cgaagattta gcggaaatcc tgcagaaact g               471
```

```
<210> SEQ ID NO 8
<211> LENGTH: 157
<212> TYPE: PRT
<213> ORGANISM: Artificial Sequence
<220> FEATURE:
<223> OTHER INFORMATION: Amino acid sequence of anti-KRAS DARPin K13

<400> SEQUENCE: 8

Met Asp Leu Gly Lys Lys Leu Leu Glu Ala Ala Arg Ala Gly Gln Asp
1               5                    10                    15

Asp Glu Val Arg Ile Leu Met Ala Asn Gly Ala Asp Val Asn Ala Ser
                20                    25                    30

Asp Arg Trp Gly Trp Thr Pro Leu His Leu Ala Ala Trp Trp Gly His
          35                    40                    45

Leu Glu Ile Val Glu Val Leu Leu Lys His Gly Ala Asp Val Asn Ala
      50                    55                    60

Ala Asp Leu His Gly Gln Thr Pro Leu His Leu Ala Ala Met Val Gly
65                    70                    75                    80

His Leu Glu Ile Val Glu Val Leu Leu Lys Tyr Gly Ala Asp Val Asn
                85                    90                    95

Ala Lys Asp Thr Met Gly Ala Thr Pro Leu His Leu Ala Ala Gln Ser
                100                    105                    110

Gly His Leu Glu Ile Val Glu Val Leu Leu Lys Asn Gly Ala Asp Val
          115                    120                    125

Asn Ala Gln Asp Lys Phe Gly Lys Thr Ala Phe Asp Ile Ser Ile Asp
      130                    135                    140

Asn Gly Asn Glu Asp Leu Ala Glu Ile Leu Gln Lys Leu
145                    150                    155
```

```
<210> SEQ ID NO 9
```

<211> LENGTH: 471
<212> TYPE: DNA
<213> ORGANISM: Artificial Sequence
<220> FEATURE:
<223> OTHER INFORMATION: DNA encoding K13

<400> SEQUENCE: 9

```
atggatctgg gaaaaaaact gctggaagcc gcgcgtgccg gacaggacga tgaggtccgt        60
attcttatgg cgaacggtgc agatgttaac gcgagcgatc gctgggggttg gacgccgctg       120 catctggcag cgtggtgggg tcacctcgaa attgtggaag tgctgttgaa gcacggtgca       180
gatgttaacg cggcagatct gcacggtcaa acgccgctgc atctggcagc gatggtcggt       240
cacctcgaaa ttgtggaagt gctgttgaag tacggtgcag atgttaacgc gaaagatacg       300
atgggtgcaa cgccgctgca tctggcagcg caaagcggtc acctcgaaat tgtggaagtg       360
ctgttgaaga cggtgcaga tgtgaatgct caggataagt ttggcaaaac cgcgtttgat       420
atctccattg ataatggcaa cgaagatttta gcggaaatcc tgcagaaact g              471
```

<210> SEQ ID NO 10
<211> LENGTH: 281
<212> TYPE: PRT
<213> ORGANISM: Artificial Sequence
<220> FEATURE:
<223> OTHER INFORMATION: anti-KRAS scFv P2-E2

<400> SEQUENCE: 10

```
Met Ala Glu Val Gln Leu Leu Glu Ser Gly Gly Gly Ser Val Gln Pro
1               5                   10                  15

Gly Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu Glu
            35                  40                  45

Trp Val Ser Ala Ile Ser Gly Ser Gly Gly Ser Thr Tyr Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Asp Tyr Gly Asp Tyr Phe Asp Tyr Trp Gly
            100                 105                 110

Gln Gly Thr Leu Val Thr Val Ser Ser Leu Glu Gly Gly Gly Gly Ser
        115                 120                 125

Gly Gly Gly Gly Ser Gly Gly Gly Ala Ser Asp Ile Val Met Thr Gln
    130                 135                 140

Ser Pro Gly Thr Leu Ser Leu Ser Pro Gly Glu Arg Ala Thr Leu Ser
145                 150                 155                 160

Cys Arg Ala Ser Gln Thr Val Ser Thr Tyr Leu Ala Trp Tyr Gln Gln
                165                 170                 175

Lys Pro Gly Gln Ala Pro Arg Leu Leu Ile Tyr Gly Ala Ser Ser Leu
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Ala Ala Val Tyr
    210                 215                 220

Tyr Cys Gln Gln Tyr Gly Ser Ser Val Ile Thr Phe Gly Gln Gly Thr
225                 230                 235                 240
```

-continued

```
Lys Leu Glu Ile Lys Arg Ala Ala Ala Ser Ala His His His His His
                245                 250                 255

His Lys Leu Asp Tyr Lys Asp His Asp Gly Asp Tyr Lys Asp His Asp
                260                 265                 270

Ile Asp Tyr Lys Asp Asp Asp Asp Lys
        275                 280

<210> SEQ ID NO 11
<211> LENGTH: 289
<212> TYPE: PRT
<213> ORGANISM: Artificial Sequence
<220> FEATURE:
<223> OTHER INFORMATION: anti-KRAS scFv P2-F3

<400> SEQUENCE: 11

Met Ala Glu Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
                20                  25                  30

Gly Tyr Tyr Met His Trp Val Arg Gln Ala Pro Gly Gln Gly Leu Glu
            35                  40                  45

Trp Met Gly Trp Ile Asn Pro Asn Ser Gly Gly Thr Asn Tyr Ala Gln
        50                  55                  60

Lys Phe Gln Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

Tyr Cys Ala Arg Asp Arg Gly Ser Ser Trp Tyr Val Ala Phe Asp Tyr
                100                 105                 110

Trp Gly Gln Gly Thr Leu Val Thr Val Ser Ser Leu Glu Gly Gly Gly
            115                 120                 125

Gly Ser Gly Gly Gly Gly Ser Gly Gly Gly Ala Ser Asp Ile Gln Met
        130                 135                 140

Thr Gln Ser Pro Asp Ser Leu Ala Val Ser Leu Gly Glu Arg Ala Thr
145                 150                 155                 160

Ile Ser Cys Lys Ser Ser Gln Ser Val Leu Tyr Lys Tyr Asn Asn Lys
                165                 170                 175

Asn Tyr Leu Ala Trp Tyr Gln Gln Lys Pro Gly Gln Pro Pro Lys Leu
            180                 185                 190

Ile Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
    210                 215                 220

Gln Pro Glu Asp Val Ala Val Tyr Tyr Cys Gln Gln Tyr Tyr Thr Thr
225                 230                 235                 240

Pro Tyr Thr Phe Gly Gln Gly Thr Lys Val Glu Ile Lys Arg Ala Ala
                245                 250                 255

Ala Ser Ala His His His His His His Lys Leu Asp Tyr Lys Asp His
                260                 265                 270

Asp Gly Asp Tyr Lys Asp His Asp Ile Asp Tyr Lys Asp Asp Asp Asp
        275                 280                 285

Lys

<210> SEQ ID NO 12
<211> LENGTH: 158
<212> TYPE: PRT
```

```
<213> ORGANISM: Homo sapiens

<400> SEQUENCE: 12

Met Ser Ser Ala Ile Glu Arg Lys Ser Leu Asp Pro Ser Glu Glu Pro
1               5                   10                  15

Val Asp Glu Val Leu Gln Ile Pro Pro Ser Leu Leu Thr Cys Gly Gly
            20                  25                  30

Cys Gln Gln Asn Ile Gly Asp Arg Tyr Phe Leu Lys Ala Ile Asp Gln
        35                  40                  45

Tyr Trp His Glu Asp Cys Leu Ser Cys Asp Leu Cys Gly Cys Arg Leu
    50                  55                  60

Gly Glu Val Gly Arg Arg Leu Tyr Tyr Lys Leu Gly Arg Lys Leu Cys
65                  70                  75                  80

Arg Arg Asp Tyr Leu Arg Leu Phe Gly Gln Asp Gly Leu Cys Ala Ser
                85                  90                  95

Cys Asp Lys Arg Ile Arg Ala Tyr Glu Met Thr Met Arg Val Lys Asp
            100                 105                 110

Lys Val Tyr His Leu Glu Cys Phe Lys Cys Ala Ala Cys Gln Lys His
            115                 120                 125

Phe Cys Val Gly Asp Arg Tyr Leu Leu Ile Asn Ser Asp Ile Val Cys
        130                 135                 140

Glu Gln Asp Ile Tyr Glu Trp Thr Lys Ile Asn Gly Met Ile
145                 150                 155

<210> SEQ ID NO 13
<211> LENGTH: 126
<212> TYPE: PRT
<213> ORGANISM: Artificial Sequence
<220> FEATURE:
<223> OTHER INFORMATION: anti-LMO2 VH576

<400> SEQUENCE: 13

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Ser Phe Ser
            20                  25                  30

His Ser Pro Met Asn Trp Val Arg Gln Ala Pro Gly Lys Gly Leu Glu
        35                  40                  45

Trp Val Ser Tyr Ile Ser Tyr Asn Ser Ser Ser Ile Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Leu Thr Glu Ser Leu Glu Leu Thr Ala Asp Trp
            100                 105                 110

Phe Asp Tyr Trp Gly Gln Gly Thr Leu Val Thr Val Ser Ser
        115                 120                 125

<210> SEQ ID NO 14
<211> LENGTH: 376
<212> TYPE: PRT
<213> ORGANISM: Artificial Sequence
<220> FEATURE:
<223> OTHER INFORMATION: Amino acid sequence of VHL-VH576, an
      exemplary chimaeric protein of the second aspect of the invention

<400> SEQUENCE: 14
```

```
Met Pro Arg Arg Ala Glu Asn Trp Asp Glu Ala Glu Val Gly Ala Glu
1               5                   10                  15

Glu Ala Gly Val Glu Glu Tyr Gly Pro Glu Glu Asp Gly Gly Glu Glu
                20                  25                  30

Ser Gly Ala Glu Glu Ser Gly Pro Glu Glu Ser Gly Pro Glu Glu Leu
            35                  40                  45

Gly Ala Glu Glu Glu Met Glu Ala Gly Arg Pro Arg Pro Val Leu Arg
        50                  55                  60

Ser Val Asn Ser Arg Glu Pro Ser Gln Val Ile Phe Cys Asn Arg Ser
65                  70                  75                  80

Pro Arg Val Val Leu Pro Val Trp Leu Asn Phe Asp Gly Glu Pro Gln
                85                  90                  95

Pro Tyr Pro Thr Leu Pro Pro Gly Thr Gly Arg Arg Ile His Ser Tyr
            100                 105                 110

Arg Gly His Leu Trp Leu Phe Arg Asp Ala Gly Thr His Asp Gly Leu
        115                 120                 125

Leu Val Asn Gln Thr Glu Leu Phe Val Pro Ser Leu Asn Val Asp Gly
        130                 135                 140

Gln Pro Ile Phe Ala Asn Ile Thr Leu Pro Val Tyr Thr Leu Lys Glu
145                 150                 155                 160

Arg Cys Leu Gln Val Val Arg Ser Leu Val Lys Pro Glu Asn Tyr Arg
                165                 170                 175

Arg Leu Asp Ile Val Arg Ser Leu Tyr Glu Asp Leu Glu Asp His Pro
                180                 185                 190

Asn Val Gln Lys Asp Leu Glu Arg Leu Thr Gln Glu Arg Ile Ala His
            195                 200                 205

Gln Arg Met Gly Asp Leu Glu Gly Gly Gly Ser Gly Gly Gly Gly
        210                 215                 220

Ser Gly Gly Gly Gly Ser Ala Ala Arg Met Ala Glu Val Gln Leu Leu
225                 230                 235                 240

Glu Ser Gly Gly Gly Leu Val Gln Pro Gly Gly Ser Leu Arg Leu Ser
                245                 250                 255

Cys Ala Ala Ser Gly Phe Ser Phe Ser His Ser Pro Met Asn Trp Val
                260                 265                 270

Arg Gln Ala Pro Gly Lys Gly Leu Glu Trp Val Ser Tyr Ile Ser Tyr
            275                 280                 285

Asn Ser Ser Ser Ile Tyr Tyr Ala Asp Ser Val Lys Gly Arg Phe Thr
        290                 295                 300

Ile Ser Arg Asp Asn Ser Lys Asn Thr Leu Tyr Leu Gln Met Asn Ser
305                 310                 315                 320

Leu Arg Ala Glu Asp Thr Ala Val Tyr Tyr Cys Ala Arg Gly Leu Thr
                325                 330                 335

Glu Ser Leu Glu Leu Thr Ala Asp Trp Phe Asp Tyr Trp Gly Gln Gly
            340                 345                 350

Thr Leu Val Thr Val Ser Ser Ala Ala Ala Glu Gln Lys Leu Ile Ser
            355                 360                 365

Glu Glu Asp Leu Asn Gly Ala Ala
        370                 375
```

<210> SEQ ID NO 15
<211> LENGTH: 213
<212> TYPE: PRT
<213> ORGANISM: Homo sapiens

<400> SEQUENCE: 15

-continued

```
Met Pro Arg Arg Ala Glu Asn Trp Asp Glu Ala Glu Val Gly Ala Glu
1               5                   10                  15

Glu Ala Gly Val Glu Glu Tyr Gly Pro Glu Glu Asp Gly Gly Glu Glu
                20                  25                  30

Ser Gly Ala Glu Glu Ser Gly Pro Glu Glu Ser Gly Pro Glu Glu Leu
            35                  40                  45

Gly Ala Glu Glu Glu Met Glu Ala Gly Arg Pro Arg Pro Val Leu Arg
        50                  55                  60

Ser Val Asn Ser Arg Glu Pro Ser Gln Val Ile Phe Cys Asn Arg Ser
65                  70                  75                  80

Pro Arg Val Val Leu Pro Val Trp Leu Asn Phe Asp Gly Glu Pro Gln
                85                  90                  95

Pro Tyr Pro Thr Leu Pro Pro Gly Thr Gly Arg Arg Ile His Ser Tyr
                100                 105                 110

Arg Gly His Leu Trp Leu Phe Arg Asp Ala Gly Thr His Asp Gly Leu
            115                 120                 125

Leu Val Asn Gln Thr Glu Leu Phe Val Pro Ser Leu Asn Val Asp Gly
        130                 135                 140

Gln Pro Ile Phe Ala Asn Ile Thr Leu Pro Val Tyr Thr Leu Lys Glu
145                 150                 155                 160

Arg Cys Leu Gln Val Val Arg Ser Leu Val Lys Pro Glu Asn Tyr Arg
                165                 170                 175

Arg Leu Asp Ile Val Arg Ser Leu Tyr Glu Asp Leu Glu Asp His Pro
                180                 185                 190

Asn Val Gln Lys Asp Leu Glu Arg Leu Thr Gln Glu Arg Ile Ala His
            195                 200                 205

Gln Arg Met Gly Asp
        210
```

```
<210> SEQ ID NO 16
<211> LENGTH: 639
<212> TYPE: DNA
<213> ORGANISM: Homo sapiens

<400> SEQUENCE: 16
atgccccgga gggcggagaa ctgggacgag gccgaggtag gcgcggagga ggcaggcgtc      60
gaagagtacg gccctgaaga agacggcggg gaggagtcgg gcgccgagga gtccggcccg     120
gaagagtccg gcccggagga actgggcgcc gaggaggaga tggaggccgg gcggccgcgg     180
cccgtgctgc gctcggtgaa ctcgcgcgag ccctcccagg tcatcttctg caatcgcagt     240
ccgcgcgtcg tgctgccagt atggctcaac ttcgacggcg agccgcagcc ctacccaacg     300
ctgccgcctg gcacgggccg ccgcatccac agctaccgag tcacctttg gctcttcaga      360 gatgcaggga cacacgatgg gcttctggtt aaccaaactg aattatttgt gccatctctc     420
aatgttgacg gacagcctat ttttgccaat atcacactgc cagtgtatac tctgaaagag     480
cgatgcctcc aggttgtccg gagcctagtc aagcctgaga attacaggag actggacatc     540
gtcaggtcgc tctacgaaga tctggaagac cacccaaatg tgcagaaaga cctggagcgg     600
ctgacacagg agcgcattgc acatcaacgg atgggagat                            639
```

```
<210> SEQ ID NO 17
<211> LENGTH: 177
<212> TYPE: PRT
<213> ORGANISM: Homo sapiens
```

<400> SEQUENCE: 17

Met Arg Leu Asn Phe Gly Asp Asp Ile Pro Ser Ala Leu Arg Ile Ala
1               5                   10                  15

Lys Lys Lys Arg Trp Asn Ser Ile Glu Glu Arg Arg Ile His Gln Glu
            20                  25                  30

Ser Glu Leu His Ser Tyr Leu Ser Arg Leu Ile Ala Ala Glu Arg Glu
        35                  40                  45

Arg Glu Leu Glu Glu Cys Gln Arg Asn His Glu Gly Asp Glu Asp Asp
    50                  55                  60

Ser His Val Arg Ala Gln Gln Ala Cys Ile Glu Ala Lys His Asp Lys
65                  70                  75                  80

Tyr Met Ala Asp Met Asp Glu Leu Phe Ser Gln Val Asp Glu Lys Arg
                85                  90                  95

Lys Lys Arg Asp Ile Pro Asp Tyr Leu Cys Gly Lys Ile Ser Phe Glu
            100                 105                 110

Leu Met Arg Glu Pro Cys Ile Thr Pro Ser Gly Ile Thr Tyr Asp Arg
        115                 120                 125

Lys Asp Ile Glu Glu His Leu Gln Arg Val Gly His Phe Asp Pro Val
    130                 135                 140

Thr Arg Ser Pro Leu Thr Gln Glu Gln Leu Ile Pro Asn Leu Ala Met
145                 150                 155                 160

Lys Glu Val Ile Asp Ala Phe Ile Ser Glu Asn Gly Trp Val Glu Asp
                165                 170                 175

Tyr

<210> SEQ ID NO 18
<211> LENGTH: 531
<212> TYPE: DNA
<213> ORGANISM: Homo sapiens

<400> SEQUENCE: 18
atgcggctga acttcgggga cgacatcccc agcgctcttc gaatcgcgaa gaagaagcgc      60
tggaacagca ttgaggagcg gcgcatccac caggagagcg agctgcactc ctacctctcc     120
aggctcattg ccgcggagcg tgagagggag ctggaagagt gccagcgaaa ccacgagggt     180
gatgaggacg acagccacgt ccgggcccag caggcctgca ttgaggccaa gcacgacaag     240
tacatggcgg acatggacga gcttttttct caggtggatg agaagaggaa gaagcgagac     300
atccccgact acctgtgtgg caagatcagc tttgagctga tgcgggagcc gtgcatcacg     360
cccagtggca tcacctacga ccgcaaggac atcgaggagc acctgcagcg tgtgggtcat     420
tttgaccccg tgacccggag ccccctgacc caggaacagc tcatccccaa cttggctatg     480
aaggaggtta ttgacgcatt catctctgag aatggctggg tggaggacta c              531

<210> SEQ ID NO 19
<211> LENGTH: 5
<212> TYPE: PRT
<213> ORGANISM: Artificial Sequence
<220> FEATURE:
<223> OTHER INFORMATION: Amino acid sequence of the linker sequence
      within VHL-DP-KRAS

<400> SEQUENCE: 19

Gly Gly Gly Gly Ser
1               5

<210> SEQ ID NO 20

```
<211> LENGTH: 393
<212> TYPE: PRT
<213> ORGANISM: Artificial Sequence
<220> FEATURE:
<223> OTHER INFORMATION: Amino acid sequence of VHL-DP KRAS (also
      referred to as VHL-K19), an exemplary chimaeric protein of the
      first aspect of the invention

<400> SEQUENCE: 20

Met Pro Arg Arg Ala Glu Asn Trp Asp Glu Ala Glu Val Gly Ala Glu
1               5                   10                  15

Glu Ala Gly Val Glu Glu Tyr Gly Pro Glu Glu Asp Gly Gly Glu Glu
                20                  25                  30

Ser Gly Ala Glu Glu Ser Gly Pro Glu Glu Ser Gly Pro Glu Glu Leu
            35                  40                  45

Gly Ala Glu Glu Glu Met Glu Ala Gly Arg Pro Arg Pro Val Leu Arg
        50                  55                  60

Ser Val Asn Ser Arg Glu Pro Ser Gln Val Ile Phe Cys Asn Arg Ser
65                  70                  75                  80

Pro Arg Val Val Leu Pro Val Trp Leu Asn Phe Asp Gly Glu Pro Gln
                85                  90                  95

Pro Tyr Pro Thr Leu Pro Pro Gly Thr Gly Arg Arg Ile His Ser Tyr
                100                 105                 110

Arg Gly His Leu Trp Leu Phe Arg Asp Ala Gly Thr His Asp Gly Leu
            115                 120                 125

Leu Val Asn Gln Thr Glu Leu Phe Val Pro Ser Leu Asn Val Asp Gly
        130                 135                 140

Gln Pro Ile Phe Ala Asn Ile Thr Leu Pro Val Tyr Thr Leu Lys Glu
145                 150                 155                 160

Arg Cys Leu Gln Val Val Arg Ser Leu Val Lys Pro Glu Asn Tyr Arg
                165                 170                 175

Arg Leu Asp Ile Val Arg Ser Leu Tyr Glu Asp Leu Glu Asp His Pro
                180                 185                 190

Asn Val Gln Lys Asp Leu Glu Arg Leu Thr Gln Glu Arg Ile Ala His
            195                 200                 205

Gln Arg Met Gly Asp Leu Glu Gly Gly Gly Ser Ala Ala Ala Met
        210                 215                 220

Asp Leu Gly Lys Lys Leu Leu Glu Ala Ala Arg Ala Gly Gln Asp Asp
225                 230                 235                 240

Glu Val Arg Ile Leu Met Ala Asn Gly Ala Asp Val Asn Ala Ser Asp
                245                 250                 255

Arg Trp Gly Trp Thr Pro Leu His Leu Ala Ala Trp Trp Gly His Leu
                260                 265                 270

Glu Ile Val Glu Val Leu Leu Lys Arg Gly Ala Asp Val Ser Ala Ala
            275                 280                 285

Asp Leu His Gly Gln Ser Pro Leu His Leu Ala Ala Met Val Gly His
        290                 295                 300

Leu Glu Ile Val Glu Val Leu Leu Lys Tyr Gly Ala Asp Val Asn Ala
305                 310                 315                 320

Lys Asp Thr Met Gly Ala Thr Pro Leu His Leu Ala Ala Arg Ser Gly
                325                 330                 335

His Leu Glu Ile Val Glu Glu Leu Leu Lys Asn Gly Ala Asp Met Asn
            340                 345                 350

Ala Gln Asp Lys Phe Gly Lys Thr Thr Phe Asp Ile Ser Thr Asp Asn
        355                 360                 365
```

-continued

```
Gly Asn Glu Asp Leu Ala Glu Ile Leu Gln Lys Leu Val Asp Gly Gly
    370             375             380

Ser Asp Tyr Lys Asp Asp Asp Lys
385             390

<210> SEQ ID NO 21
<211> LENGTH: 1182
<212> TYPE: DNA
<213> ORGANISM: Artificial Sequence
<220> FEATURE:
<223> OTHER INFORMATION: DNA sequence encoding protein VHL-DP KRAS

<400> SEQUENCE: 21
atgccccgga gggcggagaa ctgggacgag gccgaggtag gcgcggagga ggcaggcgtc      60
gaagagtacg gccctgaaga agacggcggg gaggagtcgg gcgccgagga gtccggcccg     120
gaagagtccg gcccggagga actgggcgcc gaggaggaga tggaggccgg gcggccgcgg     180
cccgtgctgc gctcggtgaa ctcgcgcgag ccctcccagg tcatcttctg caatcgcagt     240
ccgcgcgtcg tgctgccagt atggctcaac ttcgacggcg agccgcagcc ctacccaacg     300
ctgccgcctg gcacgggccg ccgcatccac agctaccgag gtcacctttg gctcttcaga     360
gatgcaggga cacacgatgg gcttctggtt aaccaaactg aattatttgt gccatctctc     420
aatgttgacg gacagcctat ttttgccaat atcacactgc cagtgtatac tctgaaagag     480
cgatgcctcc aggttgtccg gagcctagtc aagcctgaga attacaggag actggacatc     540
gtcaggtcgc tctacgaaga tctggaagac cacccaaatg tgcagaaaga cctggagcgg     600
ctgacacagg agcgcattgc acatcaacgg atgggagatc tcgagggcgg aggcggatct     660
gcggccgcaa tggatctggg aaaaaaactg ctggaagccg cgcgtgccgg gcaggacgat     720
gaggtccgta ttcttatggc gaatggtgca gatgttaacg cgagcgatcg ttggggttgg     780
acgccgctgc acctggcagc gtggtggggt cacctcgaaa ttgtggaagt gctgttgaag     840
cgcggtgcag atgttagcgc ggcagatctg cacggtcaat cgccgctgca tctggcagcg     900
atggtcggcc acctcgaaat tgtggaagtg ctgttgaagt acggtgcaga tgttaacgcg     960
aaagatacga tgggtgcaac gccgctgcac ctggcagcgc gaagcggtca cctcgaaatt    1020
gtggaagagc tgttgaagaa cggtgcagat atgaatgctc aggataagtt tggcaaaacc    1080
acgtttgata tctccactga taatggcaac gaagatttag cggaaatcct gcagaaactg    1140
gtcgacggcg ggtctgacta caaagacgac gatgacaagt aa                       1182

<210> SEQ ID NO 22
<211> LENGTH: 393
<212> TYPE: PRT
<213> ORGANISM: Artificial Sequence
<220> FEATURE:
<223> OTHER INFORMATION: Amino acid sequence of VHL-K13, an exemplary
      chimaeric protein of the first aspect of the invention

<400> SEQUENCE: 22

Met Pro Arg Arg Ala Glu Asn Trp Asp Glu Ala Glu Val Gly Ala Glu
1               5                   10                  15

Glu Ala Gly Val Glu Glu Tyr Gly Pro Glu Glu Asp Gly Gly Glu Glu
            20                  25                  30

Ser Gly Ala Glu Glu Ser Gly Pro Glu Glu Ser Gly Pro Glu Glu Leu
        35                  40                  45

Gly Ala Glu Glu Glu Met Glu Ala Gly Arg Pro Arg Pro Val Leu Arg
    50                  55                  60
```

-continued

```
Ser Val Asn Ser Arg Glu Pro Ser Gln Val Ile Phe Cys Asn Arg Ser
65              70              75              80

Pro Arg Val Val Leu Pro Val Trp Leu Asn Phe Asp Gly Glu Pro Gln
                85              90              95

Pro Tyr Pro Thr Leu Pro Pro Gly Thr Gly Arg Arg Ile His Ser Tyr
            100             105             110

Arg Gly His Leu Trp Leu Phe Arg Asp Ala Gly Thr His Asp Gly Leu
        115             120             125

Leu Val Asn Gln Thr Glu Leu Phe Val Pro Ser Leu Asn Val Asp Gly
        130             135             140

Gln Pro Ile Phe Ala Asn Ile Thr Leu Pro Val Tyr Thr Leu Lys Glu
145             150             155             160

Arg Cys Leu Gln Val Val Arg Ser Leu Val Lys Pro Glu Asn Tyr Arg
            165             170             175

Arg Leu Asp Ile Val Arg Ser Leu Tyr Glu Asp Leu Glu Asp His Pro
            180             185             190

Asn Val Gln Lys Asp Leu Glu Arg Leu Thr Gln Glu Arg Ile Ala His
            195             200             205

Gln Arg Met Gly Asp Leu Glu Gly Gly Gly Ser Ala Ala Ala Met
        210             215             220

Asp Leu Gly Lys Lys Leu Leu Glu Ala Ala Arg Ala Gly Gln Asp Asp
225             230             235             240

Glu Val Arg Ile Leu Met Ala Asn Gly Ala Asp Val Asn Ala Ser Asp
            245             250             255

Arg Trp Gly Trp Thr Pro Leu His Leu Ala Ala Trp Trp Gly His Leu
            260             265             270

Glu Ile Val Glu Val Leu Leu Lys His Gly Ala Asp Val Asn Ala Ala
            275             280             285

Asp Leu His Gly Gln Thr Pro Leu His Leu Ala Ala Met Val Gly His
        290             295             300

Leu Glu Ile Val Glu Val Leu Leu Lys Tyr Gly Ala Asp Val Asn Ala
305             310             315             320

Lys Asp Thr Met Gly Ala Thr Pro Leu His Leu Ala Ala Gln Ser Gly
            325             330             335

His Leu Glu Ile Val Glu Val Leu Leu Lys Asn Gly Ala Asp Val Asn
            340             345             350

Ala Gln Asp Lys Phe Gly Lys Thr Ala Phe Asp Ile Ser Ile Asp Asn
            355             360             365

Gly Asn Glu Asp Leu Ala Glu Ile Leu Gln Lys Leu Val Asp Gly Gly
        370             375             380

Ser Asp Tyr Lys Asp Asp Asp Lys
385             390
```

```
<210> SEQ ID NO 23
<211> LENGTH: 1182
<212> TYPE: DNA
<213> ORGANISM: Artificial Sequence
<220> FEATURE:
<223> OTHER INFORMATION: DNA sequence encoding VHL-K13

<400> SEQUENCE: 23
atgccccgga gggcggagaa ctgggacgag gccgaggtag gcgcggagga ggcaggcgtc      60
gaagagtacg gccctgaaga agacggcggg gaggagtcgg gcgccgagga gtccggcccg     120
gaagagtccg gcccggagga actgggcgcc gaggaggaga tggaggccgg gcggccgcgg     180
```

-continued

```
cccgtgctgc gctcggtgaa ctcgcgcgag ccctcccagg tcatcttctg caatcgcagt     240
ccgcgcgtcg tgctgccagt atggctcaac ttcgacggcg agccgcagcc ctacccaacg     300
ctgccgcctg gcacgggccg ccgcatccac agctaccgag gtcacctttg gctcttcaga     360
gatgcaggga cacacgatgg gcttctggtt aaccaaactg aattatttgt gccatctctc     420
aatgttgacg gacagcctat ttttgccaat atcacactgc cagtgtatac tctgaaagag     480
cgatgcctcc aggttgtccg gagcctagtc aagcctgaga attacaggag actggacatc     540
gtcaggtcgc tctacgaaga tctggaagac cacccaaatg tgcagaaaga cctggagcgg     600
ctgacacagg agcgcattgc acatcaacgg atgggagatc tcgagggcgg aggcggatct     660
gcggccgcaa tggatctggg aaaaaaactg ctggaagccg cgcgtgccgg acaggacgat     720
gaggtccgta ttcttatggc gaacggtgca gatgttaacg cgagcgatcg ctggggttgg     780
acgccgctgc atctggcagc gtggtggggt cacctcgaaa ttgtggaagt gctgttgaag     840
cacggtgcag atgttaacgc ggcagatctg cacggtcaaa cgccgctgca tctggcagcg     900
atggtcggtc acctcgaaat tgtggaagtg ctgttgaagt acggtgcaga tgttaacgcg     960
aaagatacga tgggtgcaac gccgctgcat ctggcagcgc aaagcggtca cctcgaaatt    1020
gtggaagtgc tgttgaagaa cggtgcagat gtgaatgctc aggataagtt tggcaaaacc    1080
gcgtttgata tctccattga taatggcaac gaagatttag cggaaatcct gcagaaactg    1140
gtcgacggcg ggtctgacta caaagacgac gatgacaagt aa                       1182
```

```
<210> SEQ ID NO 24
<211> LENGTH: 357
<212> TYPE: PRT
<213> ORGANISM: Artificial Sequence
<220> FEATURE:
<223> OTHER INFORMATION: Amino acid sequence of UBOX-DP-KRAS, an
      exemplary chimaeric protein of the first aspect of the invention

<400> SEQUENCE: 24

Met Arg Leu Asn Phe Gly Asp Asp Ile Pro Ser Ala Leu Arg Ile Ala
1               5                   10                  15

Lys Lys Lys Arg Trp Asn Ser Ile Glu Glu Arg Arg Ile His Gln Glu
            20                  25                  30

Ser Glu Leu His Ser Tyr Leu Ser Arg Leu Ile Ala Ala Glu Arg Glu
        35                  40                  45

Arg Glu Leu Glu Glu Cys Gln Arg Asn His Glu Gly Asp Glu Asp Asp
    50                  55                  60

Ser His Val Arg Ala Gln Gln Ala Cys Ile Glu Ala Lys His Asp Lys
65                  70                  75                  80

Tyr Met Ala Asp Met Asp Glu Leu Phe Ser Gln Val Asp Glu Lys Arg
                85                  90                  95

Lys Lys Arg Asp Ile Pro Asp Tyr Leu Cys Gly Lys Ile Ser Phe Glu
            100                 105                 110

Leu Met Arg Glu Pro Cys Ile Thr Pro Ser Gly Ile Thr Tyr Asp Arg
        115                 120                 125

Lys Asp Ile Glu Glu His Leu Gln Arg Val Gly His Phe Asp Pro Val
    130                 135                 140

Thr Arg Ser Pro Leu Thr Gln Glu Gln Leu Ile Pro Asn Leu Ala Met
145                 150                 155                 160

Lys Glu Val Ile Asp Ala Phe Ile Ser Glu Asn Gly Trp Val Glu Asp
                165                 170                 175

Tyr Leu Glu Gly Gly Gly Gly Ser Ala Ala Ala Met Asp Leu Gly Lys
```

-continued

```
              180              185              190

Lys Leu Leu Glu Ala Ala Arg Ala Gly Gln Asp Asp Glu Val Arg Ile
        195              200              205

Leu Met Ala Asn Gly Ala Asp Val Asn Ala Ser Asp Arg Trp Gly Trp
        210              215              220

Thr Pro Leu His Leu Ala Ala Trp Trp Gly His Leu Glu Ile Val Glu
225              230              235              240

Val Leu Leu Lys Arg Gly Ala Asp Val Ser Ala Ala Asp Leu His Gly
            245              250              255

Gln Ser Pro Leu His Leu Ala Ala Met Val Gly His Leu Glu Ile Val
        260              265              270

Glu Val Leu Leu Lys Tyr Gly Ala Asp Val Asn Ala Lys Asp Thr Met
        275              280              285

Gly Ala Thr Pro Leu His Leu Ala Ala Arg Ser Gly His Leu Glu Ile
        290              295              300

Val Glu Glu Leu Leu Lys Asn Gly Ala Asp Met Asn Ala Gln Asp Lys
305              310              315              320

Phe Gly Lys Thr Thr Phe Asp Ile Ser Thr Asp Asn Gly Asn Glu Asp
            325              330              335

Leu Ala Glu Ile Leu Gln Lys Leu Val Asp Gly Gly Ser Asp Tyr Lys
        340              345              350

Asp Asp Asp Asp Lys
        355

<210> SEQ ID NO 25
<211> LENGTH: 1071
<212> TYPE: DNA
<213> ORGANISM: Artificial Sequence
<220> FEATURE:
<223> OTHER INFORMATION: DNA sequence encoding UBOX-DP-KRAS

<400> SEQUENCE: 25
atgcggctga acttcgggga cgacatcccc agcgctcttc gaatcgcgaa gaagaagcgc      60
tggaacagca ttgaggagcg gcgcatccac caggagagcg agctgcactc ctacctctcc     120
aggctcattg ccgcggagcg tgagagggag ctggaagagt gccagcgaaa ccacgagggt     180
gatgaggacg acagccacgt ccgggcccag caggcctgca ttgaggccaa gcacgacaag     240
tacatggcgg acatggacga gcttttttct caggtggatg agaagaggaa gaagcgagac     300
atccccgact acctgtgtgg caagatcagc tttgagctga tgcgggagcc gtgcatcacg     360
cccagtggca tcacctacga ccgcaaggac atcgaggagc acctgcagcg tgtgggtcat     420
tttgaccccg tgacccggag ccccctgacc caggaacagc tcatccccaa cttggctatg     480
aaggaggtta ttgacgcatt catctctgag aatggctggg tggaggacta cctcgagggc     540
ggaggcggat ctgcggccgc aatggatctg ggaaaaaaac tgctggaagc cgcgcgtgcc     600
gggcaggacg atgaggtccg tattcttatg gcgaatggtg cagatgttaa cgcgagcgat     660
cgttggggtt ggacgccgct gcacctggca gcgtggtggg gtcacctcga aattgtggaa     720
gtgctgttga gcgcgggtgc agatgttagc gcggcagatc tgcacggtca atcgccgctg     780
catctggcag cgatggtcgg ccacctcgaa attgtggaag tgctgttgaa gtacggtgca     840
gatgttaacg cgaaagatac gatgggtgca acgccgctgc acctggcagc gcgaagcggt     900
cacctcgaaa ttgtggaaga gctgttgaag aacggtgcag atatgaatgc tcaggataag     960
tttggcaaaa ccacgtttga tatctccact gataatggca cgaagatttt agcggaaatc    1020
```

-continued ctgcagaaac tggtcgacgg cgggtctgac tacaaagacg acgatgacaa g                    1071

<210> SEQ ID NO 26
<211> LENGTH: 484
<212> TYPE: PRT
<213> ORGANISM: Artificial Sequence
<220> FEATURE:
<223> OTHER INFORMATION: Amino acid sequence of VHL-P2-E2, an exemplary
      chimaeric protein of the first aspect of the invention

<400> SEQUENCE: 26

Met Pro Arg Arg Ala Glu Asn Trp Asp Glu Ala Glu Val Gly Ala Glu
1               5                   10                  15

Glu Ala Gly Val Glu Glu Tyr Gly Pro Glu Glu Asp Gly Gly Glu Glu
            20                  25                  30

Ser Gly Ala Glu Glu Ser Gly Pro Glu Glu Ser Gly Pro Glu Glu Leu
        35                  40                  45

Gly Ala Glu Glu Glu Met Glu Ala Gly Arg Pro Arg Pro Val Leu Arg
    50                  55                  60

Ser Val Asn Ser Arg Glu Pro Ser Gln Val Ile Phe Cys Asn Arg Ser
65                  70                  75                  80

Pro Arg Val Val Leu Pro Val Trp Leu Asn Phe Asp Gly Glu Pro Gln
                85                  90                  95

Pro Tyr Pro Thr Leu Pro Pro Gly Thr Gly Arg Arg Ile His Ser Tyr
                100                 105                 110

Arg Gly His Leu Trp Leu Phe Arg Asp Ala Gly Thr His Asp Gly Leu
            115                 120                 125

Leu Val Asn Gln Thr Glu Leu Phe Val Pro Ser Leu Asn Val Asp Gly
        130                 135                 140

Gln Pro Ile Phe Ala Asn Ile Thr Leu Pro Val Tyr Thr Leu Lys Glu
145                 150                 155                 160

Arg Cys Leu Gln Val Val Arg Ser Leu Val Lys Pro Glu Asn Tyr Arg
                165                 170                 175

Arg Leu Asp Ile Val Arg Ser Leu Tyr Glu Asp Leu Glu Asp His Pro
                180                 185                 190

Asn Val Gln Lys Asp Leu Glu Arg Leu Thr Gln Glu Arg Ile Ala His
            195                 200                 205

Gln Arg Met Gly Asp Gly Gly Gly Ser Gly Gly Gly Gly Ser Gly
        210                 215                 220

Gly Gly Gly Ser Gly Gly Gly Gly Ser Met Ala Glu Val Gln Leu Leu
225                 230                 235                 240

Glu Ser Gly Gly Gly Ser Val Gln Pro Gly Gly Ser Leu Arg Leu Ser
                245                 250                 255

Cys Ala Ala Ser Gly Phe Thr Phe Ser Ser Tyr Ala Met Ser Trp Val
                260                 265                 270

Arg Gln Ala Pro Gly Lys Gly Leu Glu Trp Val Ser Ala Ile Ser Gly
            275                 280                 285

Ser Gly Gly Ser Thr Tyr Tyr Ala Asp Ser Val Lys Gly Arg Phe Thr
        290                 295                 300

Ile Ser Arg Asp Asn Ser Lys Asn Thr Leu Tyr Leu Gln Met Asn Ser
305                 310                 315                 320

Leu Arg Ala Glu Asp Thr Ala Val Tyr Tyr Cys Ala Arg Asp Arg Asp
                325                 330                 335

Tyr Gly Asp Tyr Phe Asp Tyr Trp Gly Gln Gly Thr Leu Val Thr Val
                340                 345                 350

```
Ser Ser Leu Glu Gly Gly Gly Ser Gly Gly Gly Gly Ser Gly Gly
        355             360             365

Gly Ala Ser Asp Ile Val Met Thr Gln Ser Pro Gly Thr Leu Ser Leu
    370             375             380

Ser Pro Gly Glu Arg Ala Thr Leu Ser Cys Arg Ala Ser Gln Thr Val
385             390             395             400

Ser Thr Tyr Leu Ala Trp Tyr Gln Gln Lys Pro Gly Gln Ala Pro Arg
            405             410             415

Leu Leu Ile Tyr Gly Ala Ser Ser Leu Ala Thr Gly Ile Pro Asp Arg
            420             425             430

Phe Ser Gly Ser Gly Ser Gly Thr Asp Phe Thr Leu Thr Ile Ser Arg
            435             440             445

Leu Glu Pro Glu Asp Ala Ala Val Tyr Tyr Cys Gln Gln Tyr Gly Ser
    450             455             460

Ser Val Ile Thr Phe Gly Gln Gly Thr Lys Leu Glu Ile Lys Arg Ala
465             470             475             480

Ala Ala Ser Ala
```

```
<210> SEQ ID NO 27
<211> LENGTH: 492
<212> TYPE: PRT
<213> ORGANISM: Artificial Sequence
<220> FEATURE:
<223> OTHER INFORMATION: Amino acid sequence of VHL-P2-F3, an exemplary
      chimaeric protein of the first aspect of the invention

<400> SEQUENCE: 27
```

```
Met Pro Arg Arg Ala Glu Asn Trp Asp Glu Ala Glu Val Gly Ala Glu
1               5               10              15

Glu Ala Gly Val Glu Glu Tyr Gly Pro Glu Glu Asp Gly Gly Glu Glu
            20              25              30

Ser Gly Ala Glu Glu Ser Gly Pro Glu Glu Ser Gly Pro Glu Glu Leu
        35              40              45

Gly Ala Glu Glu Glu Met Glu Ala Gly Arg Pro Arg Pro Val Leu Arg
    50              55              60

Ser Val Asn Ser Arg Glu Pro Ser Gln Val Ile Phe Cys Asn Arg Ser
65              70              75              80

Pro Arg Val Val Leu Pro Val Trp Leu Asn Phe Asp Gly Glu Pro Gln
            85              90              95

Pro Tyr Pro Thr Leu Pro Pro Gly Thr Gly Arg Arg Ile His Ser Tyr
            100             105             110

Arg Gly His Leu Trp Leu Phe Arg Asp Ala Gly Thr His Asp Gly Leu
        115             120             125

Leu Val Asn Gln Thr Glu Leu Phe Val Pro Ser Leu Asn Val Asp Gly
        130             135             140

Gln Pro Ile Phe Ala Asn Ile Thr Leu Pro Val Tyr Thr Leu Lys Glu
145             150             155             160

Arg Cys Leu Gln Val Val Arg Ser Leu Val Lys Pro Glu Asn Tyr Arg
            165             170             175

Arg Leu Asp Ile Val Arg Ser Leu Tyr Glu Asp Leu Glu Asp His Pro
            180             185             190

Asn Val Gln Lys Asp Leu Glu Arg Leu Thr Gln Glu Arg Ile Ala His
        195             200             205

Gln Arg Met Gly Asp Gly Gly Gly Ser Gly Gly Gly Gly Ser Gly
    210             215             220
```

-continued

```
Gly Gly Gly Ser Gly Gly Gly Ser Met Ala Glu Val Gln Leu Val
225             230             235             240

Gln Ser Gly Ala Glu Val Lys Lys Pro Gly Ala Ser Val Lys Val Ser
            245             250             255

Cys Lys Ala Ser Gly Tyr Thr Phe Thr Gly Tyr Tyr Met His Trp Val
            260             265             270

Arg Gln Ala Pro Gly Gln Gly Leu Glu Trp Met Gly Trp Ile Asn Pro
            275             280             285

Asn Ser Gly Gly Thr Asn Tyr Ala Gln Lys Phe Gln Gly Arg Val Thr
    290             295             300

Met Thr Arg Asp Thr Ser Ile Ser Thr Ala Tyr Met Glu Leu Ser Arg
305             310             315             320

Leu Arg Ser Asp Asp Thr Ala Val Tyr Tyr Cys Ala Arg Asp Arg Gly
            325             330             335

Ser Ser Trp Tyr Val Ala Phe Asp Tyr Trp Gly Gln Gly Thr Leu Val
            340             345             350

Thr Val Ser Ser Leu Glu Gly Gly Gly Ser Gly Gly Gly Gly Ser
            355             360             365

Gly Gly Gly Ala Ser Asp Ile Gln Met Thr Gln Ser Pro Asp Ser Leu
    370             375             380

Ala Val Ser Leu Gly Glu Arg Ala Thr Ile Ser Cys Lys Ser Ser Gln
385             390             395             400

Ser Val Leu Tyr Lys Tyr Asn Asn Lys Asn Tyr Leu Ala Trp Tyr Gln
            405             410             415

Gln Lys Pro Gly Gln Pro Pro Lys Leu Ile Ile Tyr Trp Ala Ser Thr
            420             425             430

Arg Glu Ser Gly Val Pro Asp Arg Phe Ser Gly Ser Gly Ser Gly Thr
            435             440             445

Asp Phe Thr Leu Thr Ile Ser Ser Leu Gln Pro Glu Asp Val Ala Val
    450             455             460

Tyr Tyr Cys Gln Gln Tyr Tyr Thr Thr Pro Tyr Thr Phe Gly Gln Gly
465             470             475             480

Thr Lys Val Glu Ile Lys Arg Ala Ala Ala Ser Ala
            485             490
```

<210> SEQ ID NO 28
<211> LENGTH: 448
<212> TYPE: PRT
<213> ORGANISM: Artificial Sequence
<220> FEATURE:
<223> OTHER INFORMATION: Amino acid sequence of UBOX-P2-E2, an
    exemplary chimaeric protein of the first aspect of the invention

<400> SEQUENCE: 28

```
Met Arg Leu Asn Phe Gly Asp Asp Ile Pro Ser Ala Leu Arg Ile Ala
1               5               10              15

Lys Lys Lys Arg Trp Asn Ser Ile Glu Glu Arg Arg Ile His Gln Glu
            20              25              30

Ser Glu Leu His Ser Tyr Leu Ser Arg Leu Ile Ala Ala Glu Arg Glu
        35              40              45

Arg Glu Leu Glu Glu Cys Gln Arg Asn His Glu Gly Asp Glu Asp Asp
    50              55              60

Ser His Val Arg Ala Gln Gln Ala Cys Ile Glu Ala Lys His Asp Lys
65              70              75              80

Tyr Met Ala Asp Met Asp Glu Leu Phe Ser Gln Val Asp Glu Lys Arg
                85              90              95
```

```
Lys Lys Arg Asp Ile Pro Asp Tyr Leu Cys Gly Lys Ile Ser Phe Glu
        100                 105                 110

Leu Met Arg Glu Pro Cys Ile Thr Pro Ser Gly Ile Thr Tyr Asp Arg
        115                 120                 125

Lys Asp Ile Glu Glu His Leu Gln Arg Val Gly His Phe Asp Pro Val
    130                 135                 140

Thr Arg Ser Pro Leu Thr Gln Glu Gln Leu Ile Pro Asn Leu Ala Met
145                 150                 155                 160

Lys Glu Val Ile Asp Ala Phe Ile Ser Glu Asn Gly Trp Val Glu Asp
                165                 170                 175

Tyr Gly Gly Gly Gly Ser Gly Gly Gly Ser Gly Gly Gly Gly Ser
                180                 185                 190

Gly Gly Gly Gly Ser Met Ala Glu Val Gln Leu Leu Glu Ser Gly Gly
                195                 200                 205

Gly Ser Val Gln Pro Gly Gly Ser Leu Arg Leu Ser Cys Ala Ala Ser
    210                 215                 220

Gly Phe Thr Phe Ser Ser Tyr Ala Met Ser Trp Val Arg Gln Ala Pro
225                 230                 235                 240

Gly Lys Gly Leu Glu Trp Val Ser Ala Ile Ser Gly Ser Gly Gly Ser
                245                 250                 255

Thr Tyr Tyr Ala Asp Ser Val Lys Gly Arg Phe Thr Ile Ser Arg Asp
                260                 265                 270

Asn Ser Lys Asn Thr Leu Tyr Leu Gln Met Asn Ser Leu Arg Ala Glu
        275                 280                 285

Asp Thr Ala Val Tyr Tyr Cys Ala Arg Asp Arg Asp Tyr Gly Asp Tyr
    290                 295                 300

Phe Asp Tyr Trp Gly Gln Gly Thr Leu Val Thr Val Ser Ser Leu Glu
305                 310                 315                 320

Gly Gly Gly Gly Ser Gly Gly Gly Gly Ser Gly Gly Gly Ala Ser Asp
                325                 330                 335

Ile Val Met Thr Gln Ser Pro Gly Thr Leu Ser Leu Ser Pro Gly Glu
                340                 345                 350

Arg Ala Thr Leu Ser Cys Arg Ala Ser Gln Thr Val Ser Thr Tyr Leu
        355                 360                 365

Ala Trp Tyr Gln Gln Lys Pro Gly Gln Ala Pro Arg Leu Leu Ile Tyr
    370                 375                 380

Gly Ala Ser Ser Leu Ala Thr Gly Ile Pro Asp Arg Phe Ser Gly Ser
385                 390                 395                 400

Gly Ser Gly Thr Asp Phe Thr Leu Thr Ile Ser Arg Leu Glu Pro Glu
                405                 410                 415

Asp Ala Ala Val Tyr Tyr Cys Gln Gln Tyr Gly Ser Ser Val Ile Thr
                420                 425                 430

Phe Gly Gln Gly Thr Lys Leu Glu Ile Lys Arg Ala Ala Ala Ser Ala
        435                 440                 445
```

<210> SEQ ID NO 29
<211> LENGTH: 456
<212> TYPE: PRT
<213> ORGANISM: Artificial Sequence
<220> FEATURE:
<223> OTHER INFORMATION: Amino acid sequence of UBOX-P2-F3, an
      exemplary chimaeric protein of the first aspect of the invention

<400> SEQUENCE: 29

```
Met Arg Leu Asn Phe Gly Asp Asp Ile Pro Ser Ala Leu Arg Ile Ala
```

-continued

```
1               5               10              15

Lys Lys Lys Arg Trp Asn Ser Ile Glu Glu Arg Arg Ile His Gln Glu
            20              25              30

Ser Glu Leu His Ser Tyr Leu Ser Arg Leu Ile Ala Ala Glu Arg Glu
            35              40              45

Arg Glu Leu Glu Glu Cys Gln Arg Asn His Glu Gly Asp Glu Asp Asp
        50              55              60

Ser His Val Arg Ala Gln Gln Ala Cys Ile Glu Ala Lys His Asp Lys
65              70              75              80

Tyr Met Ala Asp Met Asp Glu Leu Phe Ser Gln Val Asp Glu Lys Arg
                85              90              95

Lys Lys Arg Asp Ile Pro Asp Tyr Leu Cys Gly Lys Ile Ser Phe Glu
            100             105             110

Leu Met Arg Glu Pro Cys Ile Thr Pro Ser Gly Ile Thr Tyr Asp Arg
            115             120             125

Lys Asp Ile Glu Glu His Leu Gln Arg Val Gly His Phe Asp Pro Val
        130             135             140

Thr Arg Ser Pro Leu Thr Gln Glu Gln Leu Ile Pro Asn Leu Ala Met
145             150             155             160

Lys Glu Val Ile Asp Ala Phe Ile Ser Glu Asn Gly Trp Val Glu Asp
                165             170             175

Tyr Gly Gly Gly Gly Ser Gly Gly Gly Gly Ser Gly Gly Gly Gly Ser
            180             185             190

Gly Gly Gly Gly Ser Met Ala Glu Val Gln Leu Val Gln Ser Gly Ala
        195             200             205

Glu Val Lys Lys Pro Gly Ala Ser Val Lys Val Ser Cys Lys Ala Ser
        210             215             220

Gly Tyr Thr Phe Thr Gly Tyr Tyr Met His Trp Val Arg Gln Ala Pro
225             230             235             240

Gly Gln Gly Leu Glu Trp Met Gly Trp Ile Asn Pro Asn Ser Gly Gly
            245             250             255

Thr Asn Tyr Ala Gln Lys Phe Gln Gly Arg Val Thr Met Thr Arg Asp
            260             265             270

Thr Ser Ile Ser Thr Ala Tyr Met Glu Leu Ser Arg Leu Arg Ser Asp
            275             280             285

Asp Thr Ala Val Tyr Tyr Cys Ala Arg Asp Arg Gly Ser Ser Trp Tyr
        290             295             300

Val Ala Phe Asp Tyr Trp Gly Gln Gly Thr Leu Val Thr Val Ser Ser
305             310             315             320

Leu Glu Gly Gly Gly Gly Ser Gly Gly Gly Gly Ser Gly Gly Gly Ala
                325             330             335

Ser Asp Ile Gln Met Thr Gln Ser Pro Asp Ser Leu Ala Val Ser Leu
            340             345             350

Gly Glu Arg Ala Thr Ile Ser Cys Lys Ser Ser Gln Ser Val Leu Tyr
            355             360             365

Lys Tyr Asn Asn Lys Asn Tyr Leu Ala Trp Tyr Gln Gln Lys Pro Gly
        370             375             380

Gln Pro Pro Lys Leu Ile Ile Tyr Trp Ala Ser Thr Arg Glu Ser Gly
385             390             395             400

Val Pro Asp Arg Phe Ser Gly Ser Gly Ser Gly Thr Asp Phe Thr Leu
            405             410             415

Thr Ile Ser Ser Leu Gln Pro Glu Asp Val Ala Val Tyr Tyr Cys Gln
            420             425             430
```

```
Gln Tyr Tyr Thr Thr Pro Tyr Thr Phe Gly Gln Gly Thr Lys Val Glu
        435                 440                 445

Ile Lys Arg Ala Ala Ala Ser Ala
    450                 455

<210> SEQ ID NO 30
<211> LENGTH: 484
<212> TYPE: PRT
<213> ORGANISM: Artificial Sequence
<220> FEATURE:
<223> OTHER INFORMATION: Amino acid sequence of P2-E2-VHL, an exemplary
      chimaeric protein of the first aspect of the invention

<400> SEQUENCE: 30

Met Ala Glu Val Gln Leu Leu Glu Ser Gly Gly Gly Ser Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Asp Tyr Gly Asp Tyr Phe Asp Tyr Trp Gly
            100                 105                 110

Gln Gly Thr Leu Val Thr Val Ser Ser Leu Glu Gly Gly Gly Gly Ser
        115                 120                 125

Gly Gly Gly Gly Ser Gly Gly Gly Ala Ser Asp Ile Val Met Thr Gln
    130                 135                 140

Ser Pro Gly Thr Leu Ser Leu Ser Pro Gly Glu Arg Ala Thr Leu Ser
145                 150                 155                 160

Cys Arg Ala Ser Gln Thr Val Ser Thr Tyr Leu Ala Trp Tyr Gln Gln
                165                 170                 175

Lys Pro Gly Gln Ala Pro Arg Leu Leu Ile Tyr Gly Ala Ser Ser Leu
            180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Ala Ala Val Tyr
    210                 215                 220

Tyr Cys Gln Gln Tyr Gly Ser Ser Val Ile Thr Phe Gly Gln Gly Thr
225                 230                 235                 240

Lys Leu Glu Ile Lys Arg Ala Ala Ala Ser Ala Gly Gly Gly Gly Ser
            245                 250                 255

Gly Gly Gly Gly Ser Gly Gly Gly Gly Ser Gly Gly Gly Gly Ser Met
            260                 265                 270

Pro Arg Arg Ala Glu Asn Trp Asp Glu Ala Glu Val Gly Ala Glu Glu
            275                 280                 285

Ala Gly Val Glu Glu Tyr Gly Pro Glu Glu Asp Gly Gly Glu Glu Ser
        290                 295                 300

Gly Ala Glu Glu Ser Gly Pro Glu Glu Ser Gly Pro Glu Glu Leu Gly
305                 310                 315                 320

Ala Glu Glu Glu Met Glu Ala Gly Arg Pro Arg Pro Val Leu Arg Ser
```

```
                    325                     330                     335

Val Asn Ser Arg Glu Pro Ser Gln Val Ile Phe Cys Asn Arg Ser Pro
                340                     345                     350

Arg Val Val Leu Pro Val Trp Leu Asn Phe Asp Gly Glu Pro Gln Pro
                355                     360                     365

Tyr Pro Thr Leu Pro Pro Gly Thr Gly Arg Arg Ile His Ser Tyr Arg
        370                     375                     380

Gly His Leu Trp Leu Phe Arg Asp Ala Gly Thr His Asp Gly Leu Leu
    385                     390                     395                     400

Val Asn Gln Thr Glu Leu Phe Val Pro Ser Leu Asn Val Asp Gly Gln
                        405                     410                     415

Pro Ile Phe Ala Asn Ile Thr Leu Pro Val Tyr Thr Leu Lys Glu Arg
                420                     425                     430

Cys Leu Gln Val Val Arg Ser Leu Val Lys Pro Glu Asn Tyr Arg Arg
                435                     440                     445

Leu Asp Ile Val Arg Ser Leu Tyr Glu Asp Leu Glu Asp His Pro Asn
        450                     455                     460

Val Gln Lys Asp Leu Glu Arg Leu Thr Gln Glu Arg Ile Ala His Gln
    465                     470                     475                     480

Arg Met Gly Asp
```

```
<210> SEQ ID NO 31
<211> LENGTH: 492
<212> TYPE: PRT
<213> ORGANISM: Artificial Sequence
<220> FEATURE:
<223> OTHER INFORMATION: Amino acid sequence of P2-F3-VHL, an exemplary
      chimaeric protein of the first aspect of the invention

<400> SEQUENCE: 31

Met Ala Glu Val Gln Leu Val Gln Ser Gly Ala Glu Val Lys Lys Pro
    1               5                   10                  15

Gly Ala Ser Val Lys Val Ser Cys Lys Ala Ser Gly Tyr Thr Phe Thr
                20                  25                  30

Gly Tyr Tyr Met His Trp Val Arg Gln Ala Pro Gly Gln Gly Leu Glu
            35                  40                  45

Trp Met Gly Trp Ile Asn Pro Asn Ser Gly Gly Thr Asn Tyr Ala Gln
        50                  55                  60

Lys Phe Gln Gly Arg Val Thr Met Thr Arg Asp Thr Ser Ile Ser Thr
    65                  70                  75                  80

Ala Tyr Met Glu Leu Ser Arg Leu Arg Ser Asp Asp Thr Ala Val Tyr
                    85                  90                  95

Tyr Cys Ala Arg Asp Arg Gly Ser Ser Trp Tyr Val Ala Phe Asp Tyr
                100                     105                     110

Trp Gly Gln Gly Thr Leu Val Thr Val Ser Ser Leu Glu Gly Gly Gly
            115                     120                     125

Gly Ser Gly Gly Gly Gly Ser Gly Gly Gly Ala Ser Asp Ile Gln Met
            130                     135                     140

Thr Gln Ser Pro Asp Ser Leu Ala Val Ser Leu Gly Glu Arg Ala Thr
    145                     150                     155                     160

Ile Ser Cys Lys Ser Ser Gln Ser Val Leu Tyr Lys Tyr Asn Asn Lys
                        165                     170                     175

Asn Tyr Leu Ala Trp Tyr Gln Gln Lys Pro Gly Gln Pro Pro Lys Leu
                180                     185                     190

Ile Ile Tyr Trp Ala Ser Thr Arg Glu Ser Gly Val Pro Asp Arg Phe
```

-continued

```
              195                  200                  205
Ser Gly Ser Gly Ser Gly Thr Asp Phe Thr Leu Thr Ile Ser Ser Leu
    210                  215                  220
Gln Pro Glu Asp Val Ala Val Tyr Tyr Cys Gln Gln Tyr Tyr Thr Thr
225                  230                  235                  240
Pro Tyr Thr Phe Gly Gln Gly Thr Lys Val Glu Ile Lys Arg Ala Ala
                245                  250                  255
Ala Ser Ala Gly Gly Gly Gly Ser Gly Gly Gly Ser Gly Gly Gly
                260                  265                  270
Gly Ser Gly Gly Gly Gly Ser Met Pro Arg Arg Ala Glu Asn Trp Asp
                275                  280                  285
Glu Ala Glu Val Gly Ala Glu Glu Ala Gly Val Glu Glu Tyr Gly Pro
    290                  295                  300
Glu Glu Asp Gly Gly Glu Glu Ser Gly Ala Glu Glu Ser Gly Pro Glu
305                  310                  315                  320
Glu Ser Gly Pro Glu Glu Leu Gly Ala Glu Glu Glu Met Glu Ala Gly
                325                  330                  335
Arg Pro Arg Pro Val Leu Arg Ser Val Asn Ser Arg Glu Pro Ser Gln
                340                  345                  350
Val Ile Phe Cys Asn Arg Ser Pro Arg Val Val Leu Pro Val Trp Leu
                355                  360                  365
Asn Phe Asp Gly Glu Pro Gln Pro Tyr Pro Thr Leu Pro Pro Gly Thr
    370                  375                  380
Gly Arg Arg Ile His Ser Tyr Arg Gly His Leu Trp Leu Phe Arg Asp
385                  390                  395                  400
Ala Gly Thr His Asp Gly Leu Leu Val Asn Gln Thr Glu Leu Phe Val
                405                  410                  415
Pro Ser Leu Asn Val Asp Gly Gln Pro Ile Phe Ala Asn Ile Thr Leu
                420                  425                  430
Pro Val Tyr Thr Leu Lys Glu Arg Cys Leu Gln Val Val Arg Ser Leu
                435                  440                  445
Val Lys Pro Glu Asn Tyr Arg Arg Leu Asp Ile Val Arg Ser Leu Tyr
    450                  455                  460
Glu Asp Leu Glu Asp His Pro Asn Val Gln Lys Asp Leu Glu Arg Leu
465                  470                  475                  480
Thr Gln Glu Arg Ile Ala His Gln Arg Met Gly Asp
                485                  490
```

<210> SEQ ID NO 32
<211> LENGTH: 447
<212> TYPE: PRT
<213> ORGANISM: Artificial Sequence
<220> FEATURE:
<223> OTHER INFORMATION: Amino acid sequence of P2-E2-UBOX, an
      exemplary chimaeric protein of the first aspect of the invention

<400> SEQUENCE: 32

```
Met Ala Glu Val Gln Leu Leu Glu Ser Gly Gly Gly Ser Val Gln Pro
1               5                   10                  15
Gly Gly Ser Leu Arg Leu Ser Cys Ala Ala Ser Gly Phe Thr Phe Ser
                20                  25                  30
Ser Tyr Ala Met Ser Trp Val Arg Gln Ala Pro Gly Lys Gly Leu Glu
                35                  40                  45
Trp Val Ser Ala Ile Ser Gly Ser Gly Gly Ser Thr Tyr Tyr Ala Asp
    50                  55                  60
```

-continued

```
Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Asp Tyr Gly Asp Tyr Phe Asp Tyr Trp Gly
                100                 105                 110

Gln Gly Thr Leu Val Thr Val Ser Ser Leu Glu Gly Gly Gly Gly Ser
        115                 120                 125

Gly Gly Gly Gly Ser Gly Gly Gly Ala Ser Asp Ile Val Met Thr Gln
        130                 135                 140

Ser Pro Gly Thr Leu Ser Leu Ser Pro Gly Glu Arg Ala Thr Leu Ser
145                 150                 155                 160

Cys Arg Ala Ser Gln Thr Val Ser Thr Tyr Leu Ala Trp Tyr Gln Gln
                165                 170                 175

Lys Pro Gly Gln Ala Pro Arg Leu Leu Ile Tyr Gly Ala Ser Ser Leu
                180                 185                 190

Ala Thr Gly Ile Pro Asp Arg Phe Ser Gly Ser Gly Ser Gly Thr Asp
                195                 200                 205

Phe Thr Leu Thr Ile Ser Arg Leu Glu Pro Glu Asp Ala Ala Val Tyr
        210                 215                 220

Tyr Cys Gln Gln Tyr Gly Ser Ser Val Ile Thr Phe Gly Gln Gly Thr
225                 230                 235                 240

Lys Leu Glu Ile Lys Arg Ala Ala Ala Ser Ala Gly Gly Gly Gly Ser
                245                 250                 255

Gly Gly Gly Gly Ser Gly Gly Gly Gly Ser Gly Gly Gly Gly Ser Arg
        260                 265                 270

Leu Asn Phe Gly Asp Asp Ile Pro Ser Ala Leu Arg Ile Ala Lys Lys
        275                 280                 285

Lys Arg Trp Asn Ser Ile Glu Glu Arg Arg Ile His Gln Glu Ser Glu
        290                 295                 300

Leu His Ser Tyr Leu Ser Arg Leu Ile Ala Ala Glu Arg Glu Arg Glu
305                 310                 315                 320

Leu Glu Glu Cys Gln Arg Asn His Glu Gly Asp Glu Asp Asp Ser His
                325                 330                 335

Val Arg Ala Gln Gln Ala Cys Ile Glu Ala Lys His Asp Lys Tyr Met
                340                 345                 350

Ala Asp Met Asp Glu Leu Phe Ser Gln Val Asp Glu Lys Arg Lys Lys
                355                 360                 365

Arg Asp Ile Pro Asp Tyr Leu Cys Gly Lys Ile Ser Phe Glu Leu Met
        370                 375                 380

Arg Glu Pro Cys Ile Thr Pro Ser Gly Ile Thr Tyr Asp Arg Lys Asp
385                 390                 395                 400

Ile Glu Glu His Leu Gln Arg Val Gly His Phe Asp Pro Val Thr Arg
                405                 410                 415

Ser Pro Leu Thr Gln Glu Gln Leu Ile Pro Asn Leu Ala Met Lys Glu
                420                 425                 430

Val Ile Asp Ala Phe Ile Ser Glu Asn Gly Trp Val Glu Asp Tyr
        435                 440                 445
```

<210> SEQ ID NO 33
<211> LENGTH: 455
<212> TYPE: PRT
<213> ORGANISM: Artificial Sequence
<220> FEATURE:
<223> OTHER INFORMATION: Amino acid sequence of P2-F3-UBOX, an -continued exemplary chimaeric protein of the first aspect of the invention

<400> SEQUENCE: 33

```
Met Ala Glu Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
                20                  25                  30

Gly Tyr Tyr Met His Trp Val Arg Gln Ala Pro Gly Gln Gly Leu Glu
            35                  40                  45

Trp Met Gly Trp Ile Asn Pro Asn Ser Gly Gly Thr Asn Tyr Ala Gln
        50                  55                  60

Lys Phe Gln Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

Tyr Cys Ala Arg Asp Arg Gly Ser Ser Trp Tyr Val Ala Phe Asp Tyr
            100                 105                 110

Trp Gly Gln Gly Thr Leu Val Thr Val Ser Ser Leu Glu Gly Gly Gly
        115                 120                 125

Gly Ser Gly Gly Gly Gly Ser Gly Gly Gly Ala Ser Asp Ile Gln Met
    130                 135                 140

Thr Gln Ser Pro Asp Ser Leu Ala Val Ser Leu Gly Glu Arg Ala Thr
145                 150                 155                 160

Ile Ser Cys Lys Ser Ser Gln Ser Val Leu Tyr Lys Tyr Asn Asn Lys
                165                 170                 175

Asn Tyr Leu Ala Trp Tyr Gln Gln Lys Pro Gly Gln Pro Pro Lys Leu
            180                 185                 190

Ile Ile Tyr Trp Ala Ser Thr Arg Glu Ser Gly Val Pro Asp Arg Phe
            195                 200                 205

Ser Gly Ser Gly Ser Gly Thr Asp Phe Thr Leu Thr Ile Ser Ser Leu
    210                 215                 220

Gln Pro Glu Asp Val Ala Val Tyr Tyr Cys Gln Gln Tyr Tyr Thr Thr
225                 230                 235                 240

Pro Tyr Thr Phe Gly Gln Gly Thr Lys Val Glu Ile Lys Arg Ala Ala
                245                 250                 255

Ala Ser Ala Gly Gly Gly Gly Ser Gly Gly Gly Gly Ser Gly Gly Gly
            260                 265                 270

Gly Ser Gly Gly Gly Gly Ser Arg Leu Asn Phe Gly Asp Asp Ile Pro
    275                 280                 285

Ser Ala Leu Arg Ile Ala Lys Lys Lys Arg Trp Asn Ser Ile Glu Glu
    290                 295                 300

Arg Arg Ile His Gln Glu Ser Glu Leu His Ser Tyr Leu Ser Arg Leu
305                 310                 315                 320

Ile Ala Ala Glu Arg Glu Arg Glu Leu Glu Glu Cys Gln Arg Asn His
            325                 330                 335

Glu Gly Asp Glu Asp Asp Ser His Val Arg Ala Gln Gln Ala Cys Ile
            340                 345                 350

Glu Ala Lys His Asp Lys Tyr Met Ala Asp Met Asp Glu Leu Phe Ser
            355                 360                 365

Gln Val Asp Glu Lys Arg Lys Arg Asp Ile Pro Asp Tyr Leu Cys
    370                 375                 380

Gly Lys Ile Ser Phe Glu Leu Met Arg Glu Pro Cys Ile Thr Pro Ser
385                 390                 395                 400
```

-continued

```
Gly Ile Thr Tyr Asp Arg Lys Asp Ile Glu Glu His Leu Gln Arg Val
            405             410             415

Gly His Phe Asp Pro Val Thr Arg Ser Pro Leu Thr Gln Glu Gln Leu
            420             425             430

Ile Pro Asn Leu Ala Met Lys Glu Val Ile Asp Ala Phe Ile Ser Glu
            435             440             445

Asn Gly Trp Val Glu Asp Tyr
            450             455

<210> SEQ ID NO 34
<211> LENGTH: 335
<212> TYPE: PRT
<213> ORGANISM: Artificial Sequence
<220> FEATURE:
<223> OTHER INFORMATION: Amino acid sequence of iDAb RAS-UBOX, an
      exemplary chimaeric protein of the first aspect of the invention

<400> SEQUENCE: 34

Met Leu Cys Cys Met Arg Arg Thr Lys Gln Val Glu Lys Asn Asp Glu
1               5               10              15

Asp Gln Lys Ile Val Asp Met Asp Tyr Lys Asp Asp Asp Arg Pro
            20              25              30

Met Ala Glu Val Gln Leu Leu Glu Ser Gly Gly Gly Leu Val Gln Pro
            35              40              45

Gly Gly Ser Leu Arg Leu Ser Cys Ala Ala Ser Gly Phe Thr Phe Ser
            50              55              60

Thr Phe Ser Met Asn Trp Val Arg Gln Ala Pro Gly Lys Gly Leu Glu
65              70              75              80

Trp Val Ser Tyr Ile Ser Arg Thr Ser Lys Thr Ile Tyr Tyr Ala Asp
                85              90              95

Ser Val Lys Gly Arg Phe Thr Ile Ser Arg Asp Asn Ser Lys Asn Thr
            100             105             110

Leu Tyr Leu Gln Met Asn Ser Leu Arg Ala Glu Asp Thr Ala Val Tyr
            115             120             125

Tyr Cys Ala Arg Gly Arg Phe Phe Asp Tyr Trp Gly Gln Gly Thr Leu
    130             135             140

Val Thr Val Ser Ser Leu Glu Gly Gly Gly Ser Ala Ala Ala Arg
145             150             155             160

Leu Asn Phe Gly Asp Asp Ile Pro Ser Ala Leu Arg Ile Ala Lys Lys
            165             170             175

Lys Arg Trp Asn Ser Ile Glu Glu Arg Arg Ile His Gln Glu Ser Glu
            180             185             190

Leu His Ser Tyr Leu Ser Arg Leu Ile Ala Ala Glu Arg Glu Arg Glu
            195             200             205

Leu Glu Glu Cys Gln Arg Asn His Glu Gly Asp Glu Asp Asp Ser His
    210             215             220

Val Arg Ala Gln Gln Ala Cys Ile Glu Ala Lys His Asp Lys Tyr Met
225             230             235             240

Ala Asp Met Asp Glu Leu Phe Ser Gln Val Asp Glu Lys Arg Lys Lys
            245             250             255

Arg Asp Ile Pro Asp Tyr Leu Cys Gly Lys Ile Ser Phe Glu Leu Met
            260             265             270

Arg Glu Pro Cys Ile Thr Pro Ser Gly Ile Thr Tyr Asp Arg Lys Asp
            275             280             285

Ile Glu Glu His Leu Gln Arg Val Gly His Phe Asp Pro Val Thr Arg
    290             295             300
```

-continued

```
Ser Pro Leu Thr Gln Glu Gln Leu Ile Pro Asn Leu Ala Met Lys Glu
305             310             315             320

Val Ile Asp Ala Phe Ile Ser Glu Asn Gly Trp Val Glu Asp Tyr
                325             330             335

<210> SEQ ID NO 35
<211> LENGTH: 371
<212> TYPE: PRT
<213> ORGANISM: Artificial Sequence
<220> FEATURE:
<223> OTHER INFORMATION: Amino acid sequence of VHL-iDAb RAS, an
      exemplary chimaeric protein of the first aspect of the invention

<400> SEQUENCE: 35

Met Pro Arg Arg Ala Glu Asn Trp Asp Glu Ala Glu Val Gly Ala Glu
1               5               10              15

Glu Ala Gly Val Glu Glu Tyr Gly Pro Glu Glu Asp Gly Gly Glu Glu
                20              25              30

Ser Gly Ala Glu Glu Ser Gly Pro Glu Glu Ser Gly Pro Glu Glu Leu
        35              40              45

Gly Ala Glu Glu Glu Met Glu Ala Gly Arg Pro Arg Pro Val Leu Arg
    50              55              60

Ser Val Asn Ser Arg Glu Pro Ser Gln Val Ile Phe Cys Asn Arg Ser
65              70              75              80

Pro Arg Val Val Leu Pro Val Trp Leu Asn Phe Asp Gly Glu Pro Gln
                85              90              95

Pro Tyr Pro Thr Leu Pro Pro Gly Thr Gly Arg Arg Ile His Ser Tyr
        100             105             110

Arg Gly His Leu Trp Leu Phe Arg Asp Ala Gly Thr His Asp Gly Leu
        115             120             125

Leu Val Asn Gln Thr Glu Leu Phe Val Pro Ser Leu Asn Val Asp Gly
    130             135             140

Gln Pro Ile Phe Ala Asn Ile Thr Leu Pro Val Tyr Thr Leu Lys Glu
145             150             155             160

Arg Cys Leu Gln Val Val Arg Ser Leu Val Lys Pro Glu Asn Tyr Arg
                165             170             175

Arg Leu Asp Ile Val Arg Ser Leu Tyr Glu Asp Leu Glu Asp His Pro
        180             185             190

Asn Val Gln Lys Asp Leu Glu Arg Leu Thr Gln Glu Arg Ile Ala His
        195             200             205

Gln Arg Met Gly Asp Leu Glu Gly Gly Gly Ser Ala Ala Ala Met
    210             215             220

Asp Tyr Lys Asp Asp Asp Asp Lys Thr Ser Met Ala Glu Val Gln Leu
225             230             235             240

Leu Glu Ser Gly Gly Gly Leu Val Gln Pro Gly Gly Ser Leu Arg Leu
                245             250             255

Ser Cys Ala Ala Ser Gly Phe Thr Phe Ser Thr Phe Ser Met Asn Trp
                260             265             270

Val Arg Gln Ala Pro Gly Lys Gly Leu Glu Trp Val Ser Tyr Ile Ser
        275             280             285

Arg Thr Ser Lys Thr Ile Tyr Tyr Ala Asp Ser Val Lys Gly Arg Phe
        290             295             300

Thr Ile Ser Arg Asp Asn Ser Lys Asn Thr Leu Tyr Leu Gln Met Asn
305             310             315             320

Ser Leu Arg Ala Glu Asp Thr Ala Val Tyr Tyr Cys Ala Arg Gly Arg
```

-continued

```
             325              330              335
Phe Phe Asp Tyr Trp Gly Gln Gly Thr Leu Val Thr Val Ser Ser Lys
             340              345              350
Leu Asn Pro Pro Asp Glu Ser Gly Pro Gly Cys Met Ser Cys Lys Cys
             355              360              365
Val Leu Ser
    370
```

```
<210> SEQ ID NO 36
<211> LENGTH: 22
<212> TYPE: DNA
<213> ORGANISM: Artificial Sequence
<220> FEATURE:
<223> OTHER INFORMATION: DNA sequence of primer DUSP6For

<400> SEQUENCE: 36
ctcggatcac tggagccaaa ac                                              22

<210> SEQ ID NO 37
<211> LENGTH: 22
<212> TYPE: DNA
<213> ORGANISM: Artificial Sequence
<220> FEATURE:
<223> OTHER INFORMATION: DNA sequence of primer DUSP6Rev

<400> SEQUENCE: 37
gtcacagtga ctgagcggct aa                                              22

<210> SEQ ID NO 38
<211> LENGTH: 22
<212> TYPE: DNA
<213> ORGANISM: Artificial Sequence
<220> FEATURE:
<223> OTHER INFORMATION: DNA sequence of primer GAPDHFor

<400> SEQUENCE: 38
gtctcctctg acttcaacag cg                                              22

<210> SEQ ID NO 39
<211> LENGTH: 22
<212> TYPE: DNA
<213> ORGANISM: Artificial Sequence
<220> FEATURE:
<223> OTHER INFORMATION: DNA sequence of primer GAPDHRev

<400> SEQUENCE: 39
accaccctgt tgctgtagcc aa                                              22

<210> SEQ ID NO 40
<211> LENGTH: 5
<212> TYPE: PRT
<213> ORGANISM: Artificial Sequence
<220> FEATURE:
<223> OTHER INFORMATION: Amino acid sequence of optional sequence
      within certain exemplary proteins of the invention

<400> SEQUENCE: 40

Val Asp Gly Gly Ser
1               5

<210> SEQ ID NO 41
<211> LENGTH: 8
<212> TYPE: PRT
<213> ORGANISM: Artificial Sequence
<220> FEATURE:
```

-continued

<223> OTHER INFORMATION: Amino acid sequence of optional FLAG tag
      sequence in exemplary proteins of the invention <400> SEQUENCE: 41

Asp Tyr Lys Asp Asp Asp Asp Lys
1               5

FUNCTIONAL IMAGING FEATURES FROM COMPUTED TOMOGRAPHY IMAGES

CROSS-REFERENCE TO RELATED APPLICATIONS

This application is the National Stage of International Application No. PCT/GB2021/051141, filed May 12, 2021, which claims priority to GB 2007256.7, filed May 15, 2020, which are entirely incorporated herein by reference.

TECHNICAL FIELD

The present disclosure relates to image analysis. In particular, the present disclosure relates to medical image analysis.

BACKGROUND

Functional imaging modalities such as positron emission tomography (PET) scans are routinely used clinically for the detection of functional activity within a body, for example metabolic activity, cancer metastasis or tissue inflammation.

Typically, a radioactive tracer (also known as a radiopharmaceutical, radiotracer or radioactive label) is administered, usually by injection, to the patient or subject in advance of the scan. A radiotracer is a drug that can be used for diagnostic or therapeutic purposes and comprises a radio-isotope bonded to a molecule. The radiopharmaceutical conveys the isotope to specific organs, tissues or cells and is typically selected for its properties and purpose. Many radiopharmaceuticals are known in the art and they can usually be categorised by their decay modes, namely alpha decay, beta decay (electrons or positrons), electron capture and/or isomeric transition.

For PET scans, a commonly used radiotracer is fluoro-deoxyglucose ($^{18}$F), commonly referred to as "FDG", which acts as a marker for the tissue uptake of glucose, which in turn is closely correlated with certain types of tissue metabolism. Once the FDG has been administered, it will typically collect in areas of higher chemical activity and so can be used to characterise metabolic activity of different tissues. A PET scanner can be used to form two-dimensional or three-dimensional images (FDG-PET images) of the distribution of FDG within the body. An example of a traditional PET scan is shown in FIG. 1A. Many other radiotracers are known and may be used in place of FDG for similar or different purposes.

PET scans are now commonly performed in conjunction with a computerised tomography (CT) scan. A computerised tomography scan, sometimes referred to as a CAT scan, is a diagnostic imaging procedure which uses x-rays impinging on a subject to produce cross-sectional images, sometimes called slices, of a target region of the subject. The CT images are usually captured at a range of angles about the subject. The cross-sectional slices are then collated to produce a detailed three-dimensional image of the target region of the subject which can be used to identify structural features, for example to diagnose conditions including damage to bones, injuries to internal organs, problems with blood flow, stroke, and cancer. By superimposing PET images with CT scan images (a so-called PET-CT image as shown in FIG. 1B), the anatomical location of a functional feature (e.g. a region of high metabolic activity) may be better determined.

Although the advantages of PET-CT imaging are quite striking, this technique has multiple limitations. Following radionuclide injection, patient activity and speech are usually limited for around 20 minutes to minimise physiologic uptake by muscles and imaging is initiated approximately 60 minutes later. The CT study usually takes approximately 60-70 second to complete, whereas the PET study may take around 30 to 45 minutes, depending on the coverage. As a result, one major limitation is patient motion between the PET and CT imaging studies. Significant motion can prevent proper co-registration and decreases the clinical value of the obtained images.

Additional limitations to PET-CT imaging include the requirement of a radioactive tracer. Radiotracers are expensive to produce and require special facilities, for example a cyclotron. Furthermore, as radiotracers emit a small amount of radiation, there may be a small risk to the subject; if a CT scan is performed in conjunction with a functional imaging scan such as a PET scan then the subject is exposed to even more radiation. As the radiotracer is typically injected into the subject, there is also a risk of local complications associated with the needle insertion for example bleeding, pseudoaneurysms, or leakage into the skin. As some CT scans also require a contrast agent to be administered to the patient, this risk of local complications may be increased when producing PET-CT images. Finally, a small number of patients may be allergic to a radiotracer, or indeed a CT contrast agent.

The present disclosure has been devised in the foregoing context.

SUMMARY

A functional imaging technique is an imaging technique that can be used to identify functional activity within a subject. Positron emission tomography (PET) is an example of such a functional imaging technique, as the radiotracer administered to the subject causes functional features to be readily identifiably on the resulting PET scan, for example regions of high metabolic activity compared to the surrounding region(s), and areas of inflammation. A functional imaging technique may therefore be used to detect or measure changes in physiological activities such as metabolism, blood flow, regional chemical composition, and absorption. A functional feature is a feature that may be identified from such a functional imaging technique, for example the regions of a subject that are visible on a PET scan image (see, for example, FIG. 1A) after a PET radiotracer has been administered to the subject. A functional feature may therefore be considered as a region of functional activity, for example metabolic activity or inflammation.

A structural imaging technique can be understood as an imaging technique that can be used to identify structural features within a subject, for example anatomical location information. Computerised tomography (CT) is an example of such a structural imaging technique. Structural features may be understood to mean features having a distinct intrinsic nature identifiable through image segmentation. For example, a structural feature may comprise a bone or joint, an arterial or venous wall, an outer diameter or inner diameter of a blood vessel and so on. The structural features of at least one blood vessel may include for example the outer wall or outer lumen and/or the inner lumen of the blood vessel. Structural features may be any anatomical or pathological features discernible from a CT scan image.

A CT scan may be performed with or without a contrast agent being administered to the subject. As the radiodensity of blood and the surrounding tissue is similar it can be difficult for the human eye to distinguish the interface between blood vessels and the surrounding tissue on CT images obtained without a contrast agent. The introduction of a contrast agent helps distinguish or "contrast" selected areas of the body from the surrounding tissue. There are numerous types of contrast agents, most of which are iodine based. Contrast agents have a chemical structure such that they limit the ability of x-rays to pass or reflect or refract x-rays.

As used in the present specification and in the appended claims the term "contrast CT image" or "contrast-enhanced CT image" is understood to mean an x-ray image obtained from a CT scan performed on a subject with a contrast agent present within the subject during scanning. Often herein, the term "contrast CT image" and the term "contrast-enhanced CT image" are abbreviated to "CCT image". The term "non-contrast CT image" as used herein is understood to mean an x-ray image obtained from a CT scan performed on a subject in the absence of a contrast agent. Often herein, the term "non-contrast CT image" is abbreviated to "NCT image". In CT scans, the values of voxels are usually given in Hounsfield units, giving the opacity of material to x-rays. It will be understood that in some examples the CT image may be manipulated, but is still considered to be a CT image. For example, in relation to Experiments 1A, 1B and 2 as described herein, the original NCT images were edited to isolate the patient. The use of "CT image" in the appended claims is understood to include such modified CT images.

Sometimes, functional imaging techniques and structural imaging techniques are used in conjunction in order to provide a visualisation of functional and structural features. For example, a PET-CT scan (see, for example, FIG. 1B) combines the functional activity information of a PET scan with the anatomical or pathological information available from a CT scan. However, in order to obtain such PET-CT images, a radiotracer is administered to the subject, which is undesirable for several clinical reasons as described above, for example an increased risk of local complications or allergies.

The present disclosure provides several methods for identifying functional features/functional activity from a CT image. Accordingly, functional features are identified using an imaging paradigm traditionally thought to be useful only for identifying structural features. In particular, automated method for identifying functional features in a CT image based on a radiomic analysis of the CT image are described. Furthermore, methods for training and using classification models, for training and using generative machine learning image segmentation models, and for training and using generative models using a generative adversarial network (GAN) are described.

Advantageously, functional features may be identified without the need for radiotracers or other such agents to be administered to a subject. Furthermore, as the functional features are identified from the CT image, there is no issue with alignment or scale that would arise if one were to superimpose one image showing structural features upon another showing functional features, for example when superimposing a PET scan image on a CT image.

The determined functional features may be indicative of biological activity. For example, the functional features can indicate the presence of cancerous tumours, as will be demonstrated herein.

In some examples, the CT image may be a contrast CT (CCT) image. In some examples, the CT image may be a non-contrast CT (NCT) image. Advantageously, if a NCT image is used, then there is no requirement for a contrast agent to be administered to the subject. The administration of a contrast agent requires the insertion of a needle for injection of the contrast agent into the blood stream. This causes discomfort for the patients and has associated risks such as inadvertent arterial puncture by the needle, and contrast agent leakage outside the veins which can cause skin damage. In addition, the contrast agents can cause renal toxicity and acute kidney injury (contrast induced nephropathy—CIN). The incidence of CIN is as high as 10% after a CT scan obtained with a contrast agent. This is a particular problem in the elderly population who have worse baseline kidney functions, or in patients with declining kidney function/chronic kidney disease. In these patients, there is a small but recognised risk of complete kidney failure induced by CIN, which may lead to renal dialysis. Patients who are allergic to iodine are also unable to have intravenous contrast agents. Accordingly, it is advantageous if information can be learned instead from NCT images.

The target region shown in a CT image may include tissue. The term "target region" as used herein is understood to mean the region of a subject/patient on a CT image that is of medical/clinical interest to the medical practitioner/surgeon, for example a chest cavity, an abdominal cavity or any other region of interest.

As used herein, a "functional image dataset" may be understood to mean image data indicating one or more functional features, the image data derived from an analysis of the subject using a functional imaging technique. A functional image dataset may comprise a visualisation in which functional features are identifiable, or may comprise an array or other data structure indicating pixel values or similar such that an image can be constructed in which functional features are identifiable. For example, a PET scan image is an example of a functional image dataset. A data structure containing information from which a PET scan image may be reconstructed is also an example of a functional image dataset. Another example of a functional image dataset is a Standard Uptake Value (SUV) map/image or an inverted SUV map. A further example of a functional image dataset is a data structure containing information from which a SUV map can be reconstructed.

As used herein, a "simulated functional image dataset" may be understood to mean image data that may indicate one or more functional features, but that has been generated from an input CT image. That is, a "simulated functional image dataset" is not a genuine functional image dataset derived from, for example, a PET scan. A simulated functional image dataset may comprise a visualisation, such as a simulated PET scan image or simulated SUV image. A simulated functional image dataset may comprise a data structure from which a simulated functional image may be reconstructed.

According to an aspect of the invention, a method is provided for identifying one or more functional features in a computed tomography (CT) image. The method comprises providing the CT image to a trained generator model, the generator model trained to translate an input CT image showing a target region of a subject to a simulated functional image dataset each simulated functional image dataset indicating one or more functional features in the target region represented in the input CT image. The method further comprises outputting, from the trained generator model, a simulated functional image dataset corresponding to the provided CT image, the simulated functional image dataset indicating one or more functional features in a target region represented in the provided CT image.

The CT image may be a non-contrast CT (NCT) image. The CT image may be a contrast CT (CCT) image.

The simulated functional image dataset may further indicate structural features in the target region.

The simulated functional image dataset may comprise a visualisation indicating the one or more functional features in the target region represented in the CT image. Advantageously, by providing a visualisation, any functional activity is immediately apparent from the visualisation to the medical practitioner.

The simulated functional image dataset may comprise one of a simulated PET scan image, a simulated PET-CT image, a simulated SUV image, or a simulated inverted SUV image.

The trained generator model may have been trained using a generative adversarial network. For example, the generator model may have been trained using a conditional-GAN or a cycle-GAN.

The trained generator model may comprise a trained image segmentation model. For example, the trained generator model may output a binary visualisation of the target region indicating areas of functional activity.

The one or more functional features may comprise one or more tumours. The method may further comprise sampling, from the simulated functional feature dataset, radiomic feature values for a set of radiomic features. The method may further comprise providing the radiomic feature values to a trained classification model, the classification model trained to take as input a set of radiomic feature values and to output a classification indicating a predicted clinical outcome for the subject having the one or more tumours. The classification model may comprise a regression model, for example a linear regression model. The classification model may comprise a random forest. The predicted clinical outcome may comprise locoregional tumour recurrence, distant metastasis, or death.

The one or more functional features may comprise infected or inflammed tissue. The method may further comprise sampling, from the simulated functional feature dataset, radiomic feature values for a set of radiomic features. The method may further comprise providing the radiomic feature values to a trained classification model, the classification model trained to take as input a set of radiomic feature values and to output a classification indicating a predicted clinical outcome for the subject having the inflammed or infected tissue. The predicted clinical outcome may comprise tissue inflammation or infection.

Advantageously, one may predict a clinical outcome for a subject based on a simulated functional image dataset derived from a received CT image.

According to an aspect of the invention, a method is provided for identifying one or more functional features in a computed tomography (CT) image showing a target region of a subject. The method comprises, for each of a plurality of regions of the CT image, extracting radiomic feature values for a set of radiomic features from the region. The method may further comprise, for each of the plurality of regions of the CT image, providing the radiomic feature values to a trained classification model, the classification model trained to take as input radiomic feature values and to output a classification of a functional activity status. The method may further comprise identifying, from the classifications of the plurality of regions, functional features in the target region of the subject. The trained classification model comprises a trained random forest model.

According to an aspect of the invention, a computer-readable medium is provided. The computer-readable medium has stored thereon computer-readable code representative of a trained generator model or classification model. The computer-readable medium further has stored thereon instructions which, when executed by one or more processors, cause the one or more processors to implement a method as described herein to identify one or more functional features in a computed tomography (CT) image.

According to an aspect of the invention, a computing apparatus is provided for identifying functional features in a computed tomography (CT) image. The apparatus comprises one or more memory units. The apparatus further comprises one or more processors configured to execute instructions stored in the one or more memory units to perform a method as described herein to identify one or more functional features in a computed tomography (CT) image.

According to an aspect of the invention, a method is provided for training a generative adversarial network (GAN) to generate a simulated functional image dataset from a computed tomography (CT) image, the GAN comprising a generator network and a discriminator network. The method comprises receiving a training set comprising: a plurality of CT images, each CT image showing a target region of a subject; and a plurality of functional image datasets, each functional image dataset indicating functional features in a target region of a subject. The method further comprises training the GAN, wherein training the GAN comprises: training the generator network, using the plurality of CT images and feedback from the discriminator network, to generate simulated functional image datasets; and training the discriminator network, using the generated simulated functional image datasets and the plurality of functional image datasets, to classify received image datasets as simulated functional image datasets or genuine functional image datasets, and to provide feedback to the generator network. The method further comprises outputting a trained generator model to translate an input CT image to a simulated functional image dataset indicating one or more functional features in the target region shown in the input CT image. The GAN may comprise a conditional-GAN or a cycle-GAN.

The plurality of functional image datasets may comprise a plurality of PET scan images, PET-CT scan images, SUV images, or inverted SUV images and the trained generator model may be to translate an input CT image to a simulated PET scan image, simulated PET-CT scan image, simulated SUV image or simulated inverted SUV image.

According to an aspect of the invention, a method is provided for training a machine learning image segmentation algorithm or machine learning classification algorithm to identify functional features from a computed tomography (CT) image. The method comprises receiving a labelled training set for the image segmentation algorithm or classification algorithm, the labelled training set comprising: a plurality of CT images, each CT image of the plurality of CT images representative of a target region of a subject; and a corresponding plurality of functional feature identifiers, each functional feature identifier labelling at least one functional feature in a corresponding CT image of the plurality of CT images; wherein each functional feature identifier is generated from a functional image dataset, each functional image dataset indicating one or more functional features in the target region represented in the CT image to which the functional feature identifier corresponds. The method further comprises training a machine learning image segmentation algorithm or classification algorithm, using the plurality of CT images and the corresponding plurality of functional feature identifiers, to learn features of the CT images that correspond to functional features labelled by the functional feature identifiers, and output a trained image segmentation model or classification model. The method further comprises outputting the trained image segmentation model or classification model usable for identifying a functional feature in a CT image.

A machine learning image segmentation algorithm may comprise a neural network.

Training a classification algorithm may comprise: extracting, from each CT image, radiomic feature values for a set of radiomic features; training a classification algorithm, using the extracted radiomic feature values of each CT image and the corresponding functional feature identifier to learn features of the CT images that correspond to functional features identified by the functional feature identifiers, and output a trained classification model. The classification algorithm may comprise a random forest classification algorithm.

Each functional feature identifier may comprise a segmentation mask. Each segmentation mask of the plurality of segmentation masks may comprise a binary segmentation mask.

Each CT image may comprise a non-contrast CT (NCT) image. Each CT image may comprise a contrast CT (CCT) image. Each CT image may comprise a two-dimensional image. Each CT image may comprise a three-dimensional volume image.

Each functional image dataset may comprise a radionuclide image dataset.

Each radionuclide image dataset may comprise positron emission tomography (PET) scan image data. Each functional image dataset may comprise an SUV image or inverted SUV image.

The at least one functional feature may be representative of the avidity of imaging tracer uptake by tissue.

According to an aspect of the invention, a computer-readable medium is provided. The computer-readable medium has stored thereon instructions which, when executed by one or more processors, cause the one or more processors to implement a method for training a GAN, for training a machine learning image segmentation algorithm, or for training a machine learning classification algorithm as described herein.

According to an aspect of the invention, a computing apparatus for training a GAN, for training a machine learning image segmentation algorithm, or for training a machine learning classification algorithm is provided. The apparatus comprises one or more memory units. The apparatus further comprises one or more processors configured to execute instructions stored in the one or more memory units to perform a method for training a GAN, for training a machine learning image segmentation algorithm, or for training a machine learning classification algorithm as described herein.

According to an aspect of the invention, a method is provided for establishing a labelled training set for training a machine learning image segmentation algorithm or machine learning classification algorithm to identify functional features in a computed tomography (CT) image. The method comprises receiving a plurality of CT images, each CT image showing a target region of a subject. The method further comprises receiving a plurality of functional image datasets, each functional image dataset indicating functional features in a target region represented in one or more CT images of the plurality of CT images. The method further comprises mapping each functional image dataset to the one or more CT images showing the target region comprising functional activity. The method further comprises generating, for each CT image, a corresponding functional feature identifier using the plurality of mapped functional image datasets, each functional feature identifier labelling one or more functional features in the target region shown in the corresponding CT image. The labelled training set includes pairs of CT images and functional feature identifiers, each pair comprising a CT image and a corresponding functional feature identifier.

Each functional image dataset may comprise a radionuclide image dataset. Each radionuclide image dataset may comprise positron emission tomography (PET) scan image data. Each functional image dataset may comprise a standard uptake value (SUV) map.

Each CT image may comprise a non-contrast CT (NCT) image. Each CT image may comprise a contrast CT (CCT) image.

Each functional feature identifier may comprise a segmentation mask. A segmentation mask as used herein may be understood to mean a labelling of pixels/voxels in at least one region of a corresponding CT image, such that pixels/voxels with the same label share characteristics, and may be mappable back to features in the target region shown in the scan. For example, regions of functional activity in a CT image may be labelled or tagged in some way identifiable to a computer processor. The data concerning the labelling or tagging may be referred to as a segmentation mask.

Generating a functional feature identifier may comprise identifying, within the target region of the CT image, radiomic features representative of the functional activity, and comparing the identified radiomic features with threshold values to identify the area of functional activity within the target region of the CT image.

According to an aspect of the invention, a labelled training set is provided, the labelled training set established according to a method as described herein.

According to an aspect of the invention, a computer-readable medium is provided. The computer-readable medium has instructions stored thereon which, when executed by one or more processors, cause the one or more processors to implement a method as described herein to establish a training set.

According to an aspect of the invention, a method of identifying structural features and functional features from a computed tomography (CT) image is provided. The CT image identifies one or more structural features in a target region of a subject. The method comprises comparing radiomic feature values of a target region shown in the CT image with corresponding threshold values. The method further comprises determining, from the comparison, functional features within the target region. The method further comprises generating, using the determined functional features, a visualisation of the target region identifying the functional features and the structural features.

Advantageously, functional features and structural features may both be seen and visualised from an input CT image, enabling a medical practitioner to easily identify functional activity in the target region of the subject without the need for the patient to be injected with any radiotracers, and without the difficulties inherent in aligning PET images and CT images.

In some examples, the CT image may be a contrast CT (CCT) image. In some examples, the CT image may be a non-contrast CT (NCT) image.

Comparing radiomic feature values with corresponding thresholds may comprise checking for at least a 10-fold difference between the radiomic feature values and the threshold values. Comparing radiomic features with corresponding thresholds may comprise checking for at least a 20-fold difference between the radiomic features and the threshold values.

The compared radiomic features may include one or more of:

wavelet-HHL_glszm_SmallAreaEmphasis;
    wavelet-HHL_glszm_SmallAreaLowGrayLevelEmpha-
      sis;
    wavelet-LHH_glszm_SmallAreaEmphasis;
    wavelet-LHH_glszm_SmallAreaHighGrayLevelEmpha-
      sis;
    wavelet-LHH_glszm_SmallAreaLowGrayLevelEmpha-
      sis; and
    wavelet-LHH_glszm_SmallAreaHighGrayLevelEmpha-
      sis.

The visualisation may comprise a simulated/pseudo-PET scan or simulated/pseudo-PET-CT scan.

The target region may include tissue. The term "target region" as used herein is understood to mean the region of a subject/patient on a CT image that is of medical/clinical interest to the medical practitioner/surgeon, for example a chest cavity, an abdominal cavity or any other region of interest.

The determined functional features may be indicative of biological or pathological activity.

The method may further comprise generating a functional feature identifier corresponding to the determined functional features. The functional feature identifier may comprise a segmentation mask. The functional feature identifier may be used as part of a training set for training a machine learning image segmentation algorithm to identify functional features from CT images.

According to an aspect of the invention, a computer-readable medium is provided having instructions stored thereon which, when executed by one or more processors, cause the one or more processors to implement a method for identifying structural and functional features from a CT image according to any preceding claim.

According to an aspect of the invention, a computing apparatus is provided for identifying functional features from a CT image. The apparatus comprises one or more memory units and one or more processors configured to execute instructions stored in the one or more memory units to perform a method of identifying structural features and functional features from a computed tomography image as described herein.

According to an aspect of the invention, a computer-readable medium is provided for identifying functional features in a CT image, the computer-readable medium having stored thereon a visualisation generated using a method as described herein.

The computer program and/or the code for performing such methods as described herein may be provided to an apparatus, such as a computer, on the computer readable medium or computer program product. The computer readable medium could be, for example, an electronic, magnetic, optical, electromagnetic, infrared, or semiconductor system, or a propagation medium for data transmission, for example for downloading the code over the Internet. Alternatively, the computer readable medium could take the form of a physical computer readable medium such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

Many modifications and other embodiments of the inventions set out herein will come to mind to a person skilled in the art to which these inventions pertain in light of the teachings presented herein. Therefore, it will be understood that the disclosure herein is not to be limited to the specific embodiments disclosed herein. Moreover, although the description provided herein provides example embodiments in the context of certain combinations of elements, steps and/or functions may be provided by alternative embodiments without departing from the scope of the invention.

BRIEF DESCRIPTION OF THE DRAWINGS

Embodiments of the invention will now be described, by way of example only, with reference to the accompanying drawings in which like reference numerals are used to depict like parts. In the drawings:

FIG. 4A shows a representation of a heart and identifies the myocardium and ventricle;

FIG. 4B shows a comparison between the myocardium and ventricle of radiomic feature values determined from CT scan data;

FIG. 8A shows a representation of a liver, and particularly highlights "outer" and "inner" regions;

FIG. 8B shows a comparison between the outer liver region and inner liver region of radiomic feature values determined from CT scan data;

FIGS. 9A-9C show non-contrast CT scan images of lymph nodes (LN1, LN2, LN3) that have been found to be FDG-positive in a separate PET scan;

FIGS. 9D-9F show non-contrast CT scan images of lymph nodes (LN4, LN5, LN6) that have been found to be FDG-negative in a separate PET scan;

FIGS. 10A-10C depict spherical subsamples of the CT image data that was analysed for the lymph nodes of FIGS. 9A-9C respectively;

FIGS. 10D-10F depict spherical subsamples of the CT image data that was analysed for the lymph nodes of FIGS. 9D-9F respectively;

FIG. 12A shows comparisons between various pairs of the lymph nodes of FIGS. 9A-9F of the radiomic feature values determined from the CT scan data for which there was a 10-fold or greater difference;

FIG. 12B shows comparisons between various pairs of the lymph nodes of FIGS. 9A-9F of the radiomic feature values determined from the CT scan data for which there was a 2-fold or smaller difference;

FIG. 15 shows a table of radiomic features that are deemed relevant to identifying metabolic activity in PET scans of lymph nodes;

FIGS. 18A, 18B, and 18C respectively show an NCT image, a FDG-PET scan image, and a simulated/pseudo-FDG-PET-CT scan image of the lymph node LN2;

FIGS. 20A, 20B, and 20C respectively show an NCT image, a FDG-PET scan image, and a simulated/pseudo-FDG-PET-CT scan image of the lymph node LN4;

FIGS. 21A, 21B, and 21C respectively show an NCT image, a FDG-PET scan image, and a simulated/pseudo-FDG-PET-CT scan image of the lymph node LN5;

FIGS. 22A, 22B, and 22C respectively show an NCT image, a FDG-PET scan image, and a simulated/pseudo-FDG-PET-CT scan image of the lymph node LN6;

FIG. 39 shows a flowchart of a method for training a classification algorithm to identify functional features from a CT image;

FIG. 40 shows a flowchart of a method of identifying one or more functional features in a CT image using a trained classification model;

DETAILED DESCRIPTION

Figure 1B:
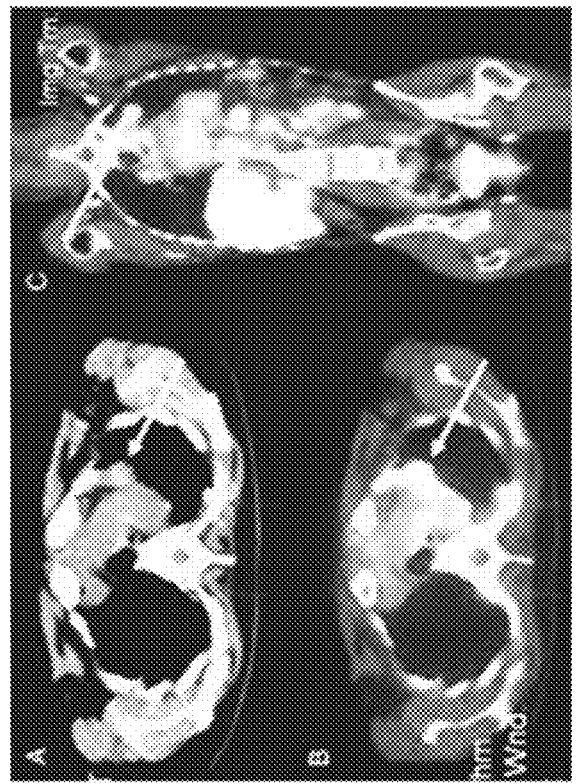
FIG. 1B shows a typical PET-CT scan image.
Figure 1A:
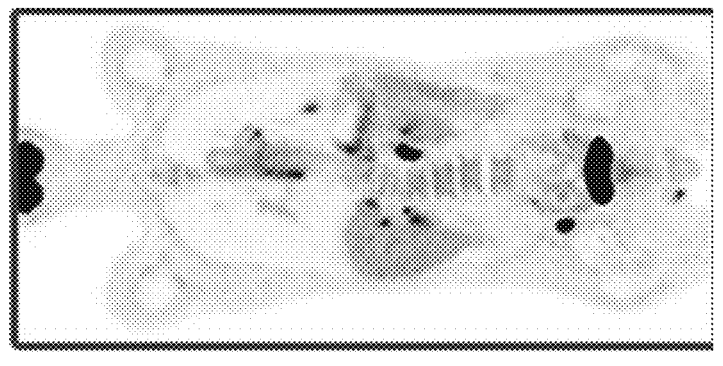
FIG. 1A shows a typical positron emission tomography (PET) scan image.

The present disclosure is concerned with improved methods and apparatus for identifying functional features in medical imaging. Whilst various embodiments are described below, the invention is not limited to these embodiments, and variations of these embodiments may well fall within the scope of the invention which is to be limited only by the claims.

As will be appreciated by one skilled in the art, the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in any one or more computer-readable medium/media having computer usable program code embodied thereon.

Any combination of one or more computer-readable medium/media may be utilized. The computer-readable medium may be a computer-readable signal medium or a computer-readable storage medium. A computer-readable storage medium may be, for example, but not limited to, an electronic, magnetic, optical, electromagnetic, infrared, or semiconductor system, apparatus, device, or any suitable combination of the foregoing. More specific examples of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fibre, a portable compact disc read-only memory (CDROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in a baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

Computer code embodied on a computer-readable medium may be transmitted using any appropriate medium, including but not limited to wireless, wireline, optical fibre cable, radio frequency (RF), etc., or any suitable combination thereof.

Computer program code for carrying out operations for aspects of the present invention may be written in any combination of one or more programming languages, including an object oriented programming language such as Java™, C++, or the like, and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects and embodiments of the present invention are described below with reference to flowchart illustrations and/or block diagrams of methods, apparatus (systems) and computer program products according to illustrative examples. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computing device, other programmable data processing apparatus, or other devices to function in a particular manner, such that the instructions stored in the computer-readable medium produce an article of manufacture including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus, or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The illustrative examples described herein may be utilized in many different types of data processing environments including a distributed data processing environment, a single data processing device, or the like.

The inventors have recognised that CT images obtained, with or without the administration of a contrast agent, have enough information embedded within them to be able to identify functional activity, for example regions of high metabolic rate, which can be used to detect for example cancer metastasis.

As will be discussed below, FIGS. 2A-35 demonstrate that a routine CT scan contains information to enable characterisation of FDG uptake in tissue. Furthermore, it will be demonstrated that it is feasible to generate a visualisation indicating functional features (a simulated/pseudo-PET-CT scan, or more particularly a simulated/pseudo-FDG-PET-CT scan) without the use of FDG. While the discussion below in relation to FIGS. 2A-35 concerns FDG PET scans, the skilled person would appreciate that other functional imaging modalities may be involved in other embodiments, for example PET scans using other radiotracers.

Figure 2B:
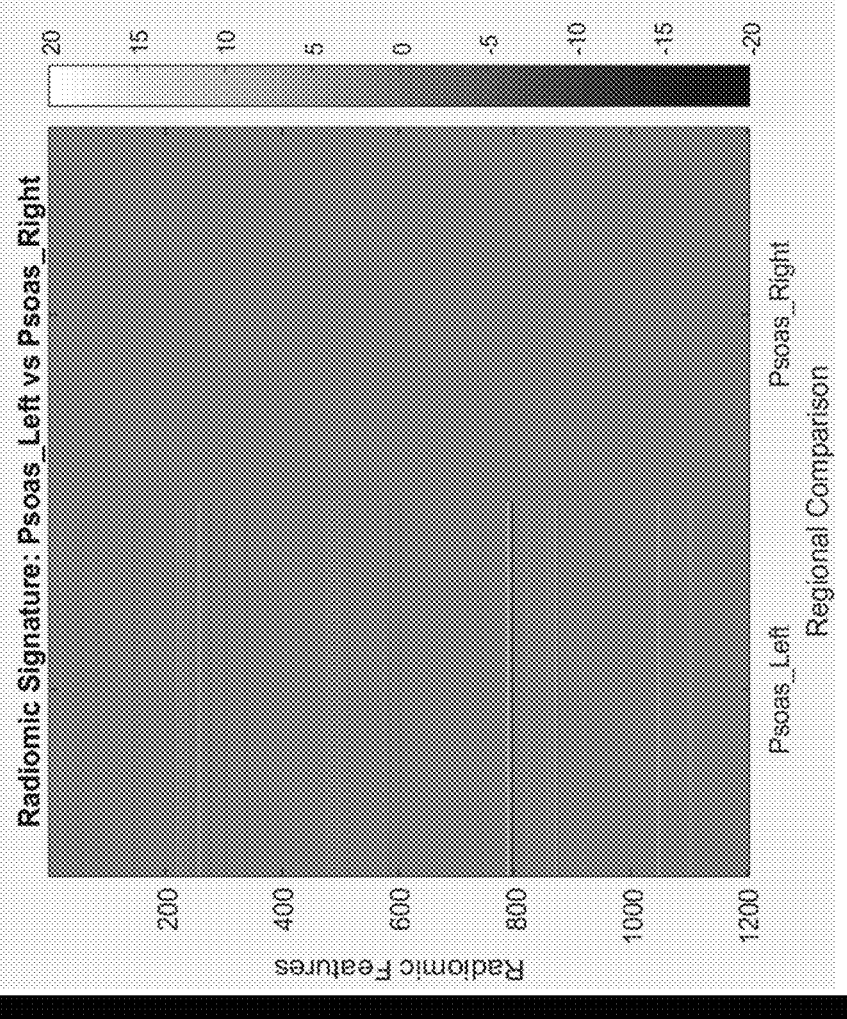
FIG. 2B shows, for 1200 radiomic features, a comparison between the left and right psoas muscles of the radiomic feature values determined from CT scan data.
Figure 2A:
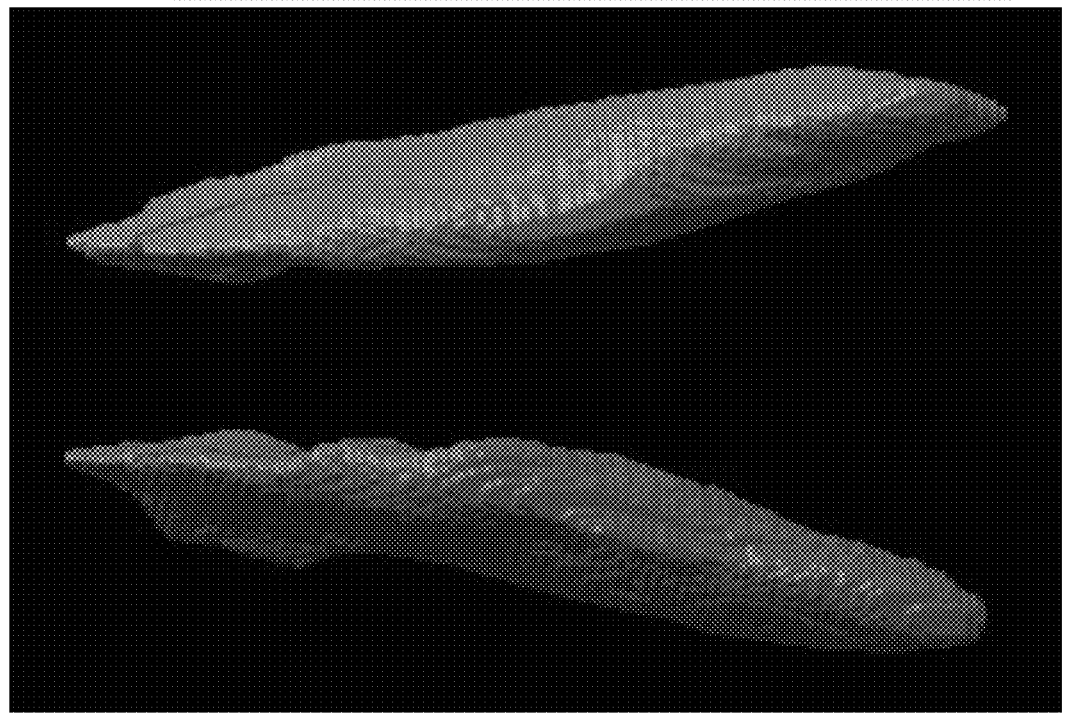
FIG. 2A shows a representation of left and right psoas muscles.

FIG. 2A shows the left and right psoas muscles as segmented from CT image data. The regions delimiting the left/right psoas muscle were manually annotated on serial axial CT slices. The 2D segmentations were then visualized in 3D as seen in FIG. 2A. The psoas major is a long fusiform muscle located in the lateral lumbar regions between the vertebral column and the brim of the lesser pelvis. It joins the iliacus muscle to form the iliopsoas and is a skeletal muscle that can be easily identified in a routine CT scan. The psoas muscles are skeletal muscles that do not typically demonstrate much functional activity at rest that would show up in a PET scan and so can be useful for establishing a baseline against which one is able to verify that a radiomic analysis of a CT scan can be used to identify functional activity such as metabolism.

Radiomics is a method that extracts large amount of features from radiographic medical images using data-characterisation algorithms. A radiomic analysis of 1200 radiomic features was performed on a target region of a CT image showing a left psoas muscle and on a target region of a CT image showing a right psoas muscle. A comparison of the radiomic feature values of the left and right psoas muscles is shown in FIG. 2B. In particular, the radiomic features of the right psoas muscle were taken as the normal against which the corresponding radiomic features of the left psoas muscle were compared, and FIG. 2B indicates whether there is a difference between a radiomic feature value for the left psoas muscle and the corresponding radiomic feature for the right psoas muscle. In particular, FIG. 2B shows a radiomic feature comparison of the two psoas muscles on a heat map scale. As demonstrated in FIG. 2B, a radiomic feature comparison of the left and right psoas muscles shows little difference between the two.

Figures 3A, 3B:
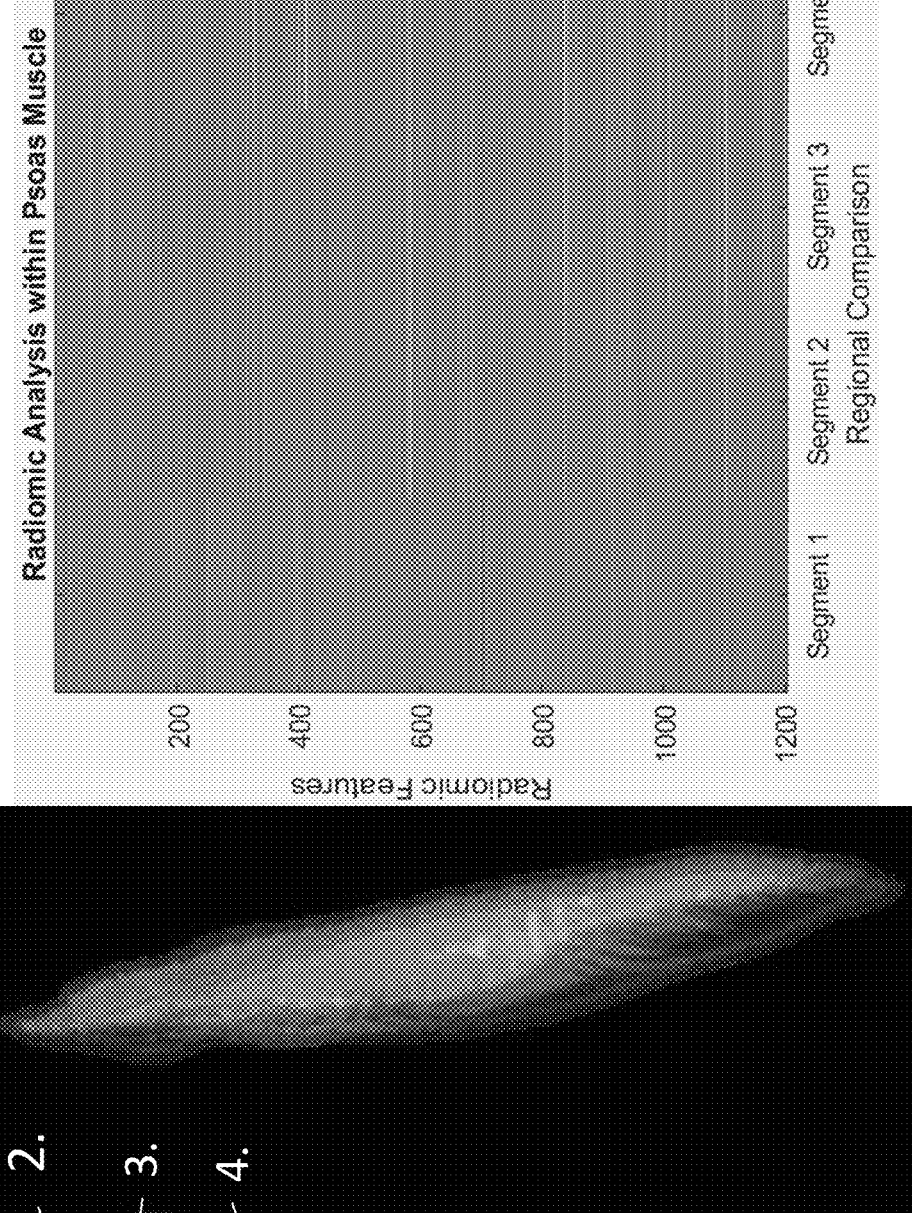
FIG. 3A shows a representation of left and right psoas muscles with subregions/segments identified.
FIG. 3B shows a comparison of radiomic feature values for the segments identified in FIG. 3A.

Having verified that there is little difference between left and right psoas muscles, concentric regions/segments of the left psoas muscle were analysed. The concentric regions 1-4 are indicated in FIG. 3A. The radiomic features of each segment were sampled and compared with the entire left psoas muscle baseline. The rationale was to show that subregions within the psoas muscle are similar to the overall psoas signature. As shown in FIG. 3B, once again there was little difference between the radiomic features for each segment. As the psoas muscle is not a muscle with a high metabolic rate, FIG. 3B indicates that the psoas muscle provides for a fairly uniform set of radiomic features. This held true also when comparing against the right Psoas muscle.

After a radiomic analysis of the right and left psoas muscles was performed, which indicate that there is little difference between some tissues that are not greatly metabolically active, a radiomic analysis was performed on a CT image of a heart. Heart muscle (myocardium) is highly active metabolically. Firstly, a comparison was made between image regions of the myocardium and ventricle (as indicated in FIG. 4A, in which the myocardium is labelled with a 1 and heart chambers are labelled with a 2). The heart chambers are cavities within the heart filled with blood and some fibrous tissue (papillae), whereas the myocardium is the muscular tissue of the heart. Blood and fibrous tissue are not metabolically active, whereas myocardium is. Accordingly, one would expect to see a difference in a comparison of the radiomic feature values of the myocardium and the heart chambers. FIG. 4B shows that this is the case and further demonstrates that radiomic features can be used to determine the myocardium and the heart chambers. In FIG. 4B the radiomic features for the heart chambers were taken as the normal/control against which the corresponding features of the myocardium were compared. As can be seen, many of the radiomic features differ greatly between the myocardium and the heart chambers.

Figure 5B:
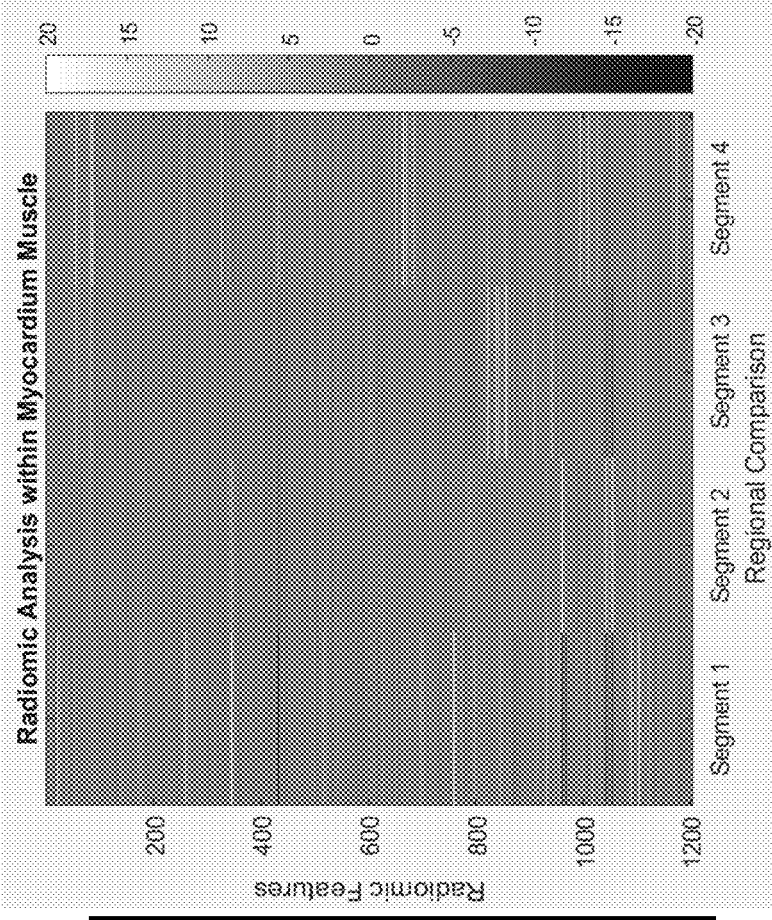
FIG. 5B shows a comparison of radiomic features for the segments identified in FIG. 5A.
Figure 5A:
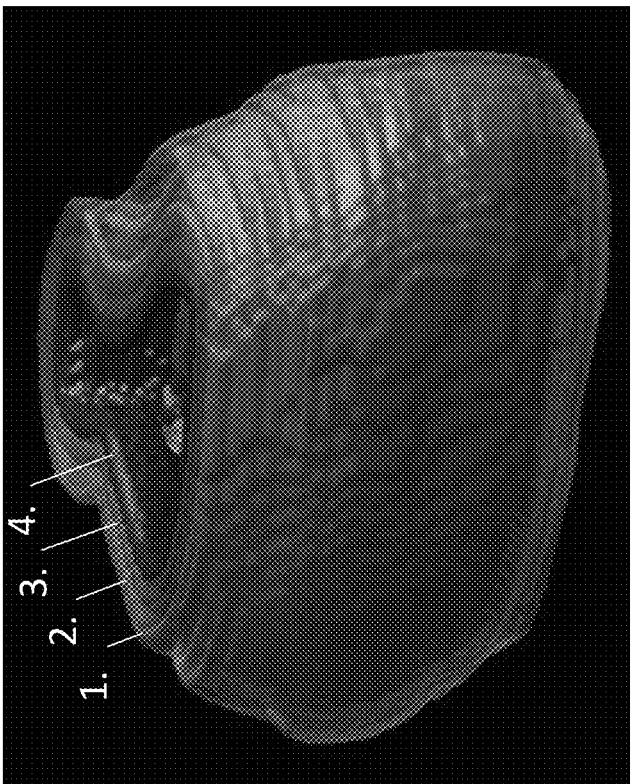
FIG. 5A shows a representation of a heart and indicates four subregions.

As with the psoas muscles, radiomic features were sampled for several sub-regions of the myocardium, labelled 1-4 in FIG. 5A. FIG. 5B shows a comparison of the radiomic features for each of these sub-regions, and indicates that there are minimal differences in the radiomic features from location to location within the myocardium. That is, within different regions of the highlighted metabolic muscle (myocardium), no difference is observed in radiomic features.

Figure 6B:
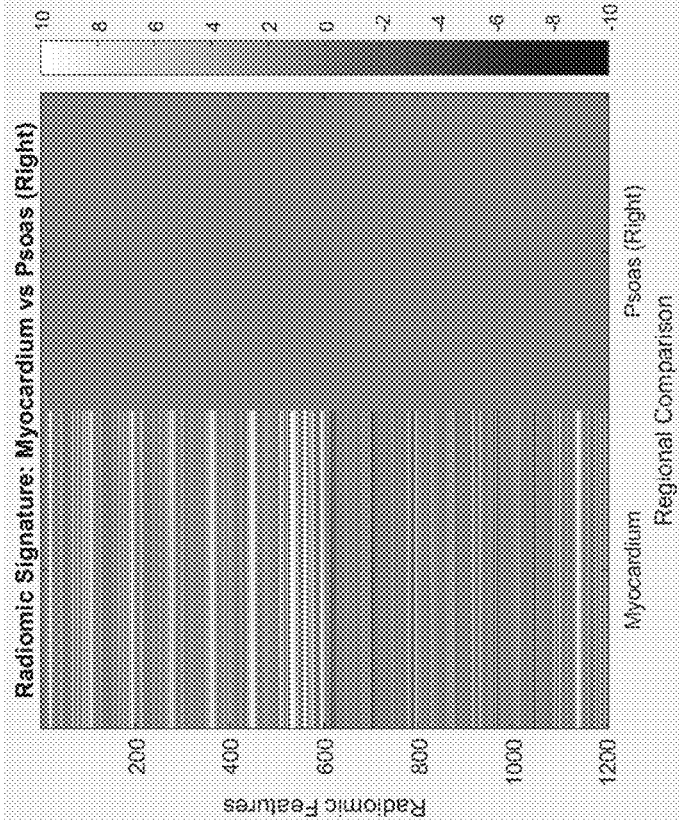
FIG. 6B shows a comparison between the myocardium and right psoas of radiomic feature values determined from CT scan data.
Figure 6A:
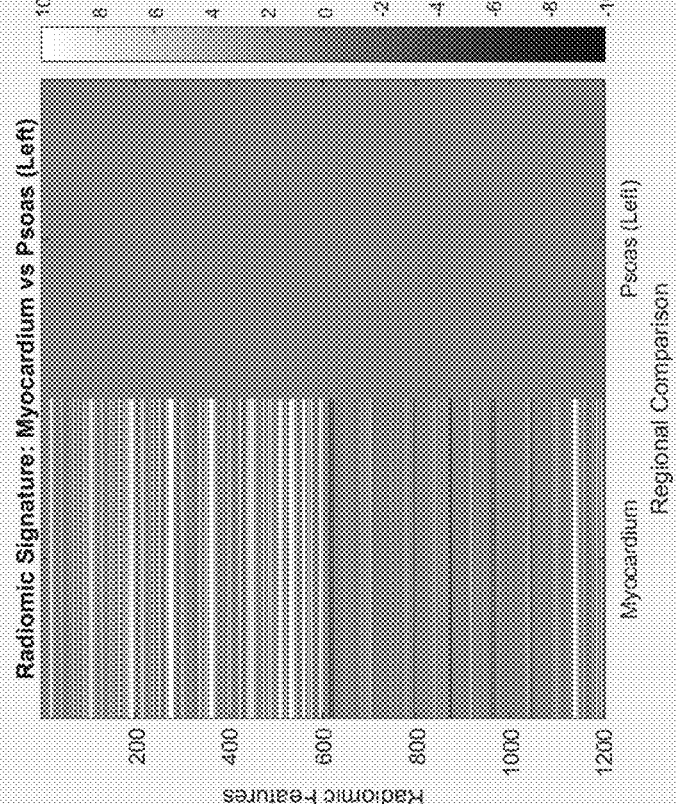
FIG. 6A shows a comparison between the myocardium and left psoas of radiomic feature values determined from CT scan data.
Figure 6C:
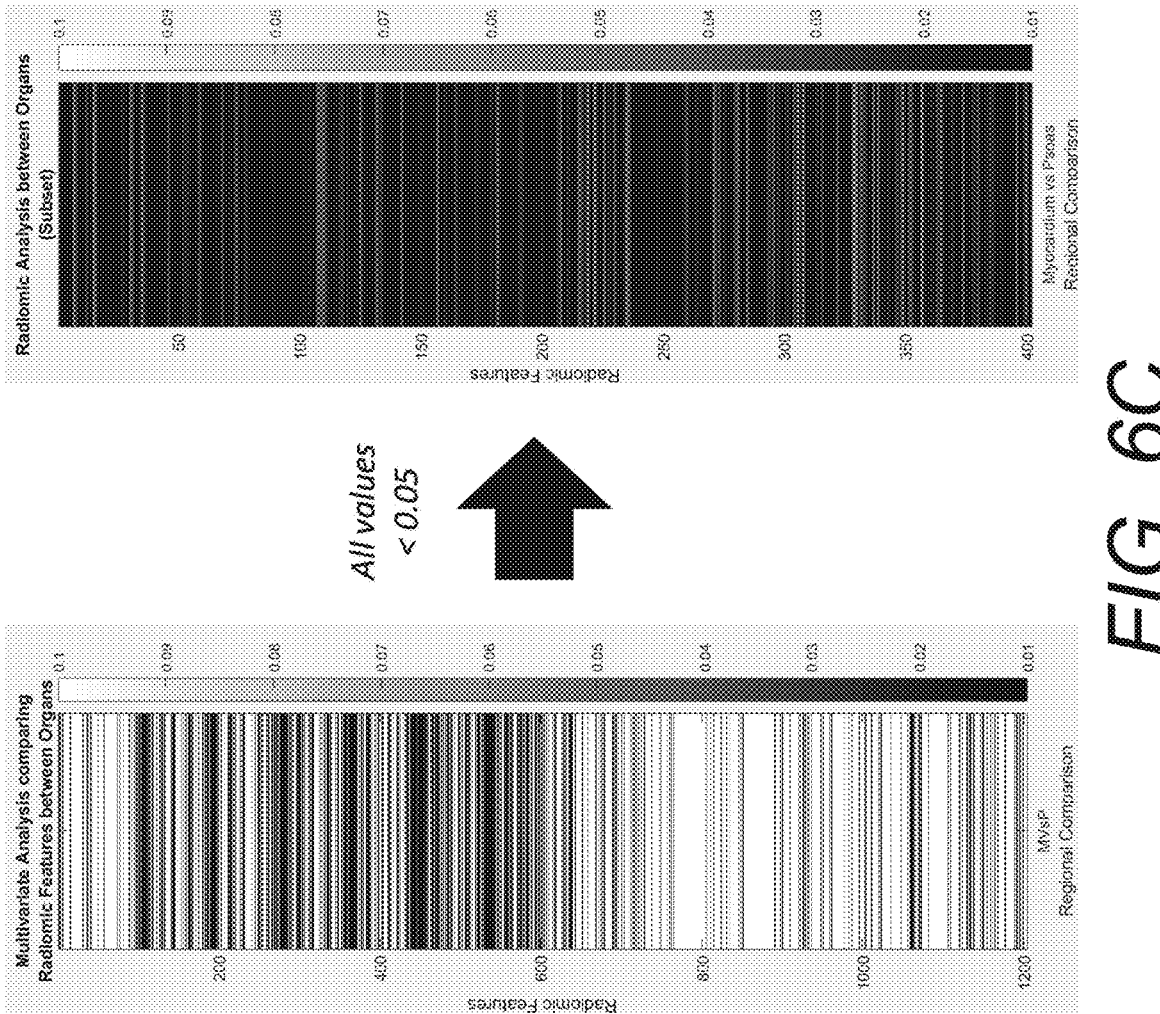
FIG. 6C shows the results of a statistical analysis comparing radiomic signatures of the myocardium and psoas muscles.

FIGS. 6A and 6B show a comparison of the radiomic features for the (metabolically active) myocardium with the radiomic features for the (metabolically inactive) left and right psoas respectively. In both figures the features of the relevant psoas muscle were taken as the control against which the radiomic features of the myocardium were compared. As indicated in the figures, there is a large difference across many features between the myocardium and the psoas muscles. The scale of FIGS. 6A and 6B ranges between a +10-fold difference and a −10-fold difference. A statistical analysis (t-test) was performed to compare the radiomic signatures between the myocardium and psoas muscles (shown in FIG. 6C). The analysis established that of the 1200 radiomic features compared, there were approximately 400 that were statistically different ($p<0.05$) between the myocardium and the psoas. It is hypothesised that the differences in value for a subset/combination of these radiomic features are underpinned by the difference in metabolic activity.

Figure 7A:
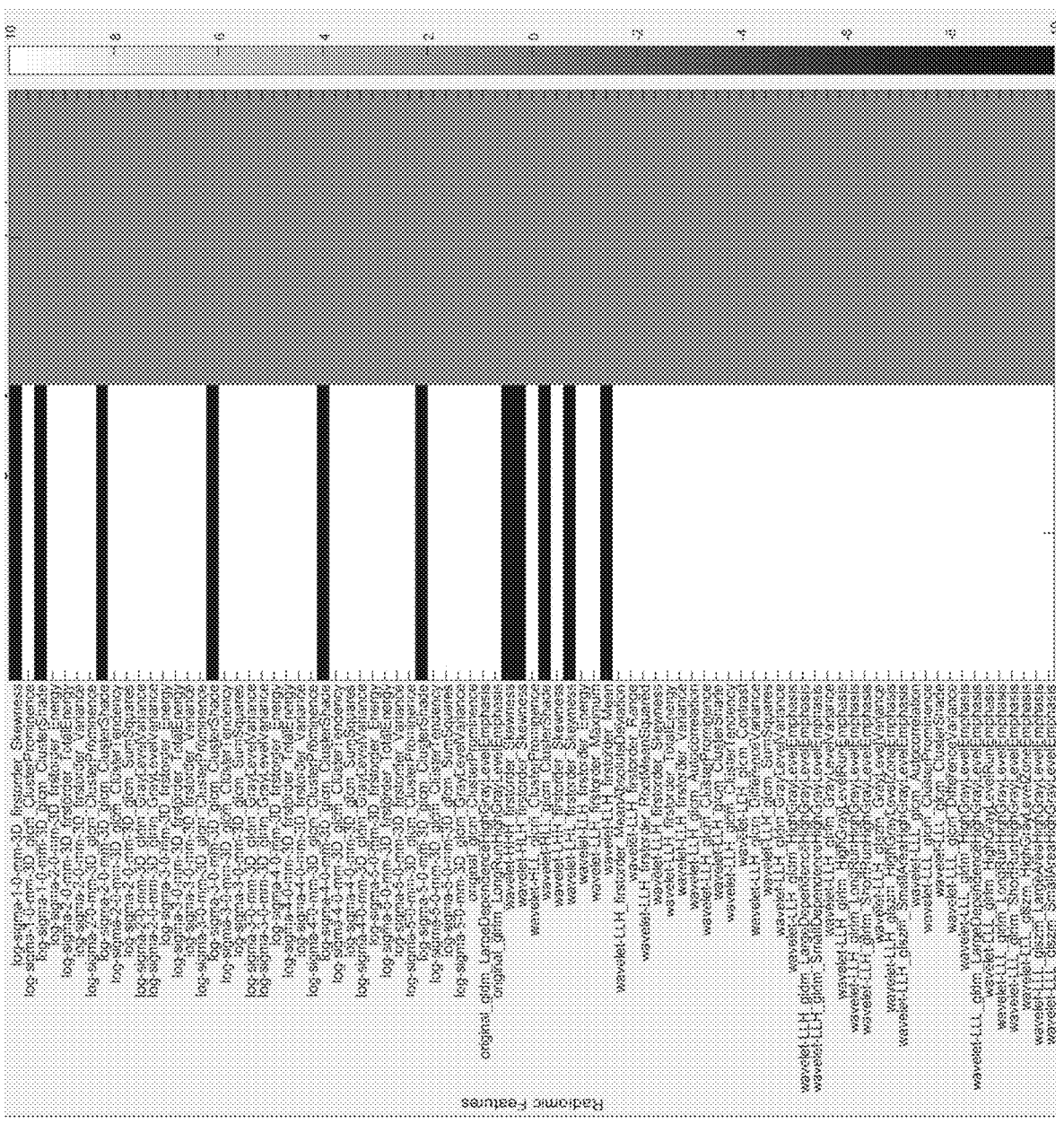
FIGS. 7A and 7B show the radiomic features with a 10-fold or greater difference in value between the myocardium and the left and right psoas muscles respectively.
Figure 7B:
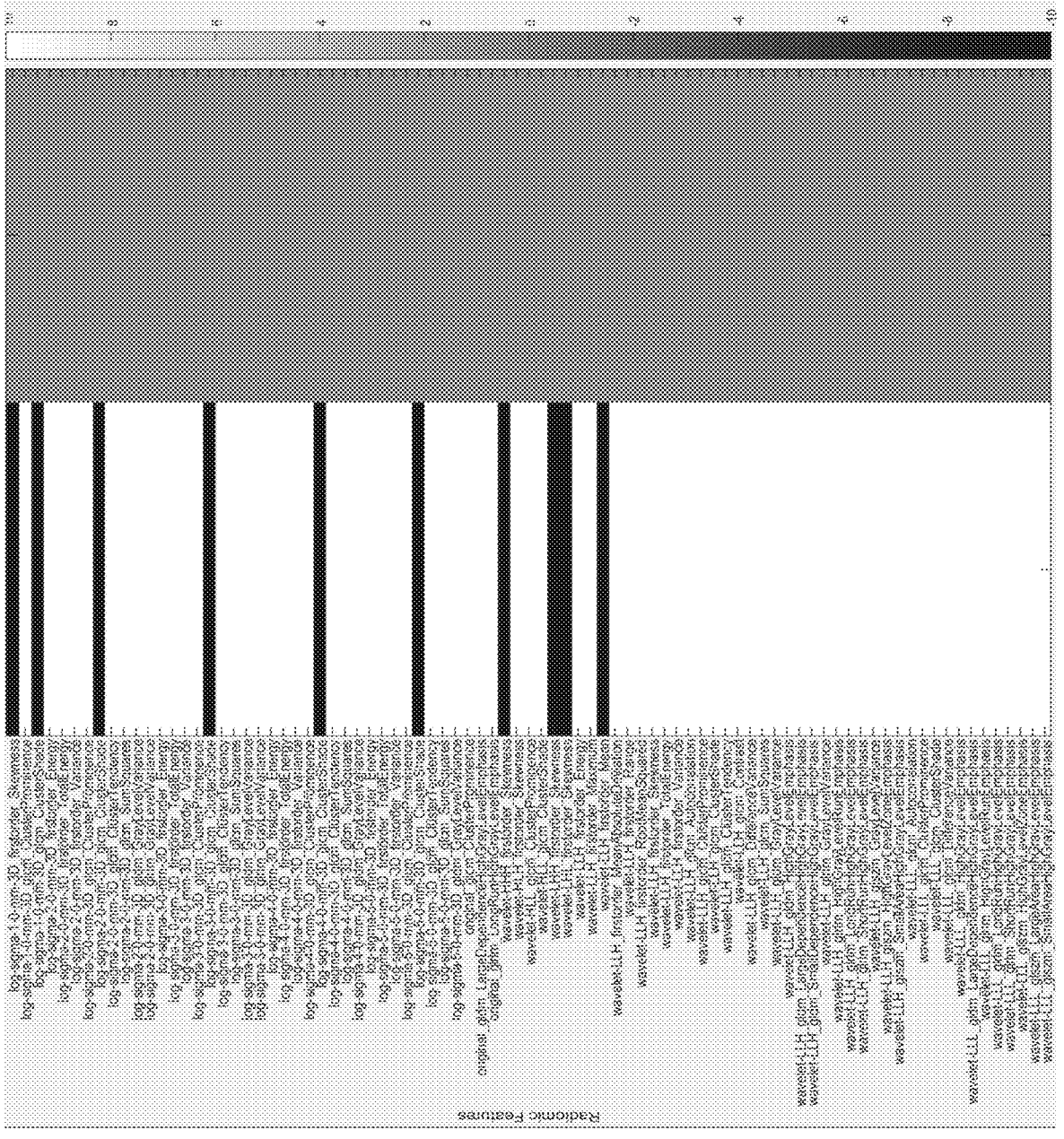
Figure 7C:
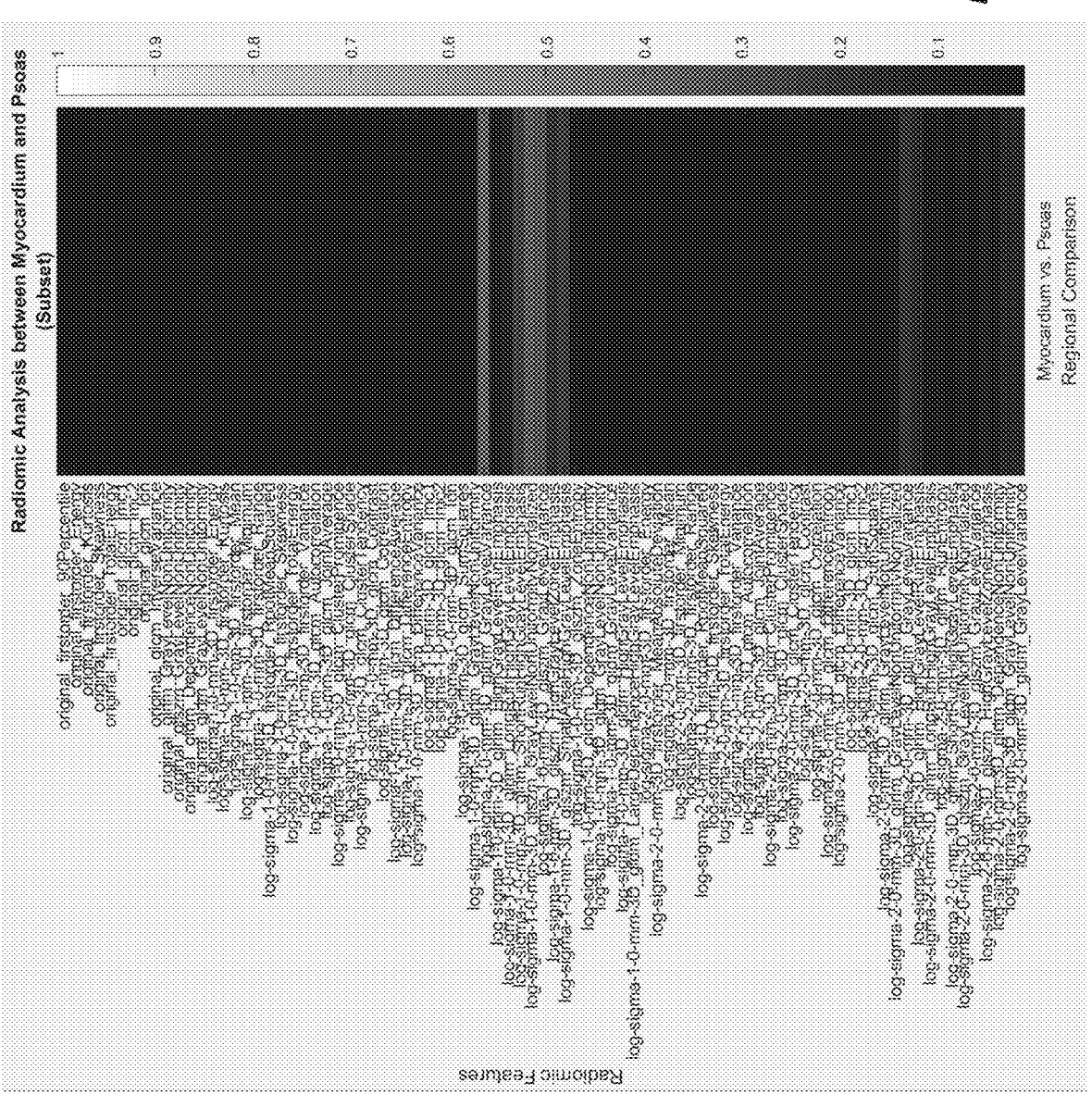
FIG. 7C shows the results of a statistical analysis comparing the radiomic values with 10-fold difference between the myocardium and psoas muscles.

FIGS. 7A and 7B show the radiomic features that, for the myocardium, were identified as having a greater than 10-fold difference when compared with the corresponding radiomic feature values for the left and right psoas respectively. A statistical analysis (t-test) was performed comparing the radiomic values with 10-fold difference between the myocardium and psoas muscles. Of the 1200 radiomic features analysed, 85 features were found to have a greater than 10-fold difference between myocardium and psoas muscle. (see FIG. 7C) and statistically significant ($p<0.05$).

A similar radiomic analysis was performed on CT image data having a target region including the liver. The liver is the most metabolically active organ in the human body.

The inner segment of liver comprises the portal circulation system and bile ducts, which are less metabolically active than the liver parenchyma. Accordingly radiomic feature values were determined for an outer region and an inner region as shown in FIG. 8A. The outer region (parenchyma) is denoted with a "1" and the inner region (portal circulation system and bile ducts) is labelled with a "2" in FIG. 8A. FIG. 8B shows a comparison of the radiomic feature values for the outer region with the corresponding radiomic feature values for the inner region. FIG. 8B demonstrates that it is possible to distinguish between the outer region and inner region of the liver from a CT scan by radiomic analysis.

Figure 8C:
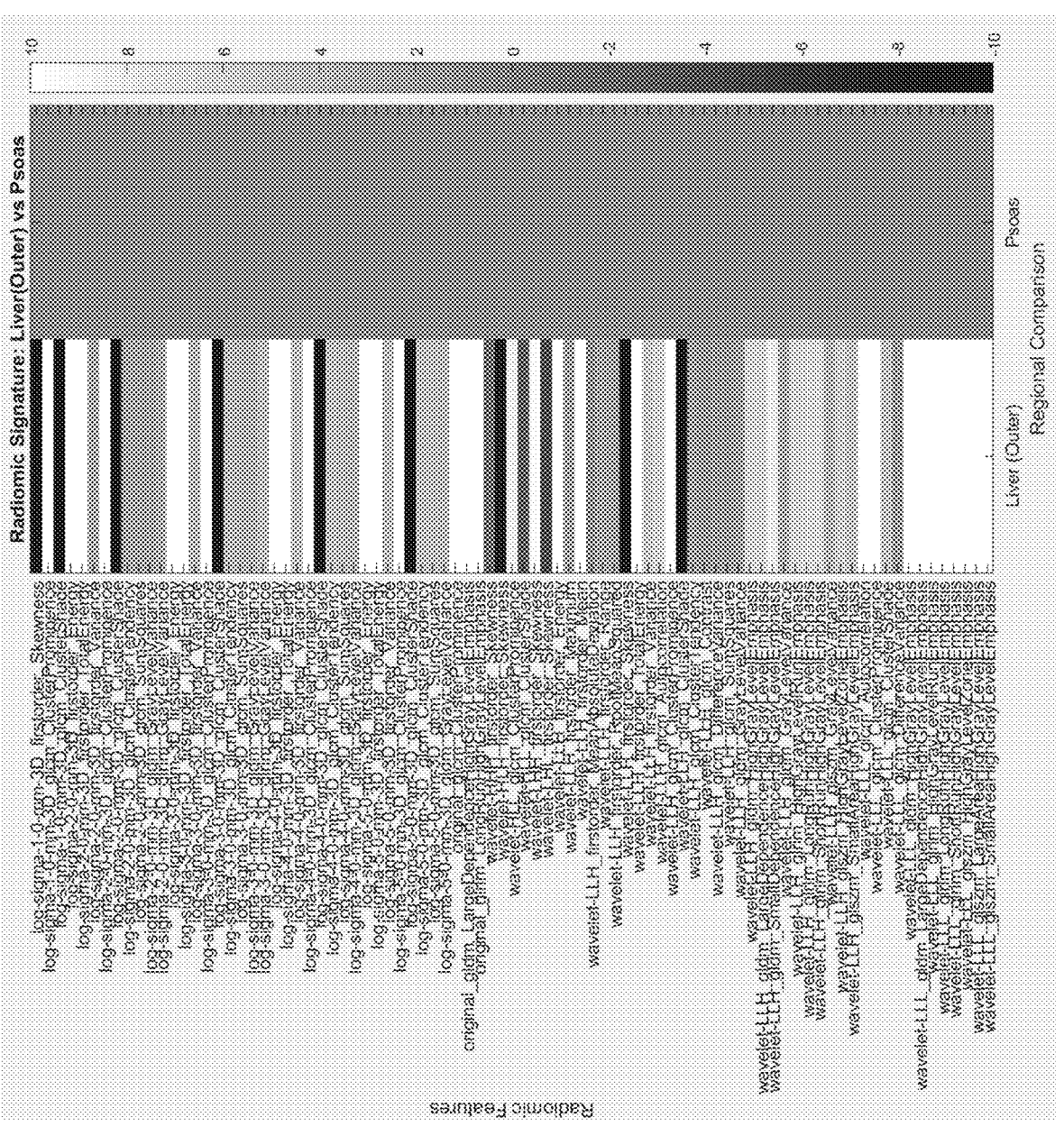
FIG. 8C shows a comparison between the outer liver region and psoas muscle of radiomic feature values determined from CT scan data.
Figure 8D:
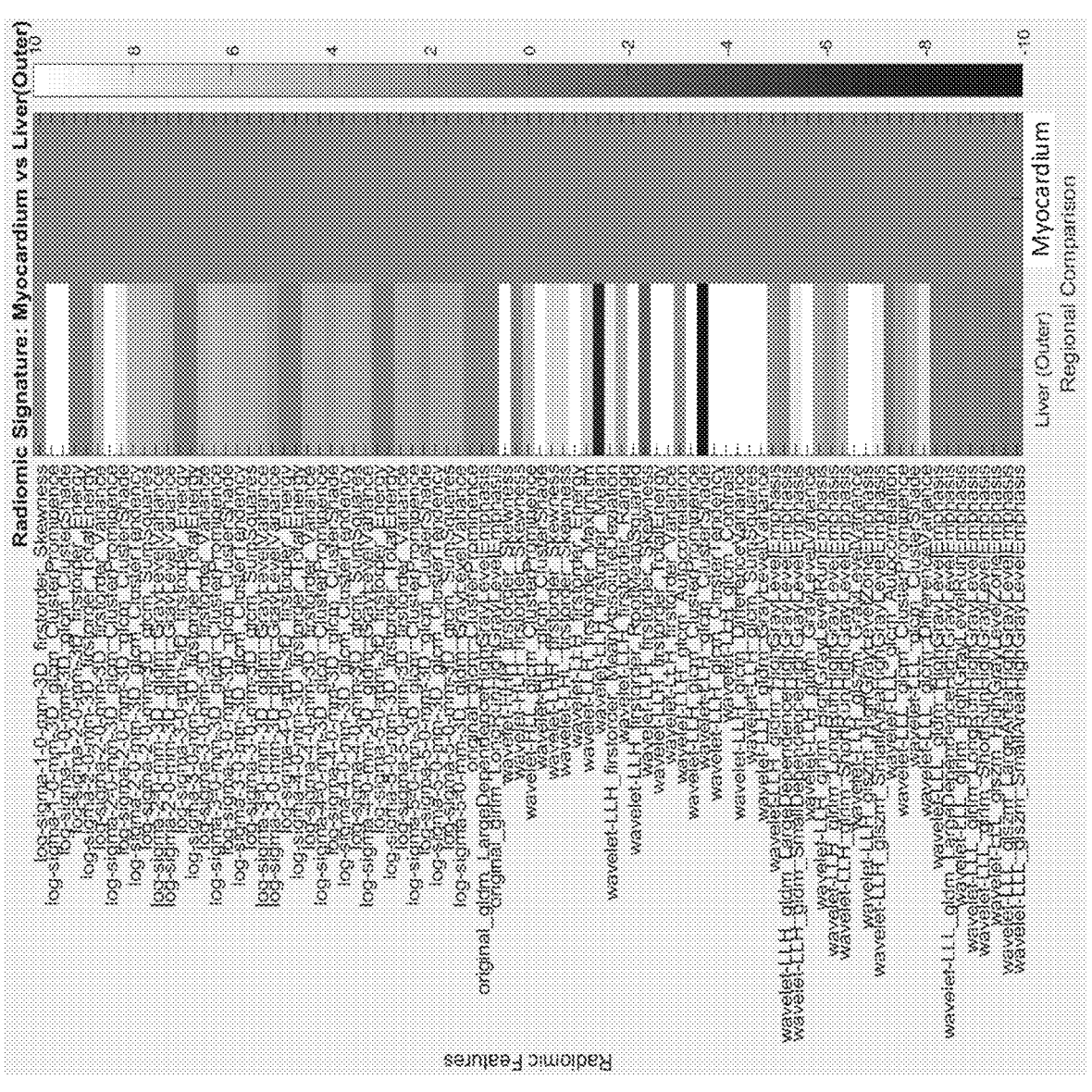
FIG. 8D shows a comparison between the outer liver region and myocardium of radiomic feature values determined from CT scan data.

For the 85 radiomic features that were found to be statistically significant for the myocardium analysis, a comparison of radiomic feature values was performed between the outer region of the liver and the psoas muscle. As shown in FIG. 8C, many of those same features differ greatly between the outer liver and the psoas. FIG. 8D compares the radiomic feature values of those 85 radiomic features for the myocardium and the liver. Since the myocardium and liver parenchyma are both metabolically active, it is hypothesised that radiomic features that do not greatly differ in value between the myocardium and liver (and yet are different between the myocardium and psoas) represent radiomic signatures of functional activity—in this case metabolic activity. As can be seen, in FIG. 8D several features out of the 85 features have been shown to vary little between the myocardium and outer liver region.

As has been demonstrated above, there are radiomic features that may form a radiomic signature of underlying functional activity on a routine CT scan.

FIGS. 9A-9C each show an NCT image of a lymph node that, during a subsequent PET scan (shown subsequently in FIGS. 24 to 26) has been identified as positive for FDG uptake, which is a marker of metastatic cancer. The lymph nodes of FIGS. 9A-9C are labelled respectively as "LN1", "LN2" and "LN3" and all belong to the same patient. FIGS. 9D-9F each show an NCT image of a lymph node that, during the PET scan (shown subsequently in FIGS. 24 to 26), has been identified as negative for FDG uptake in the same patient. The lymph nodes of FIGS. 9D-9F are labelled respectively as "LN4", "LN5" and "LN6".

The radiomic features of the images of the lymph nodes were sampled. In particular, spherical subsamples were identified for each lymph node. For each of the metastatic lymph nodes LN1 and LN2, 27 spherical subsamples of equal volume were identified (see FIGS. 10A and 10B) and radiomic feature values were determined for each subsample. For the metastatic lymph node LN3, 8 spherical subsamples were identified (see FIG. 10C) as the lymph node was too small on the image to obtain 27 subsamples. Radiomic feature values were obtained for each spherical subsample. For the control lymph nodes LN4, LN5 and LN6 radiomic values were taken from a single spherical subsample (see FIGS. 10D-10F).

The radiomic values for the lymph nodes LN1 and LN3 (that were positive for FDG uptake), and the lymph nodes LN4 and LN6 (that were negative for FDG uptake), were used for identification of radiomic features of relevance, while the radiomic values for the lymph nodes LN2 and LN5 were used for validation (as will be demonstrated further below).

Figure 11:
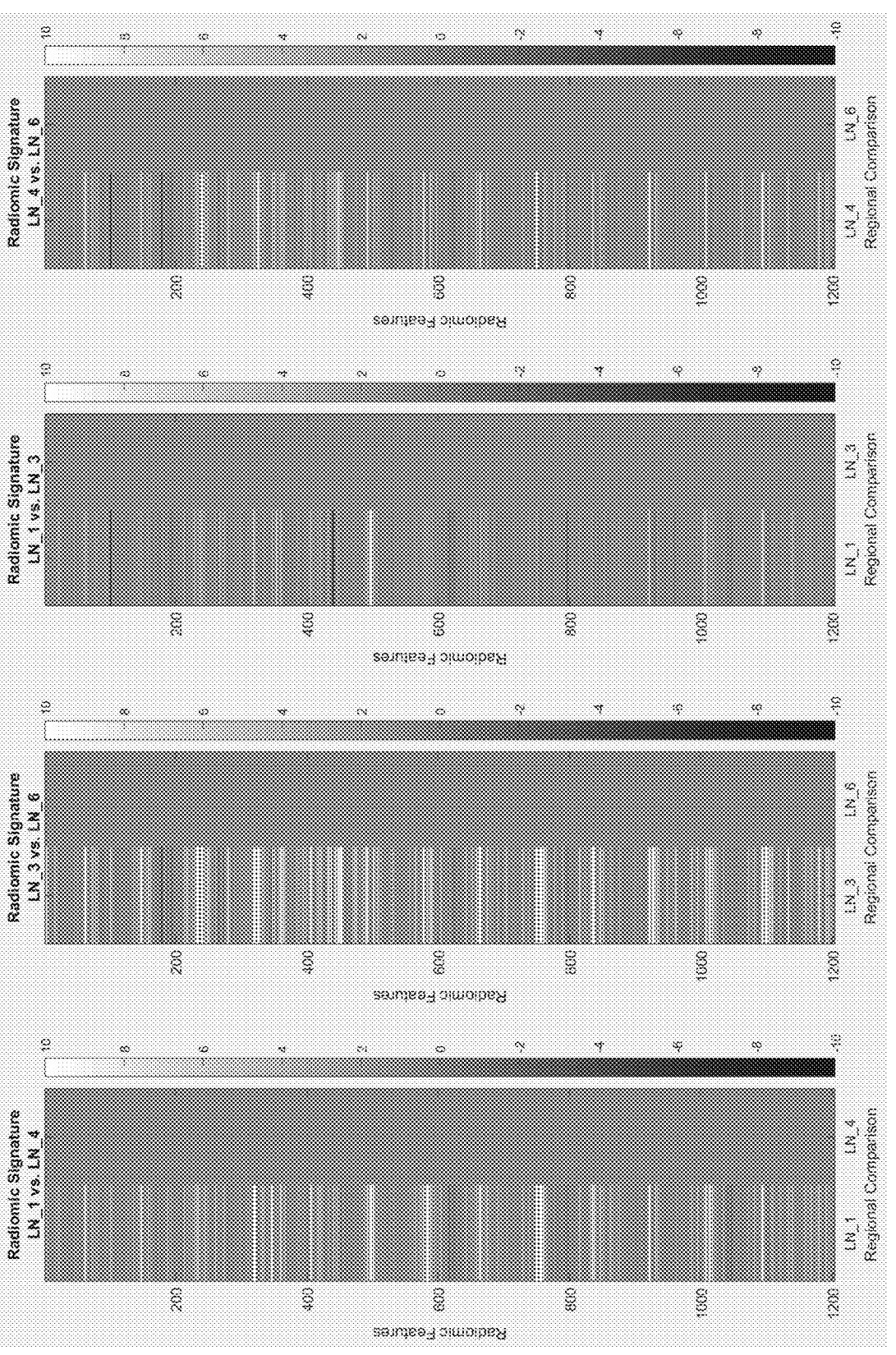
FIG. 11 shows comparisons between various pairs of the lymph nodes of FIGS. 9A-9F of the radiomic feature values determined from the CT scan data.

FIG. 11 shows several radiomic feature comparisons for pairs of lymph nodes, in particular the pairs LN1 & LN4, LN3 & LN6, LN1 & LN3, and LN4 & LN6. Once again 1200 radiomic features were compared. The comparisons of LN1 with LN4 and LN3 with LN6 indicate that there are some values which are not relevant as an indicator of uptake of FDG (namely those features for which there is little difference in radiomic value between the lymph nodes, as one lymph node was metastatic while the other was not). Similarly, the comparisons of LN1 with LN3 and LN4 with LN6 indicate values that are not relevant as an indicator of uptake of FDG (namely those features for which there is a greater difference in radiomic value between the lymph nodes that have similar metabolic activity).

FIG. 12A shows the radiomic feature comparisons for the pairs LN1 & LN4 and LN3 & LN6, but filtered so as to identify the radiomic features for which there is a 10-fold or greater difference between metastatic lymph node and control node. Of these 45 radiomic features, several radiomic features may be useful for devising a radiomic signature relevant for identifying functional activity in lymph nodes in metastatic cancer from an NCT scan. FIG. 12B shows the radiomic feature comparisons for the pairs LN1 & LN3 and LN4 & LN6 filtered so as to identify those radiomic features for which there is a two-fold difference or smaller. These radiomic features thus may characterise some property of the metastatic lymph nodes that is common to both LN1 and LN3, and some property of the control lymph nodes that is common to LN2 and LN4. The radiomic features of the LN1 & LN4, and LN3 and LN6 comparisons of FIG. 12A that overlap with the radiomic features of the LN1 & LN3 and LN4 & LN6 comparisons of FIG. 12B may be useful for identifying a radiomic signature corresponding FDG uptake.

Figure 13:
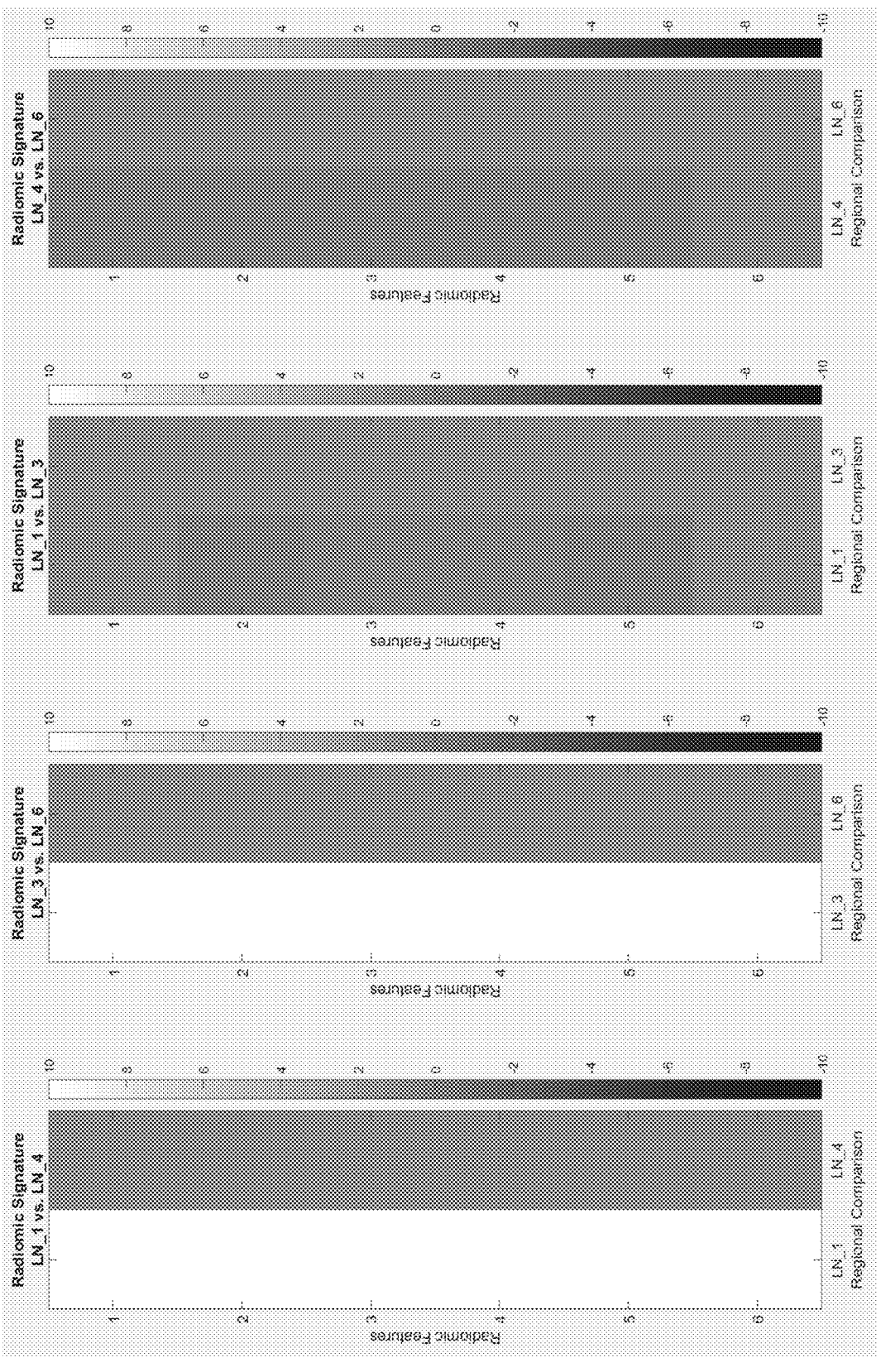
FIG. 13 shows comparisons between various pairs of the lymph nodes of FIGS. 9A-9F of the radiomic feature values determined from the CT scan data.

By performing a similar analysis of the radiomic values for all 27 spherical subsamples from metastatic lymph node LN1 and for all 4 spherical subsamples from metastatic lymph node LN3, 6 radiomic features were identified that consistently showed a 10-fold or greater difference in value between the FDG positive lymph nodes LN1 & LN3 with the control lymph nodes LN4 with LN6. As shown in FIG. 13, these 6 radiomic features do not have greatly different values between LN1 & LN3 (both FDG-positive) or between LN4 and LN6 (both FDG-negative).

Figure 14A:
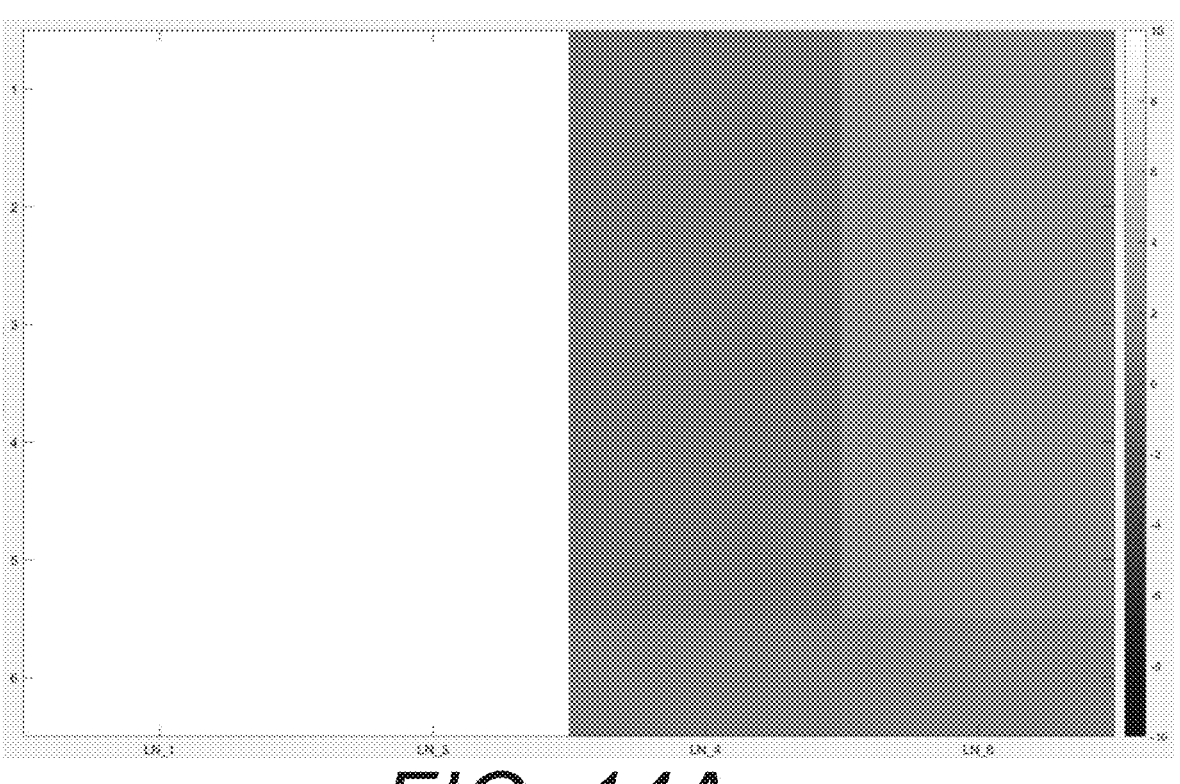
FIGS. 14A and 14B show comparisons between various pairs of the lymph nodes of FIGS. 9A-9F of the radiomic feature values determined from the CT scan data.

In FIG. 14A, the metastatic lymph nodes 1 and 3 are compared to the lymph nodes 4 and 6. The graph of FIG. 14A is normalised against the average of the radiomic values for LN4 and LN6. The Figure shows that the two metastatic lymph nodes have similar properties to each other and are at least 10 fold different than the normal lymph nodes.

Figure 14B:
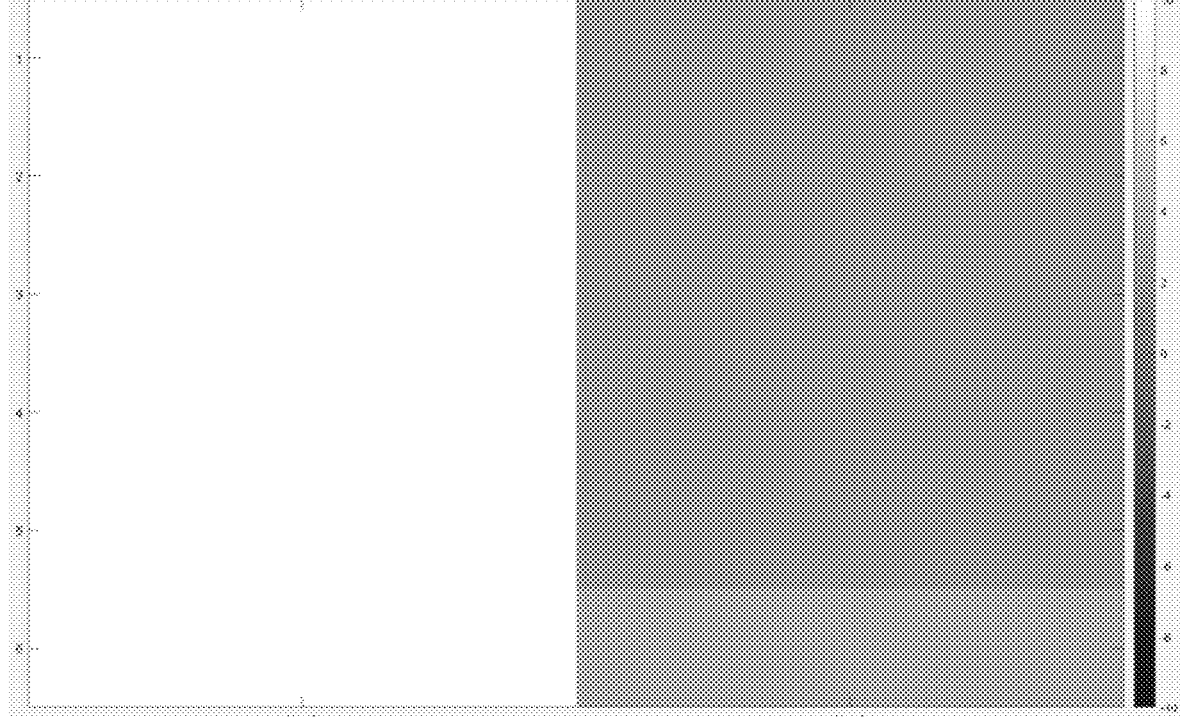

FIG. 14B shows a comparison of these six radiomic feature values for the FDG-positive LN2 and the FDG-negative LN5. LN2 and LN5 were not used to determine those 6 radiomic features. FIG. 14B suggests that these six radiomic features are useful as an indicator of FDG uptake. The six radiomic features are shown in the table of FIG. 15.

Figure 16A:
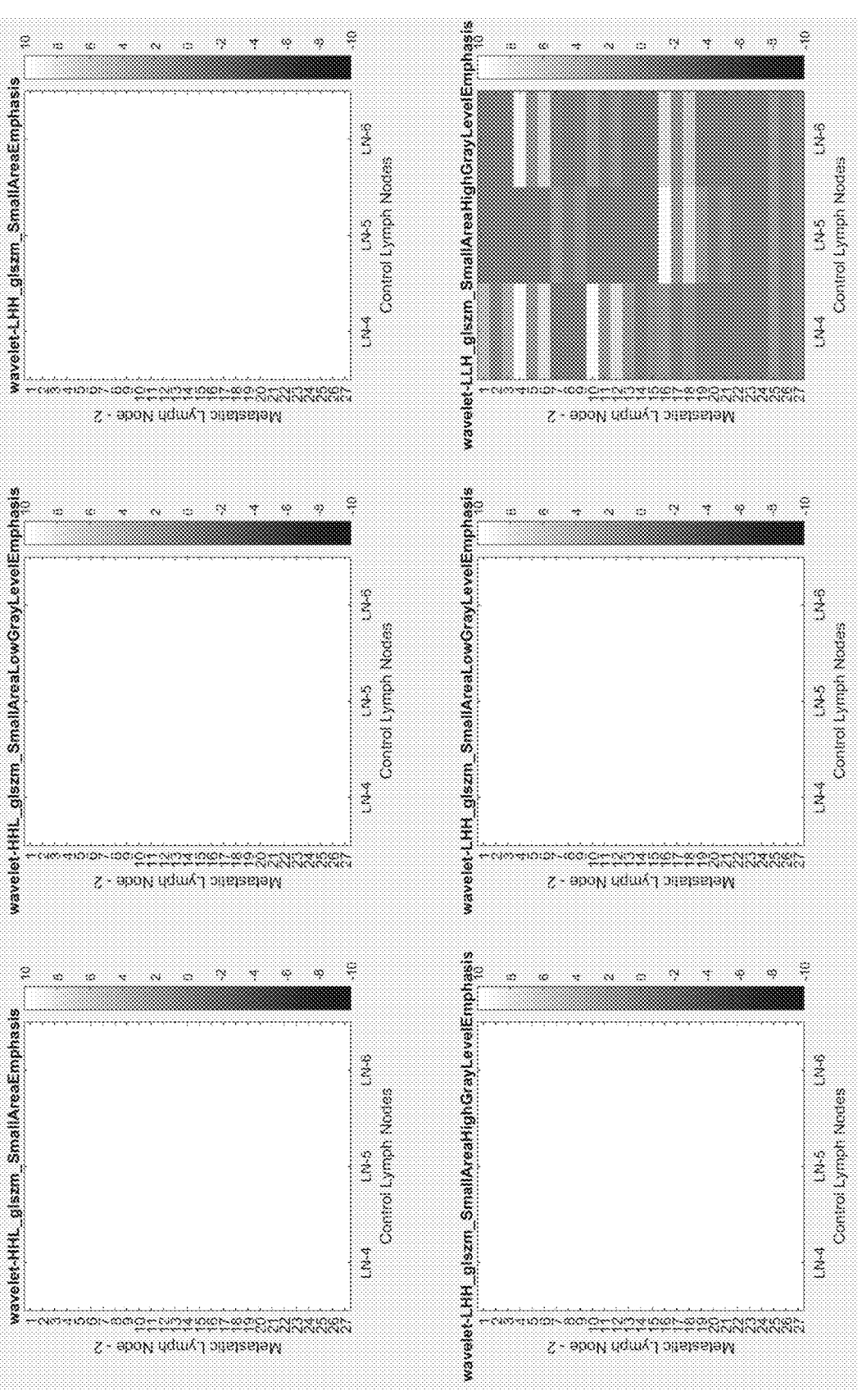
FIG. 16A shows, for each of the six radiomic features of FIG. 15, a comparison of the radiomic feature value for that radiomic feature in each of the 27 spherical subsamples of LN1 with each of control lymph nodes LN4, LN5 and LN6.
Figure 16B:
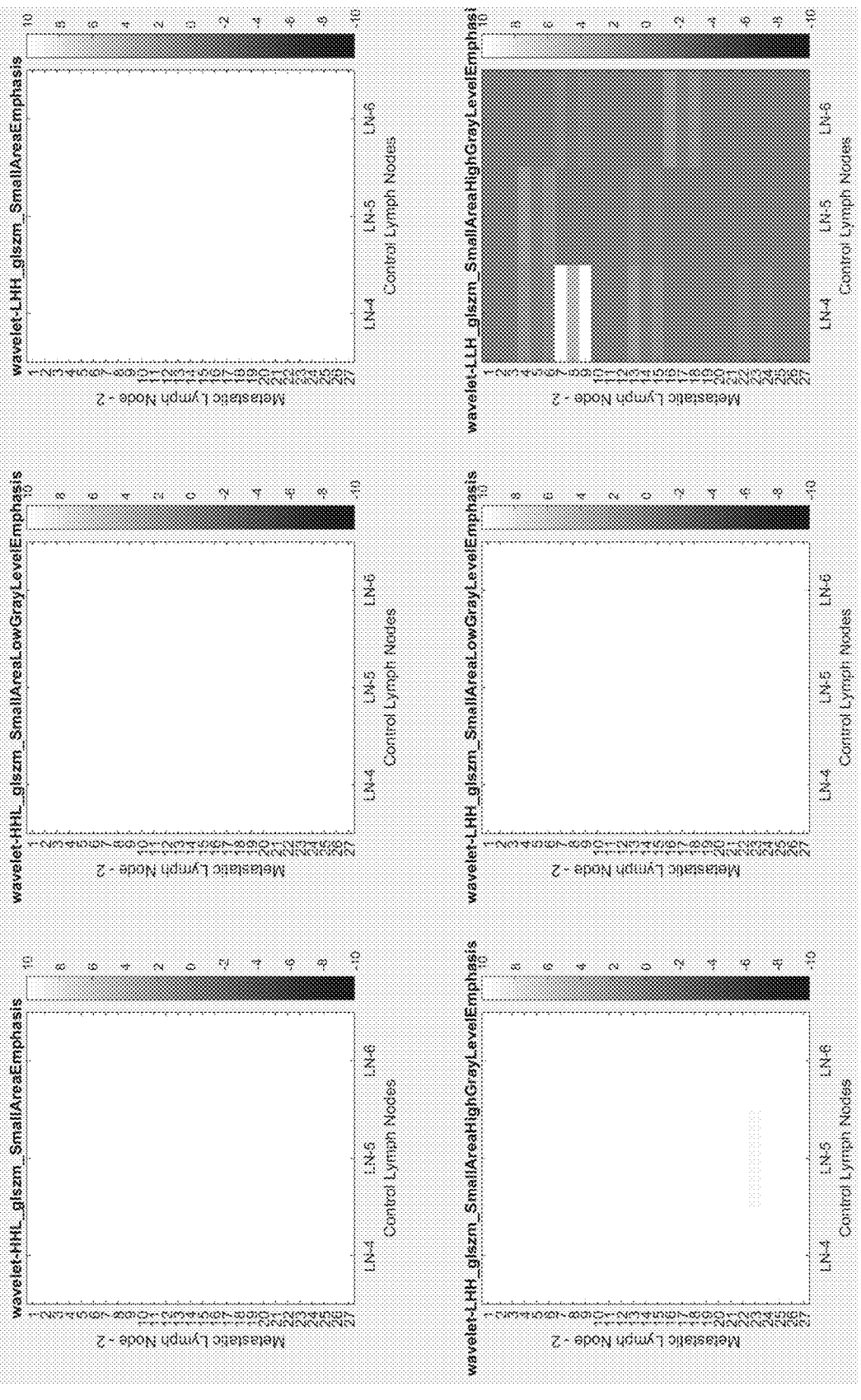
FIG. 16B shows, for each of the six radiomic features of FIG. 15, a comparison of the radiomic feature value for that radiomic feature in each of the 27 spherical subsamples of LN2 with each of control lymph nodes LN4, LN5 and LN6.
Figure 16C:
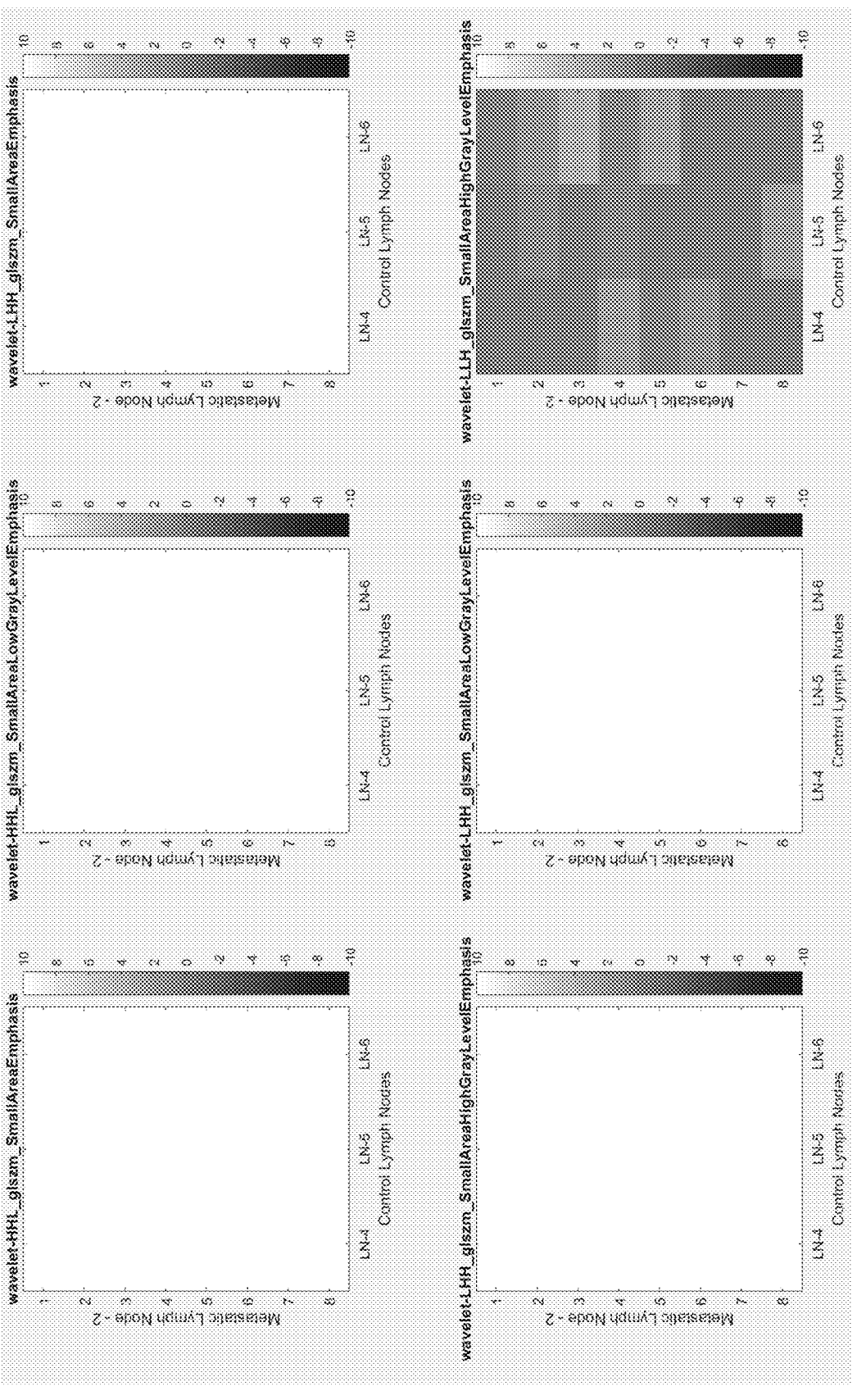
FIG. 16C shows, for each of the six radiomic features of FIG. 15, a comparison of the radiomic feature value for that radiomic feature in each of the 8 spherical subsamples of LN3 with each of control lymph nodes LN4, LN5 and LN6.

FIG. 16A shows, for each of the six radiomic features of FIG. 15, a comparison of the radiomic feature value for that radiomic feature in each of the 27 spherical subsamples of LN1 with each of control lymph nodes LN4, LN5 and LN6. FIG. 16B shows, for each of the six radiomic features of FIG. 15, a comparison of the radiomic feature value for that radiomic feature in each of the 27 spherical subsamples of LN2 with each of control lymph nodes LN4, LN5 and LN6. FIG. 16C shows, for each of the six radiomic features of FIG. 15, a comparison of the radiomic feature value for that radiomic feature in each of the 8 spherical subsamples of LN3 with each of control lymph nodes LN4, LN5 and LN6.

Figures 17A, 17B, 17C:
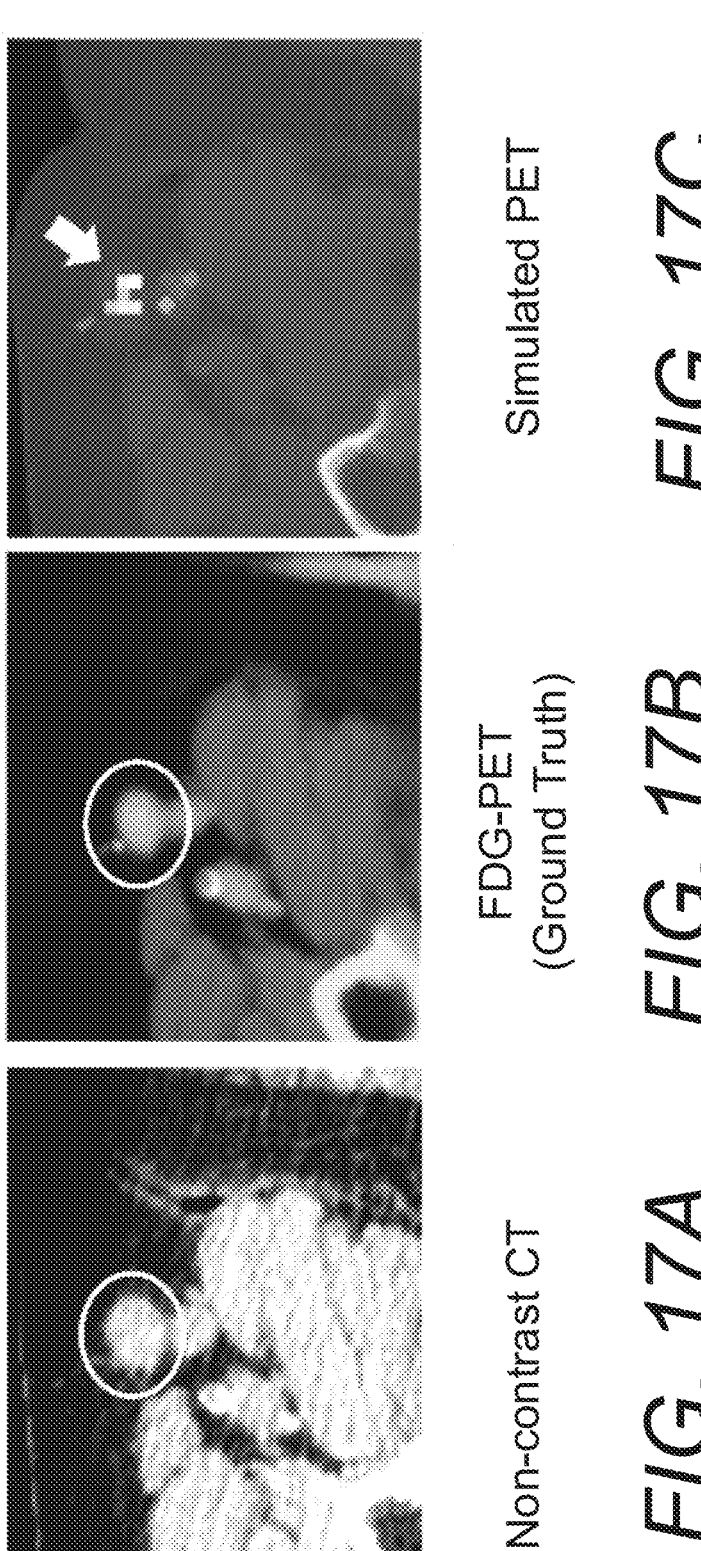
FIGS. 17A, 17B, and 17C respectively show an NCT image, a FDG-PET scan image, and a simulated/pseudo-FDG-PET-CT scan image of the lymph node LN1.

It is feasible to generate simulated/pseudo-FDG-PET-CT images without using any FDG radiotracer using only the information available from a NCT image. This is illustrated in FIGS. 17A, 17B and 17C. FIG. 17A replicates the NCT image of LN1 that was present in FIG. 9A and shows structural features. FIG. 17B shows an FDG-PET scan of LN1 and as can be seen from the figure the lymph node is shown in stark contrast to its surroundings due to the uptake of FDG by the lymph node. That is, the FDG-PET image of FIG. 17B shows a functional feature, namely the region of metabolic uptake of the FDG. FIG. 17C shows a visualisation in the form of a simulated FDG-PET-CT image. In order to generate the simulated FDG-PET-CT image of FIG. 17C, the radiomic feature-1 of FIG. 15 was analysed for each voxel of the NCT image of FIG. 17A. The intensity of the radiomic feature 1 is displayed to provide the visualisation of FIG. 17C. As can be seen clearly in the Figure, the circled region of FIG. 17C corresponds to the region of the LN1 that shows as positive for FDG uptake in the PET scan image of FIG. 17B.

A similar analysis is shown in FIGS. 18A, 18B and 18C for LN2. FIG. 18A replicates the NCT image of FIG. 9B. FIG. 18B shows a FDG-PET image of LN2. FIG. 18C shows a simulated FDG-PET-CT image obtained by analysing radiomic feature 1 from the table of FIG. 15.

Figures 19A, 19B, 19C:
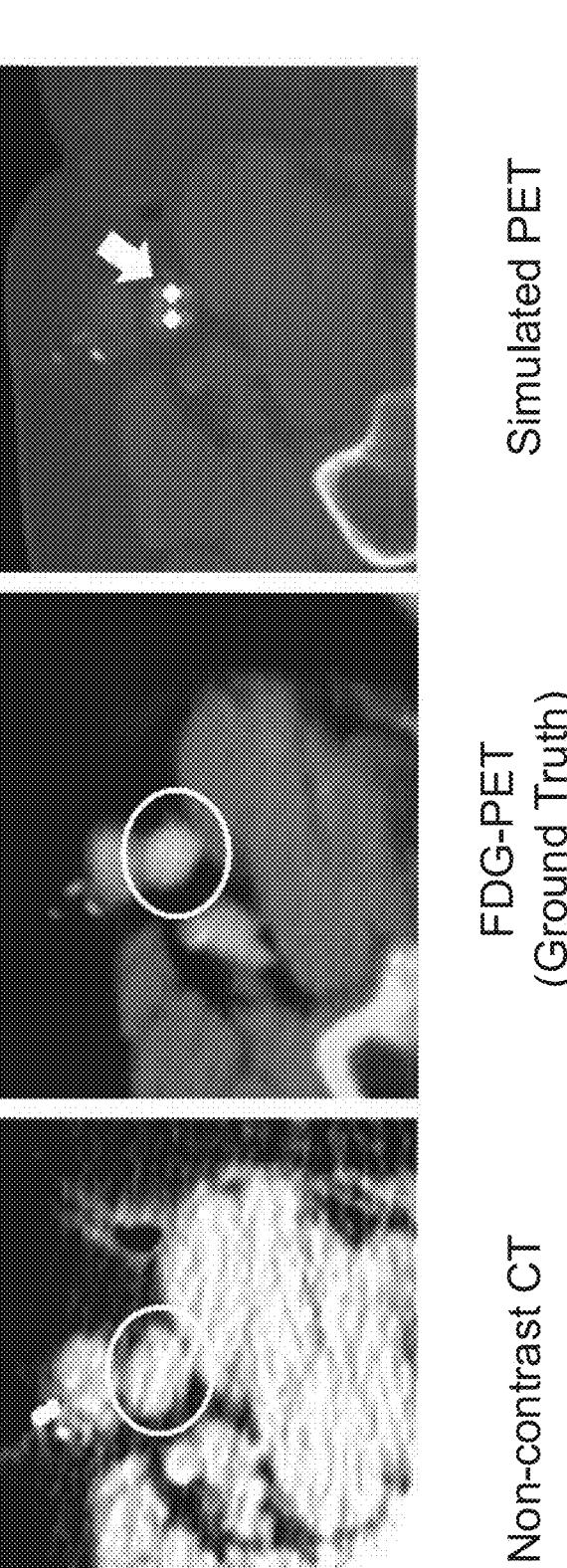
FIGS. 19A, 19B, and 19C respectively show an NCT image, a FDG-PET scan image, and a simulated/pseudo-FDG-PET-CT scan image of the lymph node LN3.

A similar analysis is shown in FIGS. 19A, 19B and 19C for LN3. FIG. 19A replicates the NCT image of FIG. 9C. FIG. 19B shows a FDG-PET image of LN3. FIG. 19C shows a simulated FDG-PET-CT image obtained by analysing radiomic feature 1 from the table of FIG. 15.

A similar analysis is shown in FIGS. 20A, 20B and 20C for LN4. FIG. 20A replicates the NCT image of FIG. 9D. FIG. 20B shows a FDG-PET image of LN4. FIG. 20C shows a simulated FDG-PET-CT image obtained by analysing radiomic feature 1 from the table of FIG. 15. As shown in FIG. 20B, LN4 is a lymph node that does not take up FDG, and the corresponding node in FIG. 20C similarly does not highlight LN4.

A similar analysis is shown in FIGS. 21A, 21B and 21C for LN5. FIG. 21A replicates the NCT image of FIG. 9E. FIG. 21B shows a FDG-PET image of LN5. FIG. 21C shows a simulated FDG-PET-CT image obtained by analysing radiomic feature 1 from the table of FIG. 15. As shown in FIG. 21B, LN5 is a lymph node that does not take up FDG, and the corresponding node in FIG. 21C similarly does not highlight LN5.

A similar analysis is shown in FIGS. 22A, 22B and 22C for LN6. FIG. 22A replicates the NCT image of FIG. 9F. FIG. 22B shows a FDG-PET image of LN6. FIG. 22C shows a simulated FDG-PET-CT image obtained by analysing radiomic feature 1 from the table of FIG. 15. As shown in FIG. 22B, LN6 is a lymph node that does not take up FDG, and the corresponding node in FIG. 22C similarly does not highlight LN6.

It has thus been demonstrated that a visualisation showing both structural features and functional features can be generated from a NCT image without the need for any radiotracers. In particular, it has been demonstrated that one can compare radiomic feature values of a target region shown in the CT image with corresponding threshold values, and determine from the comparison, functional features within the target region. One is further able to generate using the determined functional features, a visualisation of the target region identifying the functional features and the structural features.

While it has been demonstrated above that such a radiomic analysis can be used to identify metastasis of cancer in lymph nodes, the same techniques can be applied to identify functional activity in other tissues and organs.

Having demonstrated that CT images, including NCT images, contain enough information within them to identify functional features, the inventors performed a series of experiments to investigate whether various machine learning models could be trained to identify functional activity in a CT image and/or to produce simulated functional image datasets.

The inventors have performed a series of experiments which will now be described in further detail. These experiments will be referred to as Experiments 1A, 1B and 2. In Experiment 1A the inventors demonstrated that one could train a classification algorithm, in particular a random forest, to identify areas of FDG uptake (indicative of functional activity) in a non-contrast CT image (NCT image). In Experiment 1B, the inventors demonstrated that one could train a classification algorithm, in particular a random forest, to distinguish areas of high FDG uptake from areas of low FDG uptake in a NCT image. In Experiment 2, the inventors sought to determine whether a generative adversarial network (GAN) could be used to identify areas of FDG uptake in a NCT image.

For Experiments 1A, 1B and 2, the inventors utilised a collection of paired FDG-PET and CT images of 298 patients with diagnosed head and neck squamous cell carcinoma (HNSCC). The paired images originated from four different institutions in Quebec, Canada. The complete dataset is publicly available via The Cancer Imaging Archive (TCIA) at http://www.cancerimagingarchive.net. The patients underwent routine treatment management (radiation—48, 16%; chemo-radiation—252, 84%). Imaging was obtained within a median of 18 days (range 6-66) prior to the start of treatment. The median follow up time after treatment was 43 months. Of the 298 patients, 45 patients developed locoregional recurrence, 40 patients developed distant metastasis and 56 patients died. Additional information regarding the patient cohort characteristics can be found within the previously published data documentation.

Figure 23:
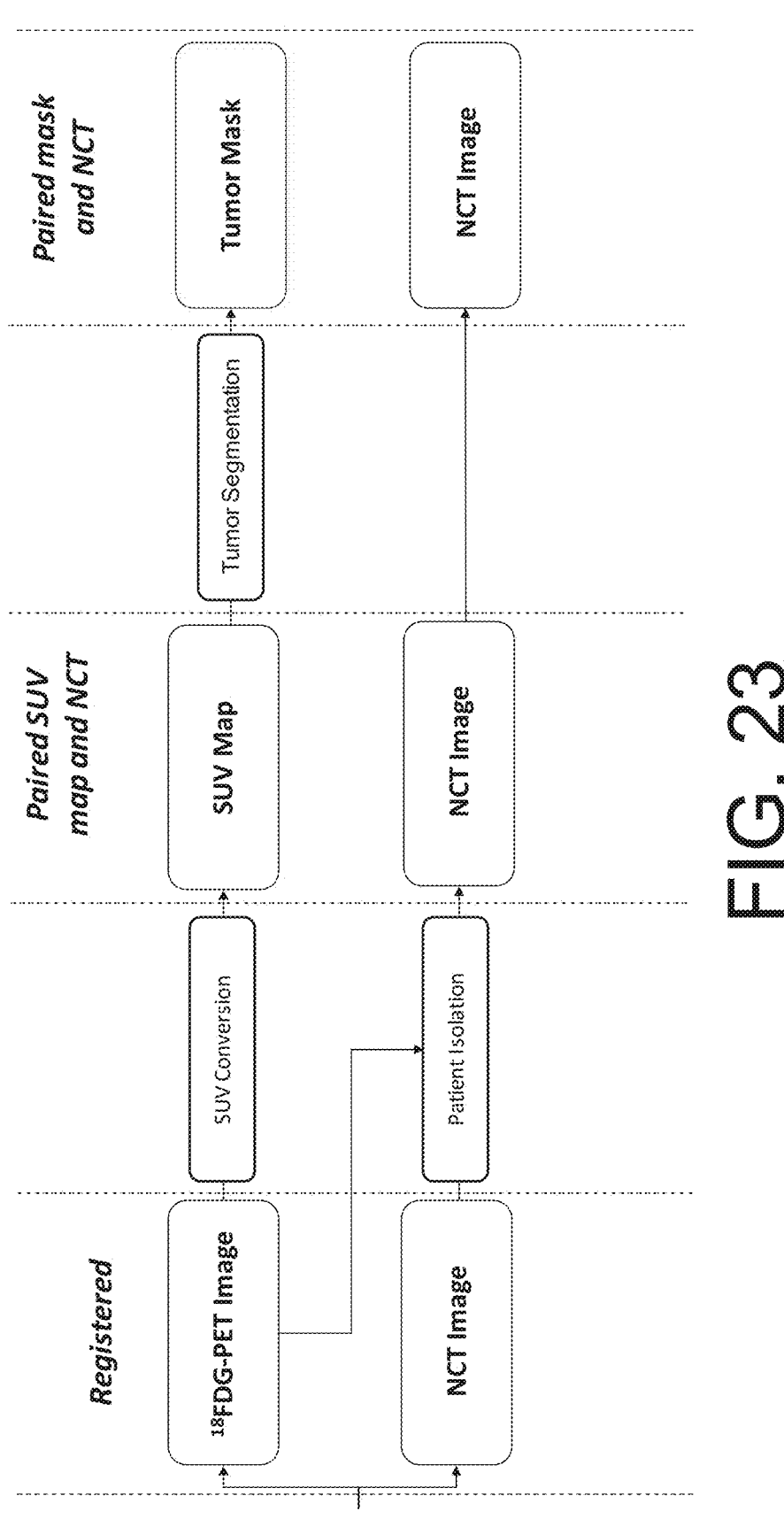
FIG. 23 illustrates a methodology for preparing training sets for Experiments 1A, 1B and 2.

FIG. 23 shows the methodology for the preparation of the training sets for the three experiments. For each PET image of the image pairs, a Standardized Uptake Value map was derived. Standardized Uptake Value (SUV) is a mathematically derived ratio of tissue radioactivity concentration from the PET image that is standardized to the patient's body weight, the initial radiation dose, and the time duration between bolus injection and imaging. Although vulnerable to variability (ex. image noise, low image resolution, region-of-interest-input), this semi-quantitative calculation is a common technique used to standardize PET image comparison between multiple patients and cohorts. As the original TCIA dataset comprised images taken from four different institutions and a variety of machines all of which may have been calibrated differently, the conversion of the PET images to SUV maps helps to control for such variations by providing standardised image values. The SUV (per body weight) was derived according to:

$$SUV_{BW} = \frac{A_C}{D * 2^{\left(\frac{-\Delta t}{Thalf}\right)}} * W$$

where $A_C$ represents the Activity Concentration (derived from the PET values), D represents the radiation dose provided to the patient (in Becquerels), W represents the patient's weight (in kilograms), $\Delta t$ represents the delay time between the injection time and the scan start time, and Thalf represents the half-life of the injected radionuclide.

Of the 298 patients, at the time of imaging the median patient weight was 75 Kg (range: 43-142 Kg) and the median dosage of FDG injected was $1.65 \times 108$ Bq (range: $3.81 \times 10^8$-$31.82 \times 10^8$). Additionally, the median duration between injection and scan time was $1.80 \times 10^4$ s (range: $1.04 \times 10^4$-$3.01 \times 10^4$). Each patient-specific combination of weight, dose, and delay time, along with the half-life of FDG (6588 s) was used to calculate the appropriate SUV map. Average SUV within the calculated images is $0.19 \pm 0.06$. SUV maps were generated from the provided PET images to standardize measurements between patients.

Figure 24:
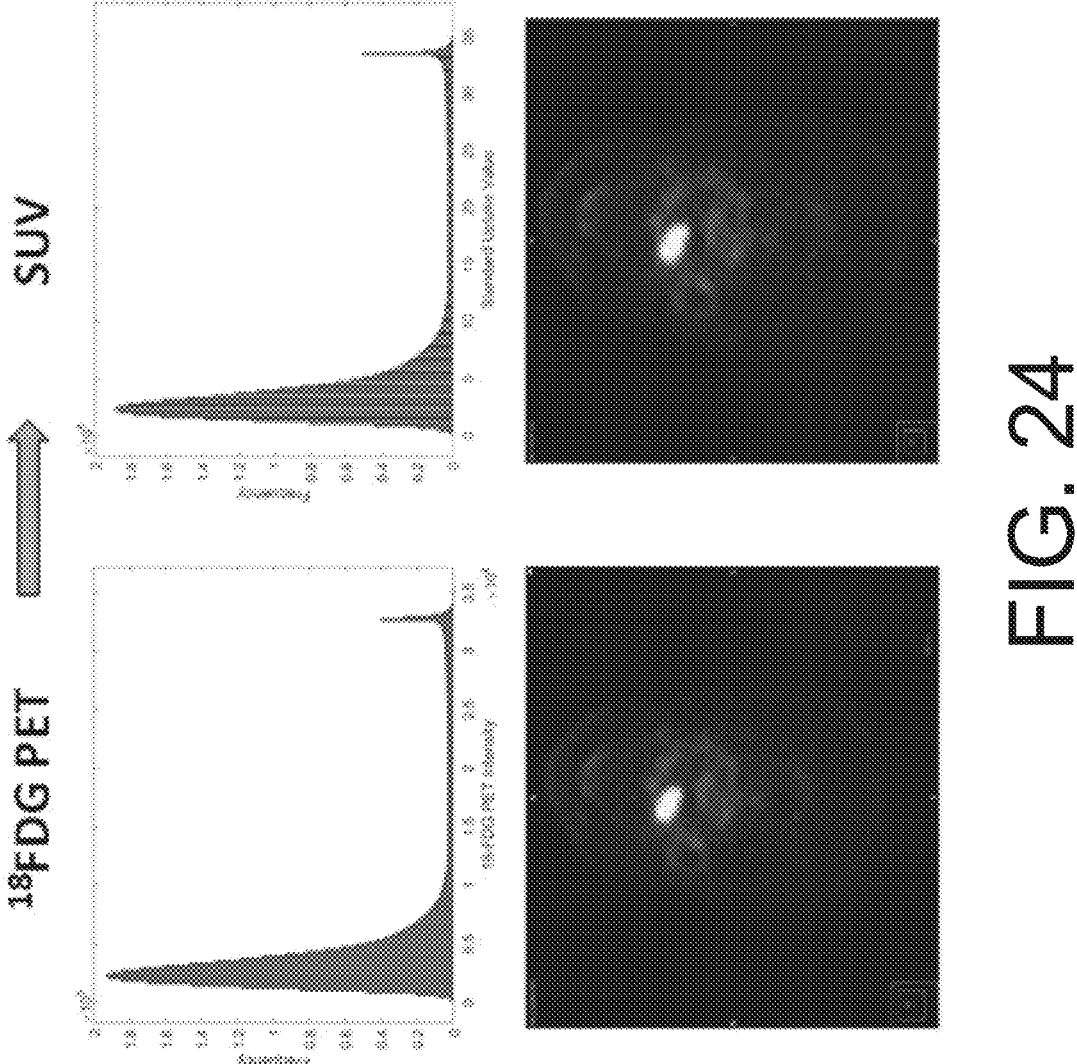
FIG. 24 illustrates a transformation applied to an FDG-PET image to produce a SUV map.

FIG. 24 illustrates the effect of transforming a FDG-PET image to an SUV image for a single patient ("Patient 1"). Patient 1 has a body weight (W) of 80 kg, and was provided with a radiopharmaceutical of dose D of 617,791,424Bq. The half-life (Thalf) of FDG is approximately 6588 s, and the delay time between the injection of the radiopharmaceutical and the scan start time was approximately 19,627 s. The activity concentration $A_C$ is the pixel intensity within the FDG-PET image. The resulting SUV map has a similar distribution to the original FDG-PET image but is bounded by 0 and 10.

Referring again to FIG. 23, prior to assessing registration accuracy, the entire patient was segmented from both the NCT image and SUV map. Binary segmentation of the SUV map was generated using threshold-based methods (if SUV ≥0.1, label as 1 [patient]; if SUV <0.1, label as 0 [background]). Subsequent morphological dilatation and erosion operations using a spherical structuring element within the interior of the patient was used to connect components. 3D-gaussian filtering on the segmented images (sigma, 2) was used to smooth all SUV-map derived patient segmentations. Similar threshold-based and dilation/erosion methods were used to generate the segmentation from the NCT images (if Hounsfield Unit, HU ≥−500, label as 1 [patient]; if HU<−500, label as 0 [background]). Registration accuracy was assessed using the Sorensen-Dice (DICE) coefficient, which is a ratio comparing the similarity between segmentations. The DICE coefficient is given by twice the number of elements common to both segmentations divided by the total number of elements. If the DICE score was less than 90%, a non-rigid b-spline registration algorithm was implemented on the segmentations to ensure registration accuracy. Additionally, this method was used to isolate the patient from the underlying table in the NCT image.

Figure 25:
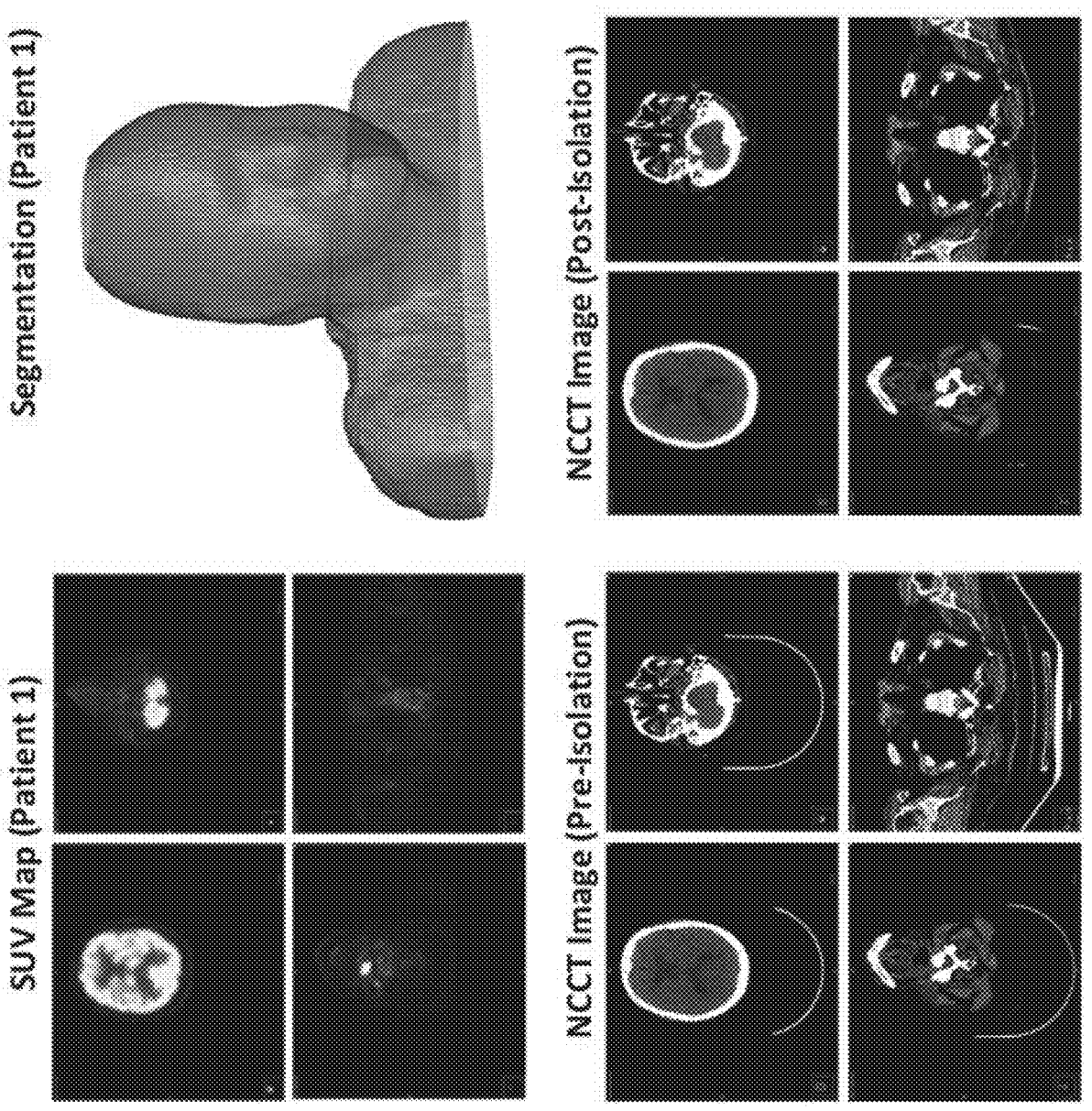
FIG. 25 shows four SUV maps, four NCT images prior to patient isolation, the four NCT images after patient isolation, and the segmentation of the patient used in patient isolation.

FIG. 25 shows four SUV map images from Patient 1 (top left of FIG. 25), the segmentation of the patient (top right of FIG. 25), the corresponding NCT images before patient isolation (bottom left of FIG. 25) and the NCT images after patient isolation was performed (bottom right of FIG. 25).

Referring again to FIG. 23, after the SUV maps have been generated, and the NCT images have been edited to isolate the patient, one has a set of paired SUV images and NCT images that correspond well to one another as scored by the DICE coefficient. The SUV maps (or more particularly, an inverted version of the SUV maps) and the NCT images after patient isolation provided a suitable training set for training a GAN (Experiment 2), as will be discussed further below in relation to FIGS. 30 to 35. However it will be noted that while paired images were used in training the GAN, one does not require the images to be paired to train a GAN.

For Experiments 1A and 1B, a further step was taken in the data preparation process. In particular, steps were taken to identify the metabolically-active tumour areas within the patient. In order to perform the tumour segmentation using the PET-derived SUV map, the inventors made the following assumptions: (a) the SUV map and NCT image are registered and display considerable overlap (a reasonable assumption given the DICE scores), (b) the largest connected component in the SUV map that displays elevated FDG uptake is the brain, and (c) tumour areas are highly metabolic and display increased FDG uptake. A patient-specific threshold (0.35×Maximum SUV) was used to isolate regions with increased or elevated SUV. A convolution filter with a kernel size of 3 was used to smooth the initial segmentation output. Subsequently, connected component analysis was used to separate the brain from other regions of elevated FDG uptake. All generated segmentations were assessed for manual overlap with the SUV Map.

Referring again to FIG. 23, the dataset for Experiments 1A and 1B comprised paired tumour segmentation masks derived from the SUV maps and the corresponding NCT images after patient isolation.

Figure 26:
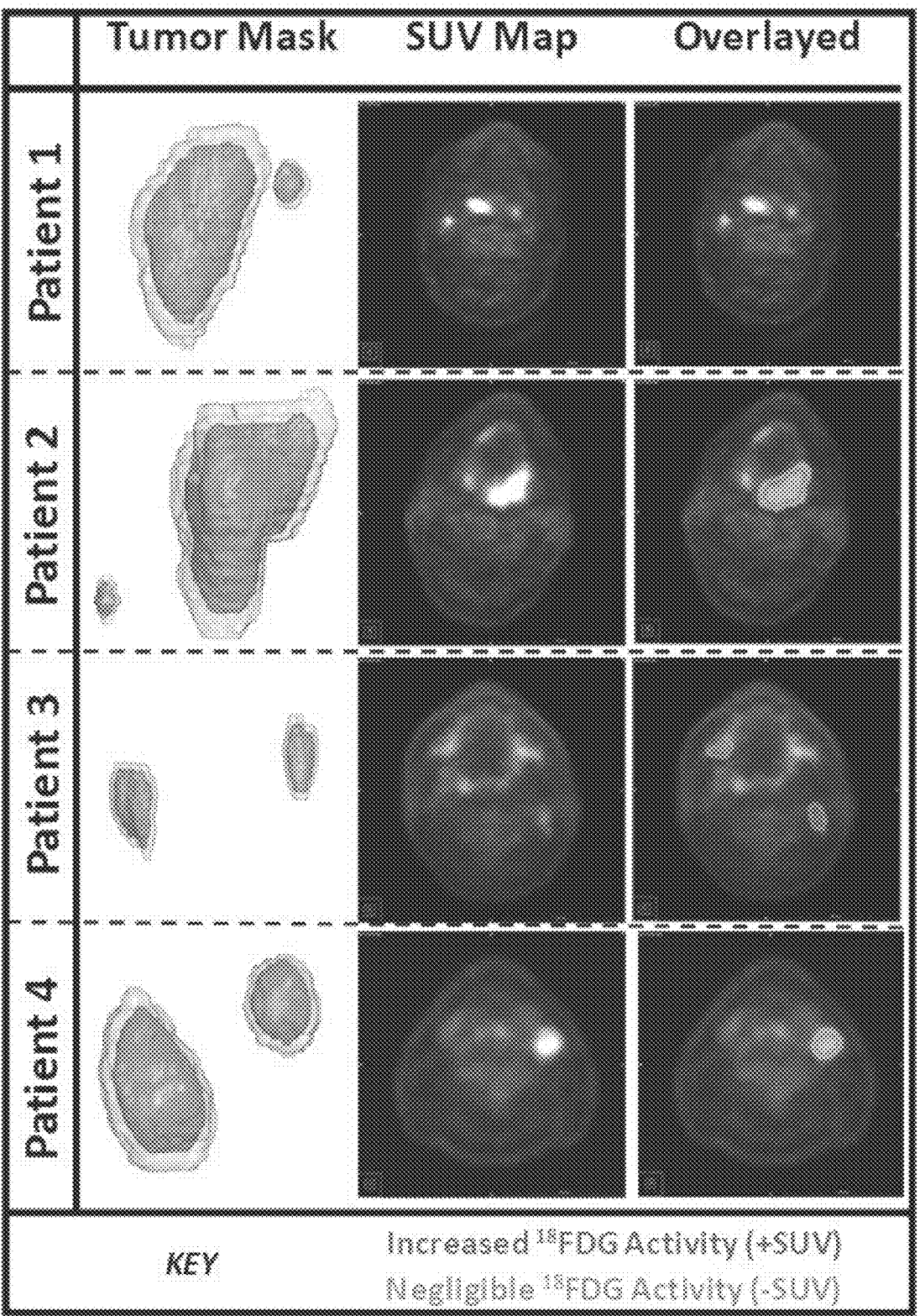
FIG. 26 shows four tumour masks produced in preparation for Experiment 1A, the corresponding SUV maps, and the SUV maps overlaid with said tumour masks.

In Experiment 1A, the aim was to investigate the radiomic differences between regions with elevated FDG uptake (+SUV, i.e. tumour) and immediately adjacent regions of low/negligible FDG uptake (−SUV, i.e. non-tumour). In order to sample these regions, the tumour surface boundary was dilated by a factor of 2. The centroid of the expanded segmentation mask was matched to that of the original tumour segmentation. This resulted in two concentric segmentations with equal volumes. FIG. 26 illustrates, for several patients, the generated tumour masks, the relevant SUV maps, and the SUV maps overlaid with the tumour masks.

Figure 27:
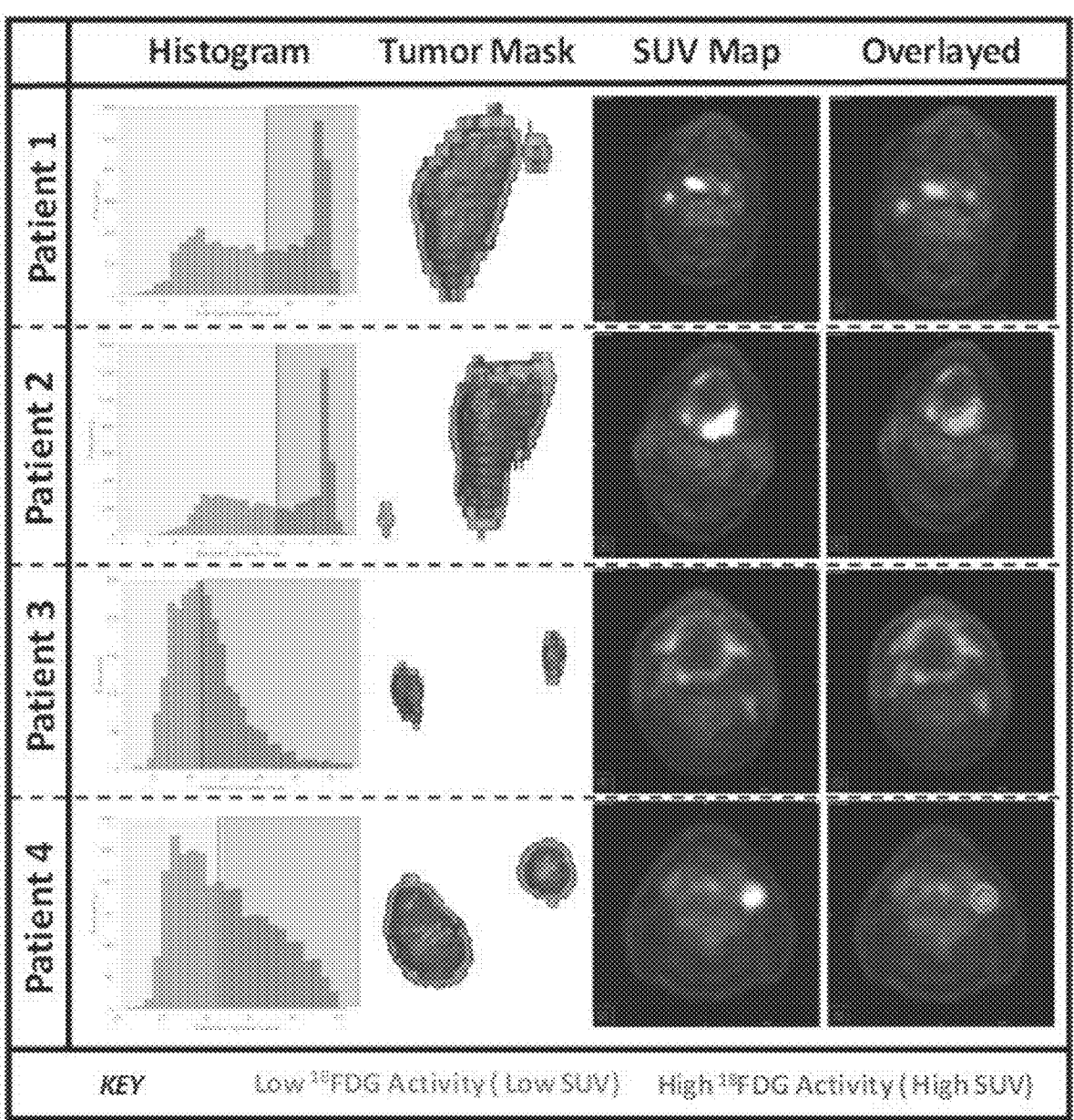
FIG. 27 shows four tumour masks produced in preparation for Experiment 1B, the corresponding SUV maps, and the SUV maps overlaid with said tumour masks, along with histograms indicating the frequency of high and low uptake regions.

In Experiment 1B, the aim was to characterise the radiomic differences within different regions of a tumour (which is metabolically active). This was divided into two sub-regions based on the FDG uptake avidity: (a) High FDG uptake (≥50th percentile of SUVs [$SUV_{50}$] within the tumour), and (b) Low FDG uptake (<50th percentile of SUVs within the tumour). The constrained sub-region therefore represents an area of higher FDG uptake within the tumour volume. The $SUV_{50}$ was specific to each patient and allowed for the differentiation of FDG uptake within the tumour. FIG. 27 illustrates, for several patients, the generated tumour masks, the relevant SUV maps, and the SUV maps overlaid with the tumour masks.

Figure 28:
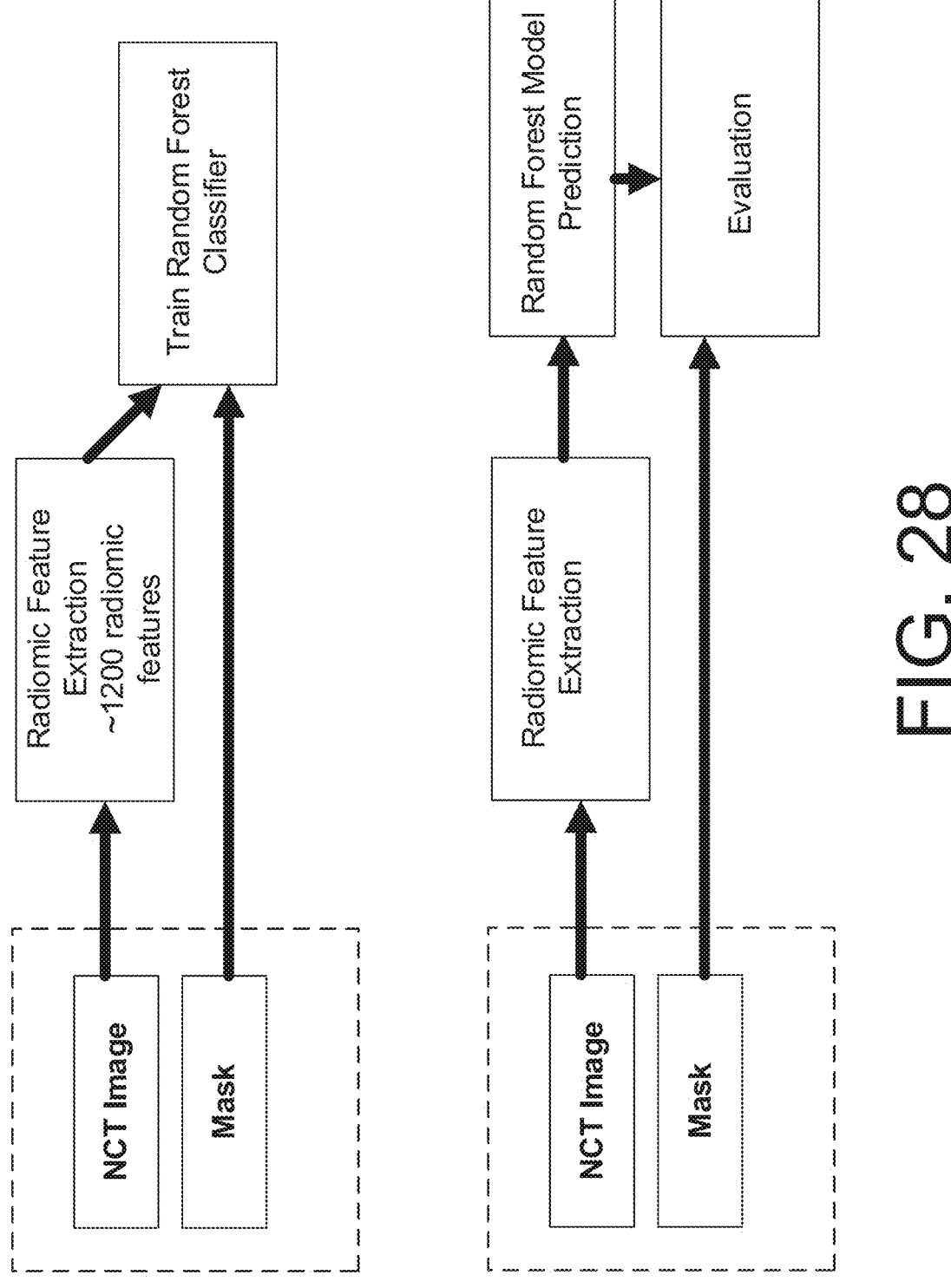
FIG. 28 illustrates a methodology used in performing Experiments 1A and 1B.

The methodology for Experiments 1A and 1B is illustrated in FIG. 28. Of the 298 patients in the TCIA dataset, paired NCT images and tumour segmentation masks (546 pairs) for 250 of the patients were used for training random forest classifiers and NCT images and tumour segmentation masks (137 pairs) for the remaining 48 patients were used for testing the random forest classification models. During training, for each pair, radiomic feature extraction was performed on several regions of the NCT image. The extracted radiomic feature values for each NCT image and the values for the corresponding segmentation masks were then provided to the random forest classification algorithm to learn a relationship between radiomic feature values and the uptake of FDG.

In the 298 patients with HNSCC, 683 tumour lymph nodes were identified. Anisotropic image and segmentation masks were resampled into isotropic-sized voxels (1 mm, 2 mm, 3 mm, 4 mm and 5 mm). Parameter settings for radiomic feature extraction included 5 pre-defined histogram bin widths (5, 10, 15, 20 and 25). For each set of image and parameter settings, 18 first-order, 68 second-order and 1118 filter-based features were calculated. This results in a total of 30,125 features for each region of interest (ROI) ((86 1st/2nd order features+[86*13 filtered images])×5 Isotropic Settings×5 Bin-width setting).

In Experiment 1A, an identical protocol was followed to obtain radiomic features from tumours with increased FDG uptake (n=683) and immediately adjacent regions with negligible FDG uptake (n=683). Similarly, in Experiment 1B, radiomic features from regions of high (n=528) and low (n=683) FDG uptake within metabolically active tumours were extracted. Following feature extraction, tumours were divided into training and testing cohorts using an approximate 70:30 split. Given that each patient may have multiple tumour hotspots, train and test cohorts were divided based on patient to prevent data leakage. Feature selection, model training and optimization were performed on the training cohort. The testing cohort was introduced to evaluate model performance.

In both Experiments 1A and 1B, multiple random forests were trained using a different combination of radiomic features. For each model, 10-fold cross-validation was used (100 iterations). In each of Experiments 1A and 1B, four random forest models in particular were constructed.

The first random forest model (Model I) considered only first order features from the (post-patient isolation) NCT images of the training set (450 features per ROI).

The second random forest model (Model II) considered first order features and filter-based features from the (post-patient isolation) NCT images and filtered images. (Original+Filtered, 5,850 features per ROI).

The third random forest model (Model III) considered both first order features and second order features from the (post-patient isolation) NCT images of the training set (2,150 Features per ROI).

The fourth random forest model (Model IV) considered first order features, second order features and filter-based features from the (post-patient isolation) NCT images of the training set and filtered images (Original+Filtered, 30,125 features per ROI).

First-Order features comprise image-based statistics (ex. minimum, mean, median, maximum, kurtosis, etc.), which describe the distribution of voxel intensities within the image region defined by the segmentation mask. These features are not influenced by the shape or volume of the defined mask.

Second-order features comprise matrix-based features that extract the radiomic "texture" within a defined region of interest shape/volume.

The top 25 features for each model were selected for model training and optimization. Each model was trained using a 100-fold cross-validation method.

Figure 29:
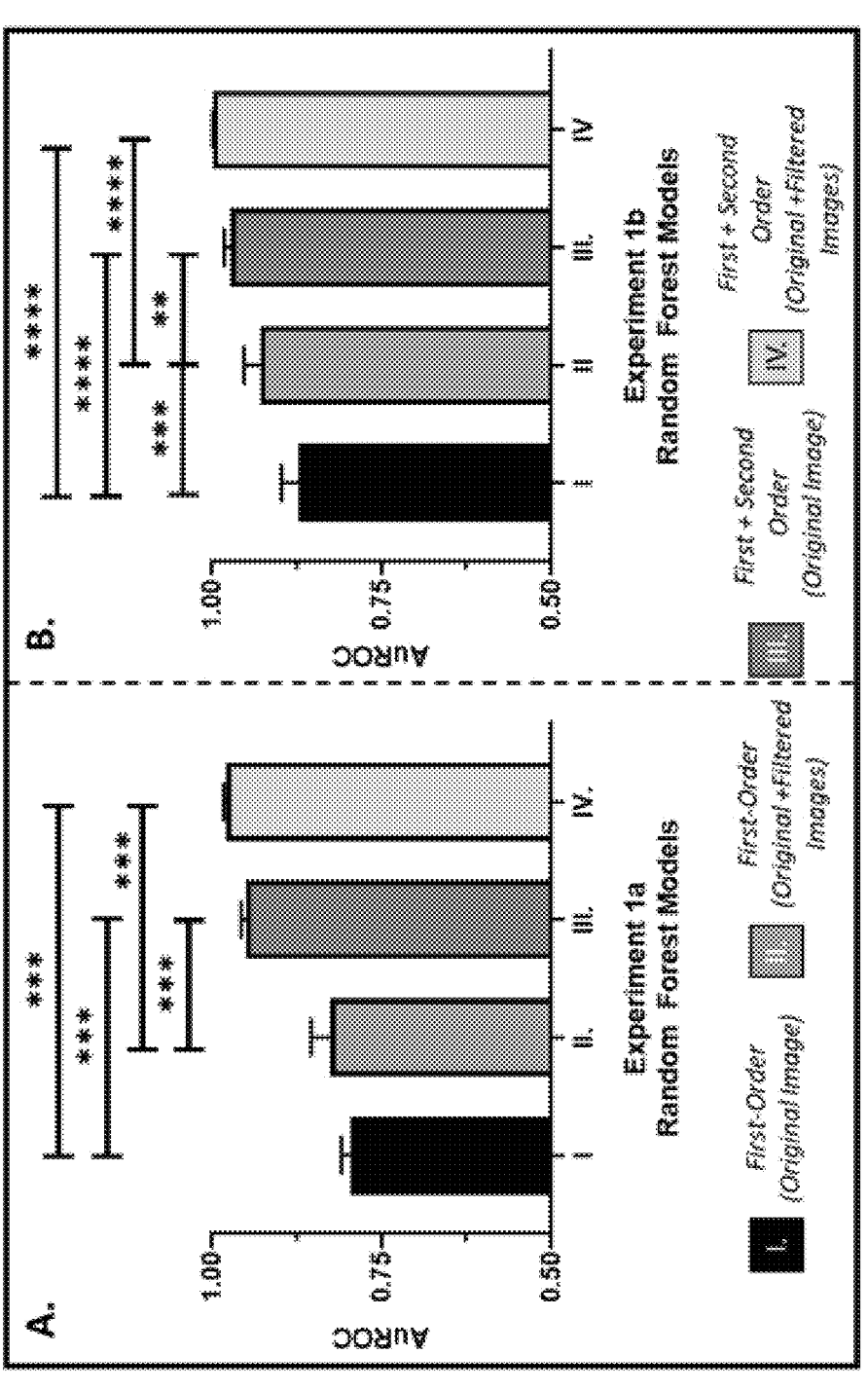
FIG. 29 shows AuROC values for four random forest models trained with different combinations of radiomic features for Experiments 1A and 1B.

FIG. 29 shows the Area under Receiver Operation Curve (AuROC) for the four random forest models in Experiments 1A and 1B. The statistical differences between each model was assessed using a one-way ANOVA. The asterisks in FIG. 29 correspond to the p-values, specifically "" (two asterisks) stands for "$p<0.01$", "*" (three asterisks) stands for "$p<0.001$", and "****" (four asterisks) stands for "$p<0.0001$".

In Experiment 1A, Model I (First Order—Image-Based) had an AuROC of $0.79\pm0.1$ which improved with the introduction of first order features from filtered images (Model II, First Order—Image+Filter based, AuROC: $0.83\pm0.001$). The inclusion of matrix-based radiomic features (Models III and IV) further improved classification performance.

In Experiment 1B, as described above, the tumour masks distinguished between areas of high FDG uptake (SUV values above the patient-specific $SUV_{50}$ value) and areas of low SUV uptake (SUV values below the patient-specific $SUV_{50}$ value). Of the four random forest models trained, Model I (First Order—Image-Based) had an AuROC of $0.87\pm0.12$, which improved with the introduction of first order features from filtered images—Model II (First Order—Image+Filter-Based) had an AuROC of $0.93\pm0.13$, $p<0.001$. As with Experiment 1A, the incorporation of matrix-based radiomic features (Models III, IV) further improved classification performance.

Experiments 1A and 1B have demonstrated that, using a labelled training set comprising a plurality of CT images and a corresponding plurality of functional feature identifiers labelling one or more functional features in a corresponding CT image, one is able to train a classification algorithm to learn features of the CT images that correspond to functional features labelled by the functional feature identifiers, and output a trained image segmentation model. More specifically, the particular Experiments 1A and 1B have demonstrated that classifier models may be trained to distinguish regions of FDG uptake (indicative of functional activity) from areas of no/negligible FDG uptake, and can further be trained to distinguish regions of high FDG uptake from regions of low FDG uptake.

In Experiment 2, the inventors investigated whether a Generative Adversarial Network (GAN) can be used to transform a CT image, in particular an NCT image, into a functional image dataset, in particular an SUV map (or more particularly an inverted SUV map).

GANs are an approach to generative modelling using deep learning methods, for example convolutional networks. GANS are a class of deep learning architectures whereby two networks train simultaneously, with one network focused on data generation (generator) and the other network focused on data discrimination (discriminator). The generator network and the discriminator network 'compete' against each other, learning the statistical distribution of the training data, which in turn enables the generator to generate new examples from the same distribution. A known dataset serves as the initial training data for the discriminator network. Training the discriminator involves presenting it with samples from the training dataset, until it achieves acceptable accuracy. The generator network trains based on whether it succeeds in fooling the discriminator.

The inventors have demonstrated that GANs can be used to generate/produce a simulated functional image dataset, in particular an inverted SUV map, from an input non-contrast computed tomography (NCT) image. Inverted SUV maps were chosen in place of SUV maps only because this is a view commonly used by physicians.

A conditional GAN (cGAN) is an extension to the GAN idea. In a conditional GAN, the generative model can be trained to generate new examples from the input domain, where the random vector from the latent space is provided with/conditioned by some additional value, such as a class value, a digit or so on. The discriminator model is also trained by being provided with both an input image that is real or fake and the additional input.

A cycle-GAN is an extension to the GAN idea. Traditionally, training an image-to-image translation model requires a dataset comprising many paired examples of input images and corresponding expected output images. A cycle-GAN is an approach to training image-to-image translation using the GAN model architecture, in which the generator models and discriminator models can be trained without the need for paired examples in the training data. A cycle-GAN may comprise two generator networks and two discriminator networks. One generator may take images from the first domain as input and output images for the second domain, and the second generator may take images from the second domain and generate images for the first domain. A first discriminator may determine the plausibility of the output image from the first generator and the second discriminator may determine the plausibility of the output image from the second network. Additionally, the output images from the first generator may be input to the second generator and vice versa in order to encourage cycle consistency—if an original input image is input to the first generator and the generated output image is input to the second generator, then it is desirable that the output from the second generator substantially matches the original image. Accordingly, a cycle-GAN may be thought of as two inter-related CGANS each comprising a generator and a discriminator, whereby each cGAN is trained to synthesize an image given an input image. A loss function is further used to update each of the cGANs based on cycle consistency. Cycle consistency loss compares an image input to the cycle-GAN with the generated output and updates the generator models in each training iteration.

Figure 30:
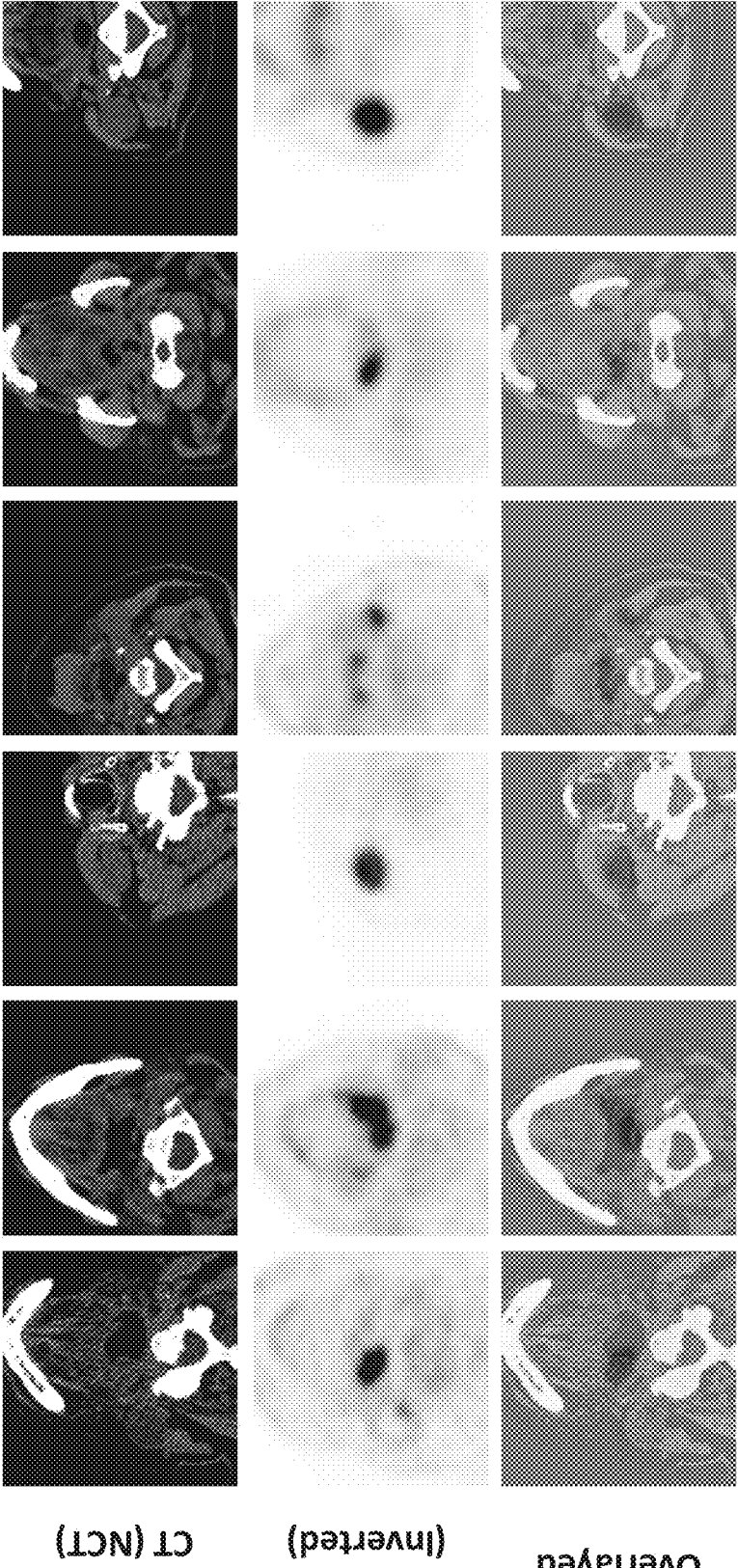
FIG. 30 shows six NCT images, six SUV images and the overlaid images.

In Experiment 2, a cycle-GAN was used for the NCT to inverted SUV image transformation task. In Experiment 2, the training data comprised 8,370 2D real NCT images and 8,370 2D real inverted SUV images. FIG. 30 shows some examples of such images, and additionally shows the over-laid images. The testing data comprised 3,931 2D real inverted NCT images and 3,931 2D real inverted SUV images. The number of NCT images was equal to the number of SUV images only because the images were taken from the paired dataset described above in relation to FIG. 23; however, the advantage of a GAN model is that the NCT images and SUV images need not be paired images.

Figure 31:
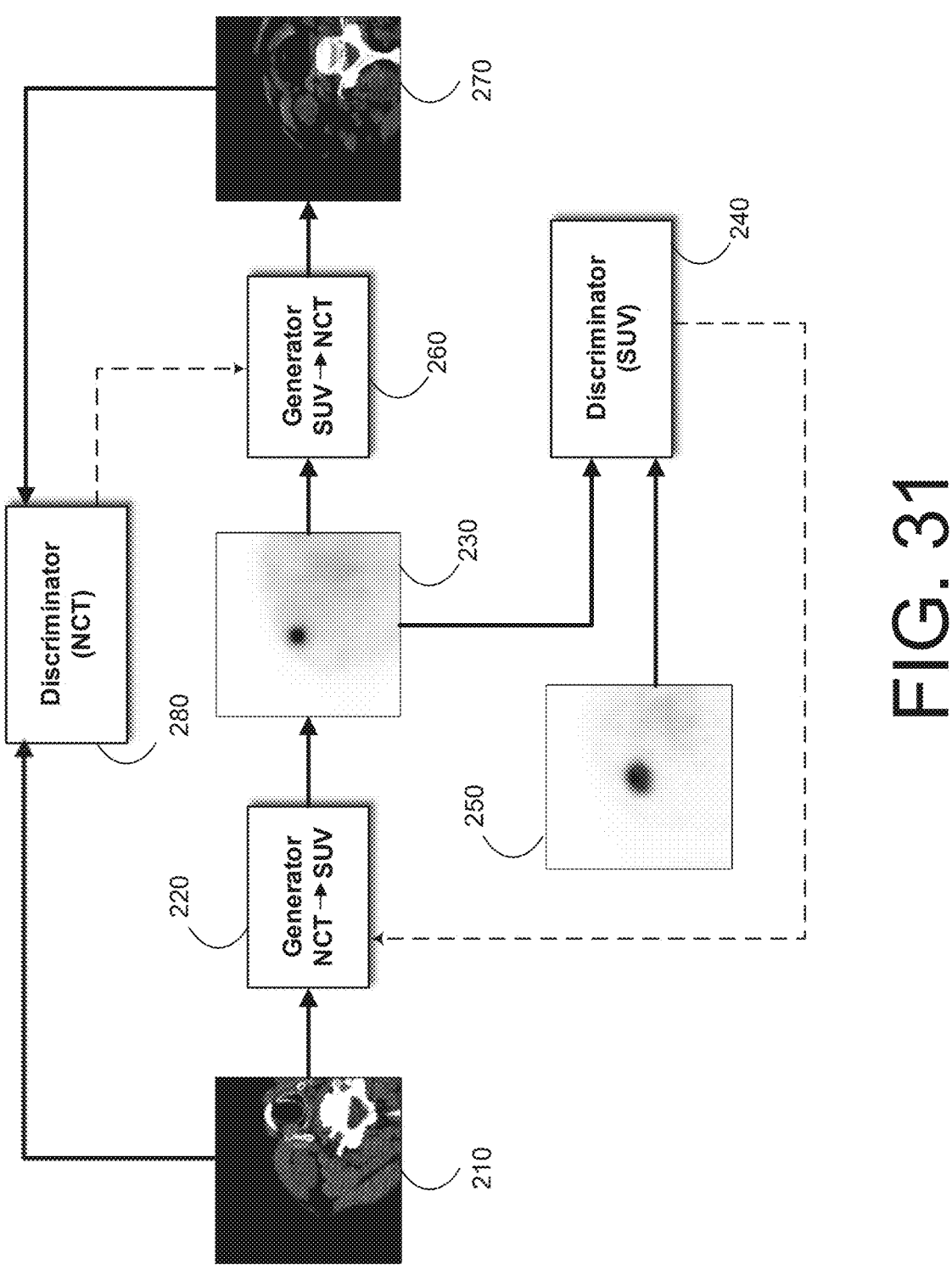
FIG. 31 shows an illustration of a cycle-GAN used in Experiment 2.

An illustration of the cycle-GAN is shown in FIG. 31. A real NCT image 210 is provided to a first generator network 220 for generating a simulated functional image dataset, in particular an inverted SUV image 230. The simulated functional image dataset 230 and real inverted SUV images 250 are provided to a first discriminator model 240 for classifying an image as a real inverted SUV image or a "fake" (simulated) inverted SUV image. Feedback from the first discriminator 240 is used to train the first generator network 220. Furthermore, the simulated functional image dataset 230 is also provided to a second generator network 260 for generating a simulated NCT image 270 from an input simulated inverted SUV image 230. The real NCT images 210 and the simulated NCT images 270 are provided to a second discriminator model 280 for classifying an image as a real NCT image or a "fake" (simulated) NCT image. Feedback from the second discriminator 280 is used to train the second generator network 260.

The first cGAN comprising the first generator and first discriminator components (220, 240 in FIG. 31) was explic-itly defined as a least-squares GAN. The least-squares GAN incorporates an additional least-squares loss function for the discriminator 240 which in turn improves the training of the generator model 220. The second cGAN comprising the second generator and second discriminator components (260, 280 in FIG. 31) was explicitly defined as a 70×70 pixel PatchGAN respectively. The PatchGAN analyses the image pairs, in 70×70 patches, and is trained to classify whether the image under question is "real" or "fake".

The cycle-GAN models were trained with a learning rate of $2.0 \times 10^{-5}$ for 200 epochs on overlapping 144×144 images located around the patient segmentation, which was derived to assess registration accuracy between the NCT and SUV images. Four networks (two generators and two discrimina-tors) were trained simultaneously and various loss functions were evaluated at each iteration to document model training. In addition to the loss metrics inherent to the networks, an identity mapping loss function and a cycle consistency loss function were included to ensure appropriate style transfer and regularization of the generator to allow for image translation. Model weights were saved every 10 epochs and intermediate model predictions were generated from the NCT images within the training cohort. The generated predictions were independently evaluated against the ground truth images to assess model training. During assessment, overlapping 144×144 images throughout the patient volume were transformed and a weighted average of the output slices was used to compile the generated 3D SUV map.

A 3-fold training platform was implemented for this NCT image to SUV map image transformation task. In each cohort the 298 patients of the TCIA dataset were designated as either for training, for validation, or for testing. The corresponding images for those patients were correspond-ingly designated as training data, validation data or testing data.

During model training, for each fold, the root mean squared error (RMSE) between the simulated and gold-standard (real) SUV map images in the validation cohorts decreased to plateau at 0.30±0.12. For the test data the RMSE between the simulated and genuine SUV maps for the first, second, and third cohorts were 0.40±0.14, 0.39±0.16, and 0.40±0.15 respectively.

Figure 32:
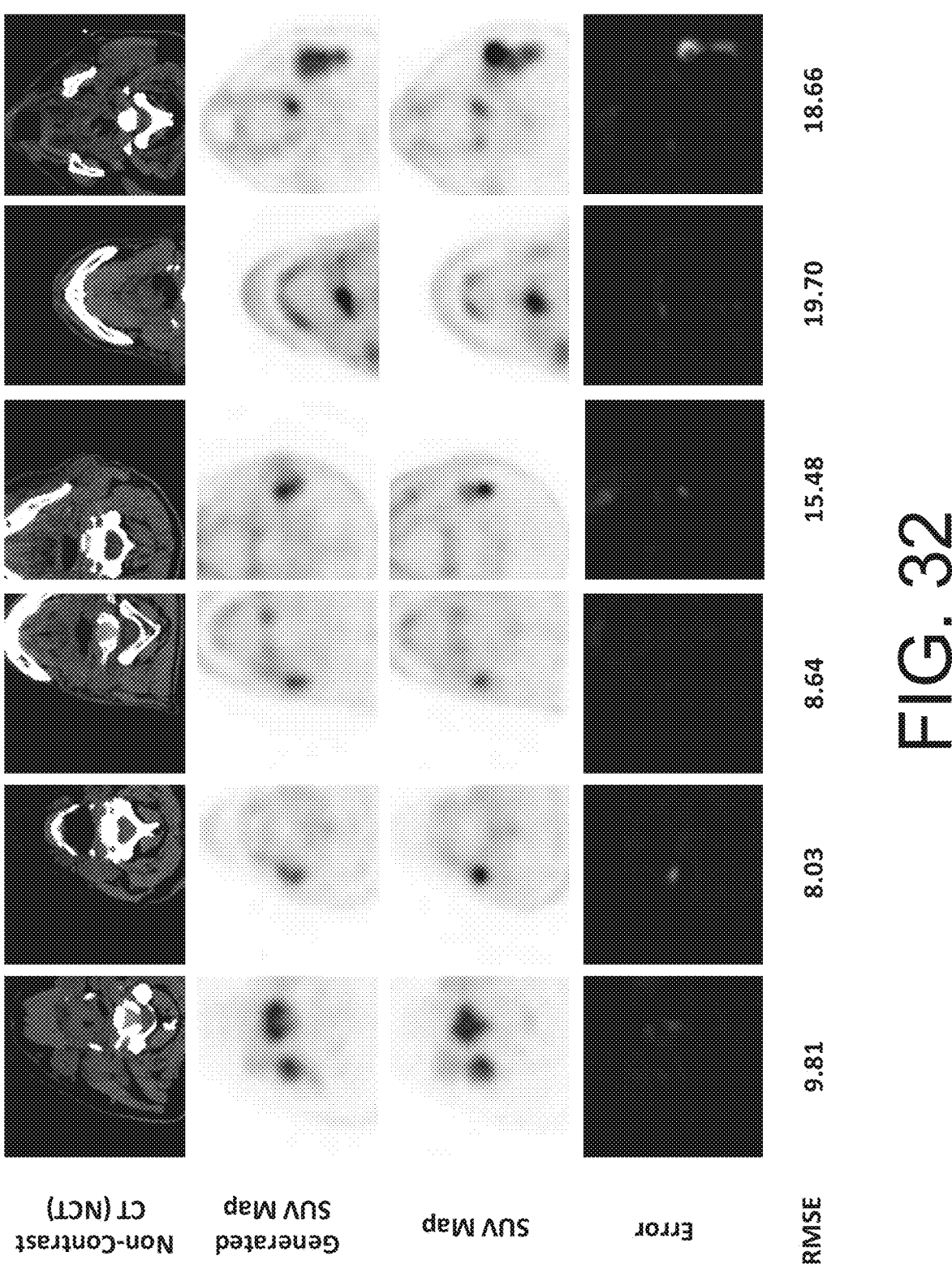
FIG. 32 shows six NCT images, the corresponding (ground truth) inverted SUV maps, the simulated SUV maps output from the trained cycle-GAN, and a visualisation of the errors.

FIG. 32 shows, for a selection of six test NCT images, the simulated SUV maps output from the cycle-GAN. The ground truth (real) inverted SUV maps are also shown. The error between the inverted SUV maps and the simulated SUV maps is visualized and is represented by the RMSE. The visualized error is the difference between the two sets of images and highlights the difference in pixel values. As can be seen, the cycle-GAN was able to generate simulated functional image datasets that closely approximated the "ground truth".

Figure 33:
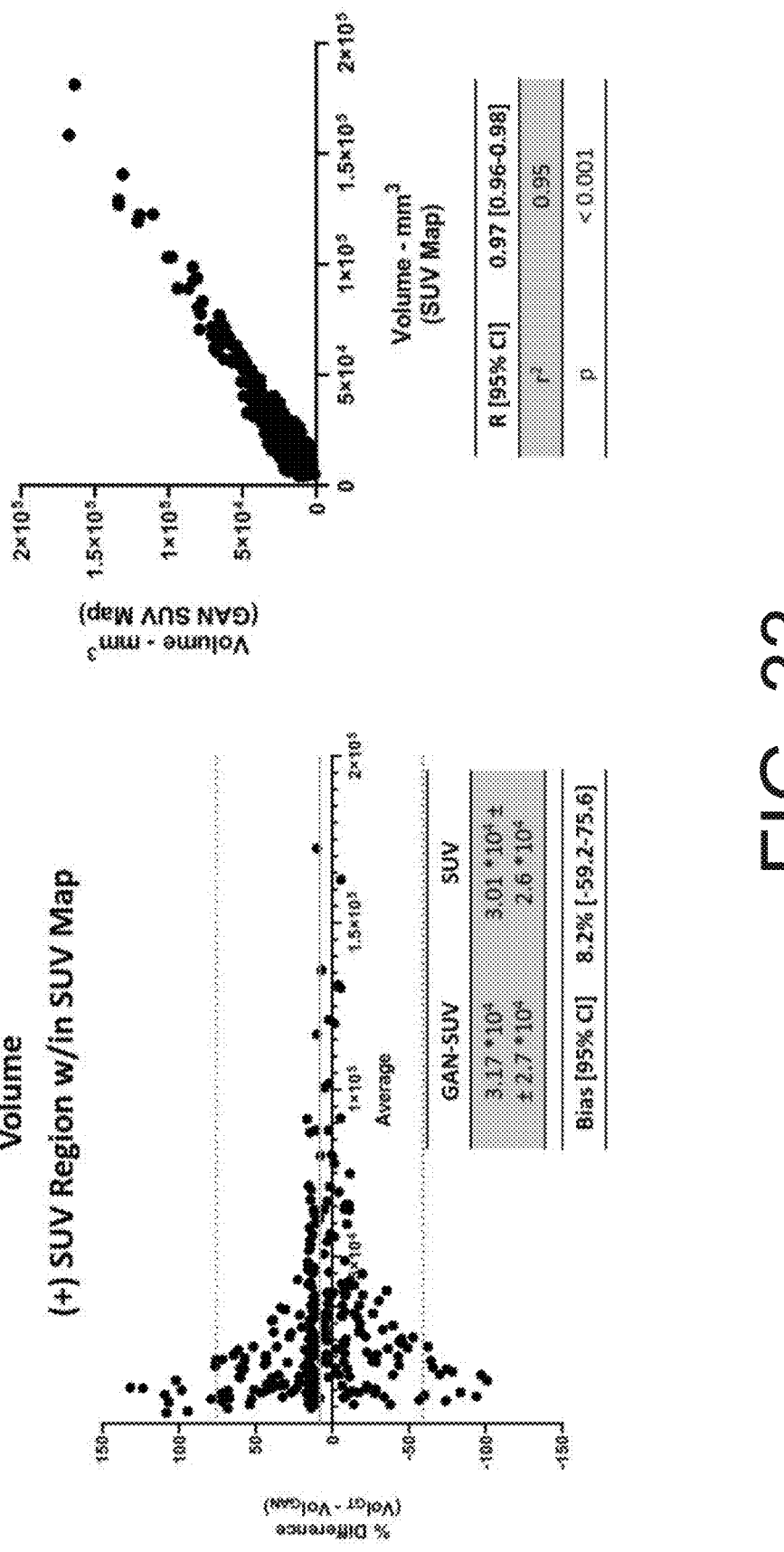
FIG. 33 shows a Bland-Altman plot comparing the tumour volume as indicated in the test inverted SUV images with the tumour volume as indicated in the simulated inverted SUV images, and a plot directly comparing the volumes.

The simulated SUV maps generated by the cycle-GAN and the real SUV maps were compared quantitatively to evaluate the success of the cycle-GAN. Mean $SUV_0$ (2.20±0.78), $SUV_{50}$ (5.95±2.15) and $SUV_{Max}$ (9.89±0.38) within the tumour regions of the generated maps was less than that of ground truth/gold standard SUV maps ($SUV_0$): 2.40±0.64, $SUV_{50}$): 6.62±1.71, $SUV_{Max}$: 9.98±0.15). Sub-sequently, the bias, as measured by Bland-Altman plot analysis was 11.7% [95% CI: −41.7-65.2%], 14.3% [95% CI: −40.5-69.2%] and 1.8% [95% CI: −9.7-12.1%]. These values suggest that the generated/simulated SUV map underestimates regional FDG uptake within the tumour regions. However, predicted tumour volume/burden per patient ($3.16 \times 10^4 \pm 2.73 \times 10^4$ mm$^3$) was similar to that of the gold standard ($3.01 \times 10^4 \pm 2.60 \times 10^4$ mm$^3$, p=0.51). A Bland-Altman plot comparing the percentage differences in tumour burden between the GAN-generated (simulated) SUV map and the gold-standard (real) SUV maps is shown in the left-hand chart of FIG. 33. The right hand chart of FIG. 33 shows that the estimated tumour volume (y-axis) against the tumour volume shown derived from the real SUV map (x-axis). The simulated SUV maps accordingly tended to underestimate metabolic activity but could still be used to differentiate healthy tissues from those with altered meta-bolic activity.

Figure 34:
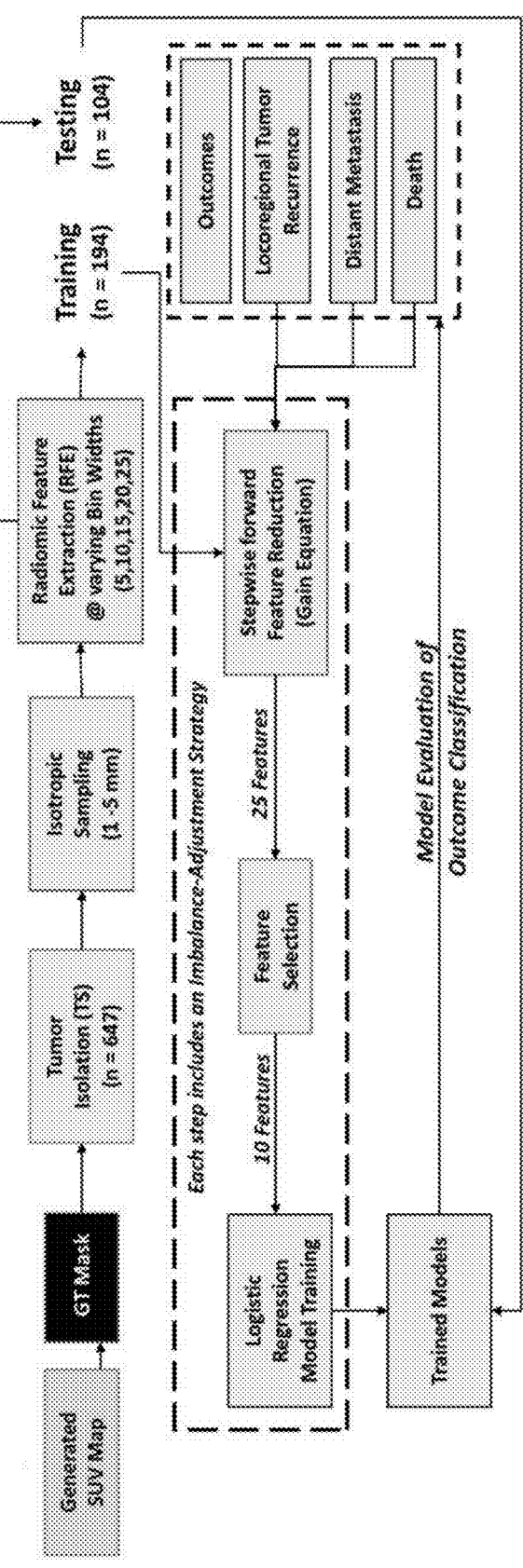
FIG. 34 illustrates a methodology used in training a logistic regression model to predict clinical outcomes from a simulated SUV map, and testing the trained model.
Figure 35:
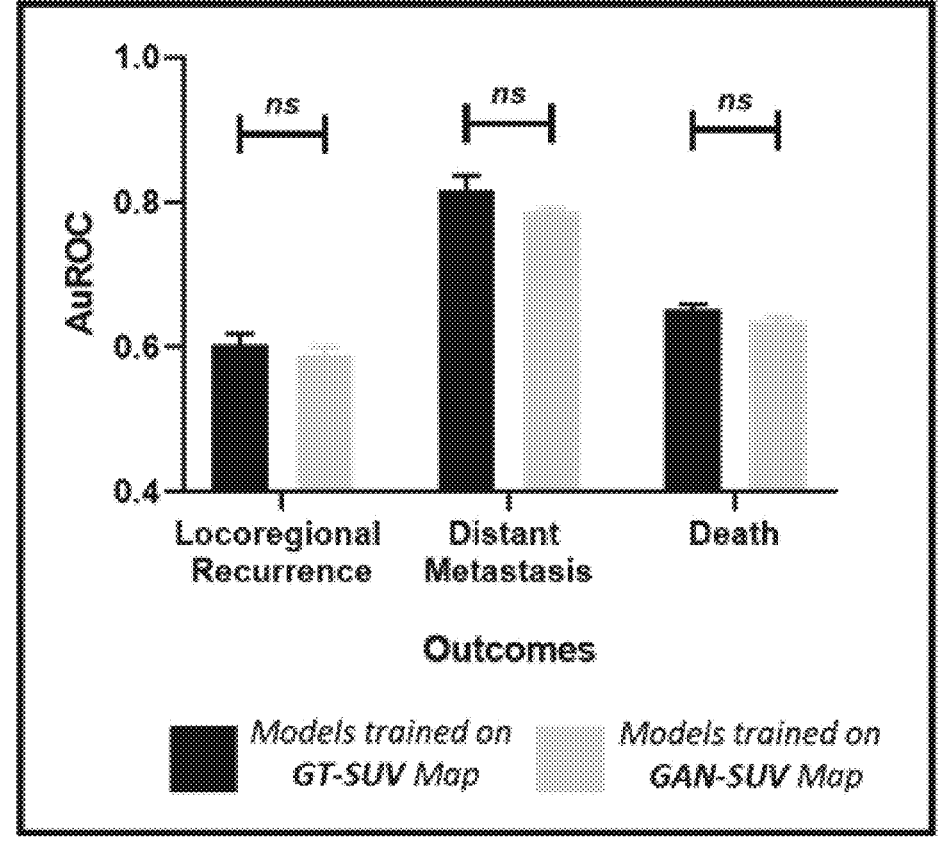
FIG. 35 shows a plot comparing the AuROC values for a model trained on simulated SUV images to a model trained on genuine SUV images.

The inventors subsequently investigated whether the simulated SUV maps output from the cycle-GAN were suitable for predicting clinical outcomes. Using the cycle-GAN generated SUV maps, the inventors constructed linear regression models to predict the clinical outcomes (tumour locoregional recurrence, tumour distant metastasis, sur-vival). The primary objective of this experiment was to compare the predictive accuracy using the cycle-GAN gen-erated SUV maps against the ground truth. FIG. 34 illus-trates the method used to train and test the linear regression models. A similar method was used to build and test linear regression models using the corresponding genuine/ground truth inverted SUV maps.

For each patient, a total of 2,150 radiomic features were extracted. The same training (n=194) and testing split (n=104) was implemented for model training and evalua-tion. For each set of features, predictive performance was estimated and the top 3 parsimonious models were chosen for each outcome. The selected parsimonious models for each feature set (1. Ground truth inverted SUV map "GT-SUV", and 2. cycle-GAN generated simulated inverted SUV Map "GAN-SUV") and each of the three outcomes was directly tested on the pre-defined testing set. Model perfor-mances between the simulated inverted SUV maps and that of the gold-standard was compared to assess the predictive capacity of the generated images.

Regions of high FDG uptake/SUV were isolated in the GAN-generated SUV map using the defined threshold-based segmentation method. 86 radiomic features (first+second order features) were extracted from both the GAN and GT SUV maps for each combination of image parameters (25). Data was separated into training (n=194) and testing cohorts (n=104) prior to feature reduction and selection for each outcome. Model outcomes based on ground truth SUV (GT-SUV) and cycle-GAN generated SUV (GAN-SUV) maps are displayed in FIG. 35.

Models trained to classify locoregional recurrence had a classification AuROC of 0.60±0.01 for the GT-SUV map, which was statistically similar to that of the GAN-SUV map (AuROC: 0.59±0.02, p=0.15). For classification of distant metastasis, the model trained on the GT-SUV map (AuROC: 0.82±0.02) outperformed that of the GAN-SUV map (AuROC: 0.79±0.01, p=0.10); however the difference was not statistically significant. Finally, models trained to classify patient death from radiomic features extracted from the GT-SUV maps (AuROC: 0.63±0.01) were similar in performance to that trained on radiomic features extracted from the GAN-SUV map (AuROC: 0.62±0.02, p=0.13).

Although the generated SUV maps underestimated the metabolic activity within the tumour region relative to the gold-standard SUV maps, they were able to sufficiently predict clinical outcomes. These results support the ability to use a generative model trained as part of a GAN to generate simulated functional image datasets from a non-contrast CT image to obtain clinically relevant representations of metabolic activity within patients diagnosed with HNSCCs.

Experiments 1A, 1B and 2 demonstrated that there are subtle differences within a NCT image that can distinguish regions of increased metabolic activity (hotspots on a PET scan) from regions with negligible activity. That is, NCT images contain enough information to identify functional activity.

An advantage of PET imaging is its ability to identify abnormal metabolic activity in organs that do not show an abnormal appearance based on morphological criteria. NCT images are typically used to supplement PET images by providing a method to anatomically localize these metabolic hotspots. However, abnormal tissues at the molecular level are significantly different from health tissues, in terms of ultrastructure, tissue organization and metabolic activity. These altered characteristics have been shown to be present prior to the alteration in morphological structure at the macro-scale and may reflect changes in the tissue's attenuation coefficient.

As has been demonstrated in the experiments outlined above, the differences between these visually indistinct regions can be captured using a combination of first- and second-order radiomic features. In Experiments 1A and 1B, it was demonstrated that there are significant radiomic differences between regions of negligible, low, and high FDG activity in the NCT image. These differences support the validity of this image transformation task.

Experiment 2 demonstrated that a generative network is able to robustly extract the subtle differences between soft-tissue components in patients diagnosed with head and neck squamous cell carcinoma and generate a visualisation of metabolic activity. Experiment 2 showed that a trained cycle-GAN enables the visualisation of metabolic activity in CT scans without the need to obtain a paired PET image. Volume of the tumour hot spot was similar between the generated and gold-standard SUV images. This suggests that the generative method is sufficiently able to differentiate healthy tissues from those with altered metabolic activity.

Figure 36:
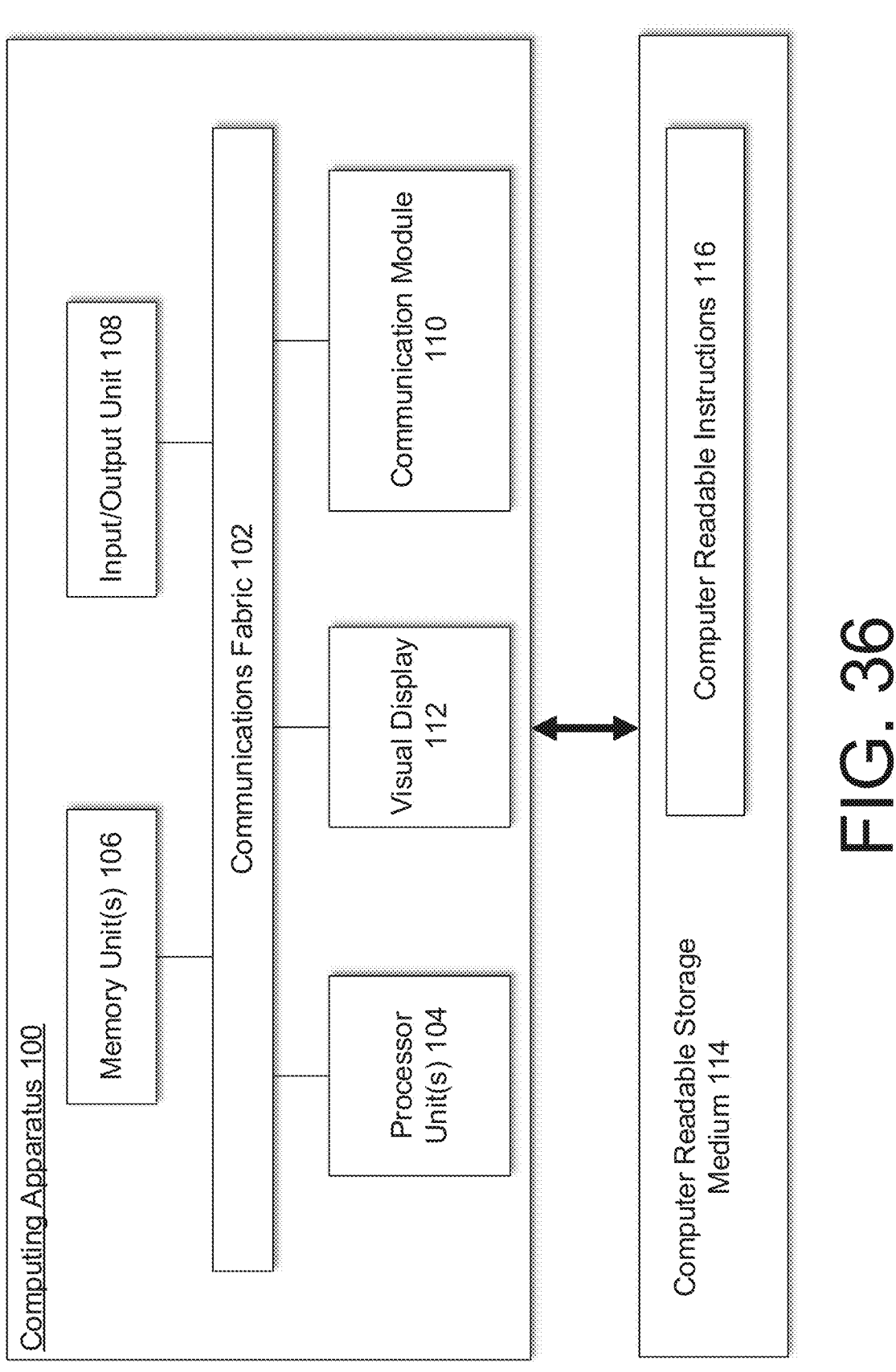
FIG. 36 shows a computing apparatus and computer readable storage medium.

FIG. 36 depicts a block diagram of a data processing system/computing device/computing apparatus 100 in which illustrative embodiments may be implemented. Computing device 100 is an example of a computer, in which computer usable program code or instructions implementing the processes may be located. In this example, data processing system 100 includes communications fabric 102, which provides communications between processor unit(s) 104, memory unit(s) 106, input/output unit 108, communications module 110, and display 112.

The one or more processing units/processors 104 are configured to execute instructions for software that may be loaded into the memory 106. Processor unit(s) 104 may be a set of one or more processors or may be a multi-processor core, depending on the particular implementation. Further, processor unit(s) 104 may be implemented using one or more heterogeneous processor systems in which a main processor is present with secondary processors on a single chip. Processor unit(s) 104 may include a graphical processing unit. GPUS are useful for training a neural network or other machine learning model.

The one or more memory unit(s) 106 may comprise any piece of hardware that is capable of storing information, such as, for example, data, program code in functional form, and/or other suitable information either on a temporary basis and/or a permanent basis. The one or more memory units 106 may include, for example, a random access memory or any other suitable volatile or non-volatile storage device. The one or more memory units may include a form of persistent storage, for example a hard drive, a flash memory, a rewritable optical disk, a rewritable magnetic tape, or some combination thereof. The media used for persistent storage may also be removable. For example, the one or more memory units 106 may include a removable hard drive.

Input/Output unit 108 enables the input and output of data with other devices that may be in communication with the computing device 100. For example, input/output unit 108 may provide a connection for user input through a keyboard, a mouse, and/or other suitable devices. The input/output unit 108 may provide outputs to, for example, a printer.

Communications module 110 enables communications with other data processing systems or devices. The communications module 110 may provide communications through the use of either or both physical and wireless communications links.

Instructions for the applications and/or programs may be located in the one or more memory units 106, which are in communication with processor unit 104 through communications fabric 102. Computer-implementable instructions may be in a functional form on persistent storage in the memory unit(s) 106, and may be performed by processor unit 104.

These instructions are referred to as program code, computer usable program code, or computer-readable program code that may be read and executed by a processor in processor unit 104. The program code in the different embodiments may be embodied on different physical or tangible computer-readable media.

In FIG. 36, computer-readable instructions/program code 116 is located in a functional form on computer-readable storage medium 114 that is selectively removable and may be loaded onto or transferred to computing device 100 for execution by processor unit(s) 104. A computer-readable storage medium may be, for example, but not limited to, an electronic, magnetic, optical, electromagnetic, infrared, or semiconductor system, apparatus, device, or any suitable combination thereof.

Alternatively, computer-readable instructions 116 may be transferred to computing device 100 from computer-readable storage medium 114 through a communications link to communications module 110 and/or through a connection to input/output unit 108. The communications link and/or the connection may be physical or wireless.

In some illustrative embodiments, computer-implementable instructions 116 may be downloaded over a network to the memory unit(s) 106 from a remote device for use with computing device 100. For instance, computer-implementable instructions stored in a remote server may be downloaded over a network from the server to the device 100.

The skilled person would appreciate that the architecture described above in relation to FIG. 36 is not intended to provide limitations on the computing devices with which the methods described herein may be implemented. Instead, the skilled person would appreciate that other architectures may be applied. For example, the computing device may include more or fewer components.

A computing device such as computing device 100 may be used to perform any of the methods described herein.

As has been demonstrated above in relation to FIGS. 9A-22F, it is possible to compare radiomic feature values of a target region shown in a CT image with threshold radiomic feature values to determine functional features within the target region.

Figure 37:
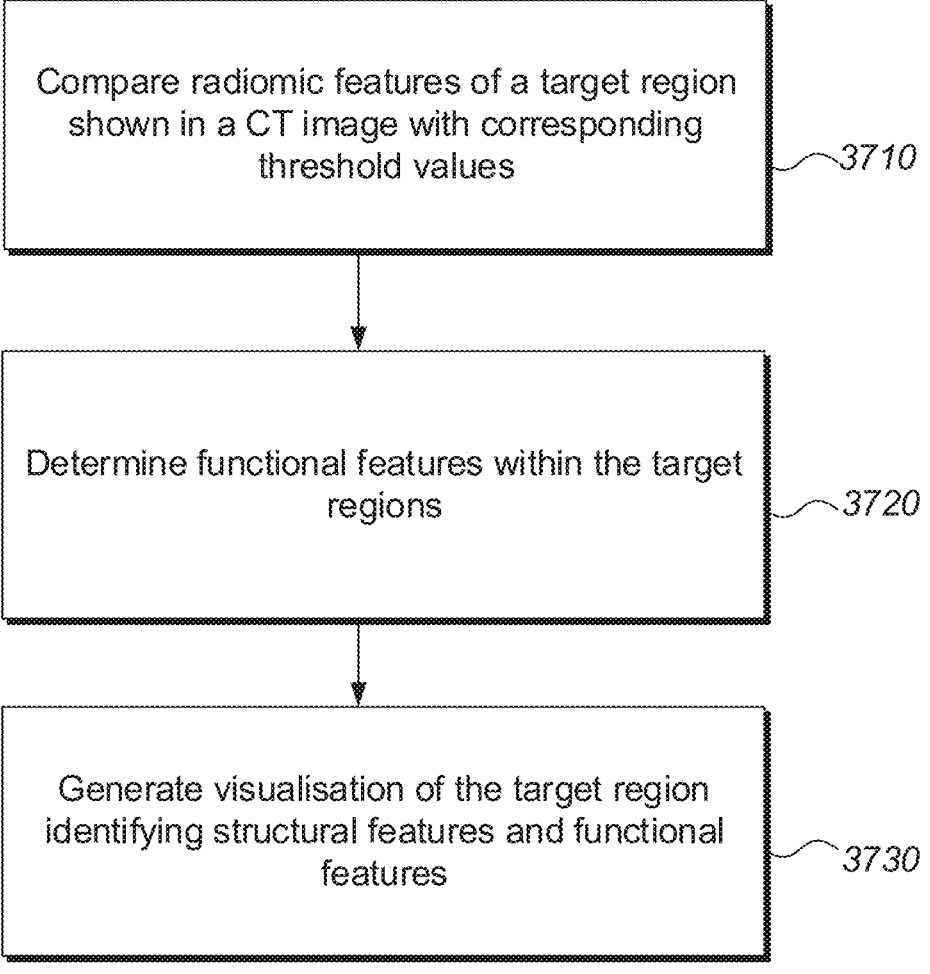
FIG. 37 shows a flowchart of a method for identifying structural features and functional features from a CT image.

A general method for identifying structural features and functional features from a computed tomography (CT) image is now described in relation to the flowchart shown in FIG. 37. The method may be performed by any suitable computing apparatus, such as the computing apparatus 100 described in relation to FIG. 36. For example, the processor unit(s) 104 of computing apparatus 100 may execute instructions stored in memory 106 or in a computer readable storage medium 114 in connection with the computing apparatus 100 to perform the method illustrated in FIG. 37.

The CT image identifies one or more structural features in a target region of a subject. For example, the CT image may indicate blood vessels, lymph nodes, bones and/or other tissue. The CT image may be a CCT image or may be a NCT image.

At 3710, the method comprises comparing radiomic feature values of a target region shown in the CT image with corresponding threshold values.

For example, the radiomic values can be compared against threshold radiomic feature values known to indicate a lack of the functional activity being investigated. For example, with reference to FIGS. 9A-22F, the radiomic feature values for metastatic lymph nodes may be compared with threshold radiomic feature values that are known to indicate a lack of functional activity in a lymph node. Comparing the radiomic feature values with corresponding thresholds may comprise checking for at least a 10-fold difference or at least a 20-fold difference between the radiomic feature values and the threshold values.

Comparing radiomic feature values of a target region shown in the CT image with corresponding threshold values may comprise, for example, dividing the target region of the CT image into several subregions, extracting radiomic feature values for each subregion, and then comparing the radiomic feature values for each subregion against the appropriate threshold values.

At 3720, the method comprises determining, from the comparison, functional features within the target region. For example, if one or more radiomic feature values of interest for a subregion of the image exceeds a threshold value, then a determination may be made that the subregion corresponds to an area of functional activity. In some other examples, the radiomic feature value(s) being less than a threshold value may indicate functional activity. By determining, for each subregion, whether or not that subregion corresponds to an area of functional activity in the subject, one can build up an indication as to which areas of the CT image correspond to functional activity.

For example, as demonstrated above in relation to FIGS. 9A-22F, it can be determined whether a lymph node would test positive for FDG-uptake.

At 3730, the method comprises generating, using the determined functional features, a visualisation of the target region identifying the functional features and the structural features.

For example, the visualisation may comprise a simulated PET scan image or simulated PET-CT scan which indicates the structural features that were identifiable from the original CT scan and also further functional features determined from the radiomic analysis. In some examples, the structural features may also be identified by a radiomic analysis of the CT image.

Figure 38:
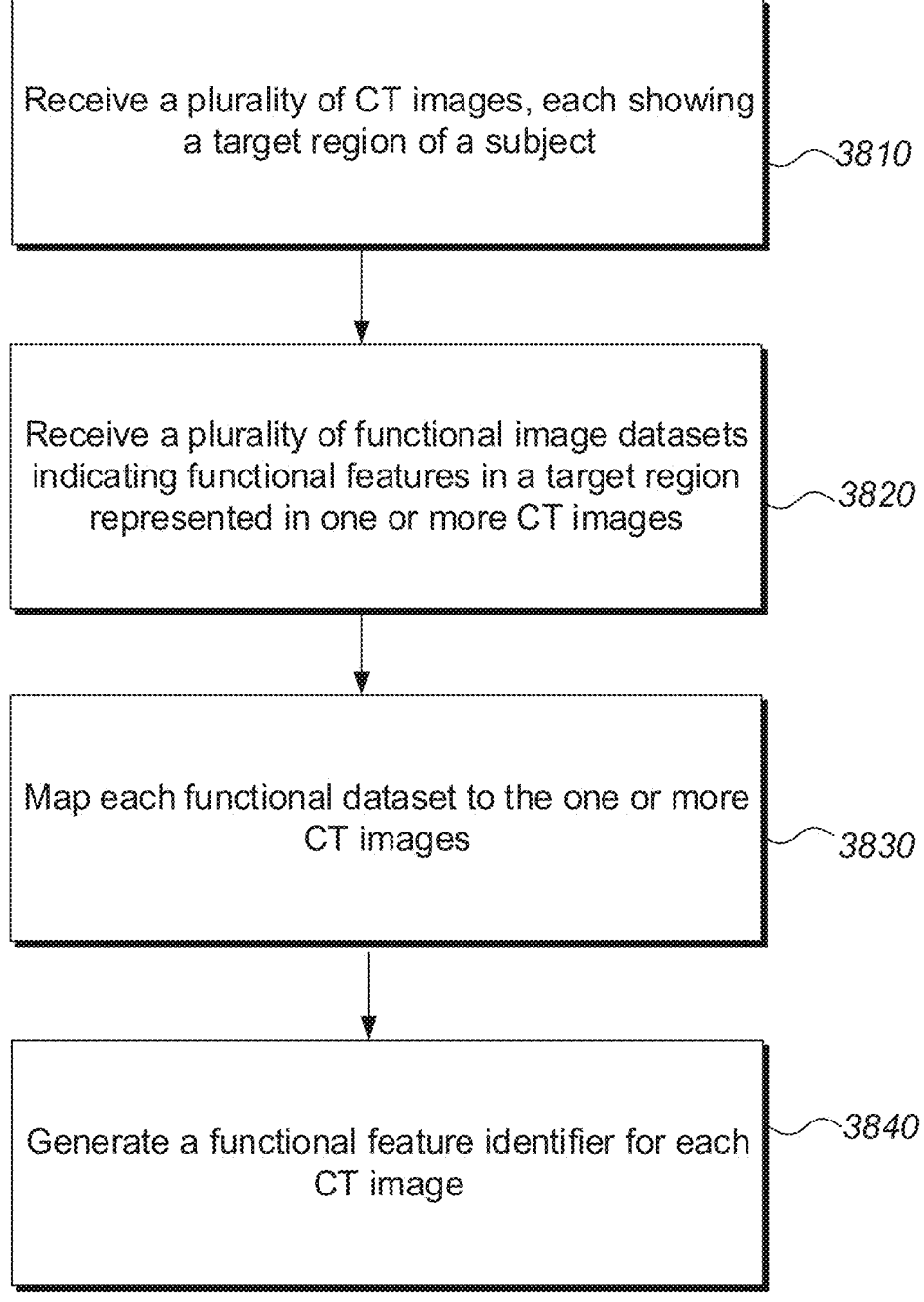
FIG. 38 shows a flowchart of a method for establishing a labelled training set for training a machine learning image segmentation algorithm or a machine learning classification algorithm.

As has been demonstrated above in relation to Experiments 1A and 1B, it is possible to train a random forest algorithm to identify functional features in a NCT image. More generally, it has been demonstrated that, given an appropriate training set, one can train a classification algorithm to identify functional features in a CT image. FIG. 38 shows a flowchart of a general method for establishing a labelled training set for training a classification algorithm to identify functional features in a CT image. The classification algorithm may be, for example, a random forest algorithm. The method may be performed by any suitable computing apparatus, such as the computing apparatus 100 described in relation to FIG. 36. For example, the processor unit(s) 104 of computing apparatus 100 may execute instructions stored in memory 106 or in a computer readable storage medium 114 in connection with the computing apparatus 100 to perform the method illustrated in FIG. 38.

At 3810, the method comprises receiving a plurality of CT images, each CT image showing a target region of a subject. The CT images may be contrast-enhanced CT images or may be non-contrast CT images. Several of the CT images may pertain to the same subject. Several of the CT images may pertain to the same target region.

Optionally, some further processing of the CT images may be performed. For example, as discussed above in relation to Experiments 1A and 1B, the CT images may be manipulated in order to remove artefacts such as the table on which the subject lays during the scan.

At 3820, the method comprises receiving a plurality of functional image datasets indicating functional features in a target region represented in one or more CT images of the plurality of CT images. The functional image datasets may comprise PET scan data, for example FDG-PET scan data. The functional image datasets may comprise SUV maps, which may have been derived from PET images.

Optionally, some further processing of the functional image datasets may be performed. For example, as discussed above in relation to Experiments 1A and 1B, the original PET scan images were transformed into SUV maps.

It is noted that stages 3810 and 3820 may occur concurrently or consecutively, and that the functional image datasets may be received before the CT images.

At 3830, each functional image dataset is mapped to the one or more CT images showing the target region comprising the functional activity. Mapping the functional image dataset may comprise adapting the underlying imaging data to substantially align with the corresponding CT image. For example, the mapping may comprise orienting a PET image to substantially align with a CT image, or may comprise scaling a PET image to substantially align with a CT image. "Mapping" may be understood to mean any digital transformation. In particular, mapping the plurality of functional image datasets to the plurality of CT images may be understood to mean performing any suitable image transformations the CT image or to the functional image dataset such that features of the functional image dataset can be mapped to appropriate regions of the CT image.

At 3840, the method comprises generating, for each CT image, a corresponding functional feature identifier using the plurality of mapped functional image datasets, each functional feature identifier labelling one or more functional features in the target region shown in the corresponding CT image. A functional feature identifier may be understood to mean an identifier of functional activity, for example a set of radiomic values distinguishing between functional activity and otherwise. A functional feature identifier may comprise a filter or a segmentation mask. For example, as discussed above in relation to Experiments 1A and 1B, the functional feature identifiers may comprise segmentation masks such as tumour masks identifying the functional activity.

The labelled training set includes pairs of CT images and functional feature identifiers, each pair comprising a CT image and a corresponding functional feature identifier.

The method may further comprise expanding the training set by applying transformations to the CT images and corresponding functional feature identifiers (i.e. adjusting the sheer and/or divergence) in order to further diversify the training set and therefore to improve the ability of the classification algorithm to learn. Throughout this specification, reference to a training set comprising CT images and functional feature identifiers may be understood also to refer to such digitally transformed/augmented expanded datasets.

The term "training set" as used herein is understood to mean the dataset obtained from a plurality of CT images and functional image datasets of multiple patients or the same patient which is used to train a machine learning algorithm to label or otherwise identify the functional features of a CT image. For example, a contrast CT scan of a subject would ordinarily generate several CT images of that subject. Likewise, a PET scan may generate several PET images of the subject. In establishing the training set, one or more of such images for the patient may be used. Additionally, one or more CT images and one or more PET images from at least one further patient may also be used. The training set may be established from CT scan data for many patients, with many CT images for each patient, and may be established from functional image datasets for many patients.

The classification algorithm may learn by receiving the CT image as input and evaluating the CT image with the functional feature identifier, for example by comparing the resultant output to the functional feature identifier.

FIG. 39 shows a flowchart of a general method for training a machine learning classification algorithm to identify functional features from a computed tomography (CT) image. The classification algorithm may be, for example, a random forest algorithm. The method may be performed by any suitable computing apparatus, such as the computing apparatus 100 described in relation to FIG. 36. For example, the processor unit(s) 104 of computing apparatus 100 may execute instructions stored in memory 106 or in a computer readable storage medium 114 in connection with the computing apparatus 100 to perform the method illustrated in FIG. 39.

At 3910, the method comprises receiving a labelled training set comprising a plurality of CT scan images and a plurality of functional feature identifiers. The CT images may be contrast-enhanced CT images or may be non-contrast CT images. Several of the CT images may pertain to the same subject. Several of the CT images may pertain to the same target region. The functional feature identifiers may comprise, for example, segmentation masks. The labelled training set may be derived according to a method such as that described in relation to FIG. 38.

At 3920, the method comprises extracting, from each CT image, radiomic feature values for a set of radiomic features.

At 3930, the method comprises training a classification algorithm, using the extracted radiomic feature, to learn features of the CT images that correspond to functional features identified by the functional feature identifiers.

At 3940, the method comprises outputting a trained classification model for identifying a functional feature in a CT image.

FIG. 40 shows a flowchart of a general method for identifying one or more functional features in a computed tomography (CT) image showing a target region of a subject. The classification algorithm may be, for example, a random forest algorithm or a linear regression algorithm. The method may be performed by any suitable computing apparatus, such as the computing apparatus 100 described in relation to FIG. 36. For example, the processor unit(s) 104 of computing apparatus 100 may execute instructions stored in memory 106 or in a computer readable storage medium 114 in connection with the computing apparatus 100 to perform the method illustrated in FIG. 40.

At 4010, the method comprises, for each of a plurality of subregions of the CT image, extracting radiomic feature values for a set of radiomic features.

At 4020, the method comprises providing the radiomic feature values to a trained classification model trained to take as input radiomic feature values and to output a classification of a functional activity status of the subregion. For example, with reference to Experiment 1A described further above, the classification model may be trained to classify a subregion as being associated with functional activity or as not being associated with functional activity. For example, with reference to Experiment 1B described further above, the classification model may be trained to classify a subregion as being associated with high functional activity or as being associated with low functional activity.

The classification algorithm may have been trained according to the method described above in relation to FIG. 39.

At 4030, the method comprises identifying function features in the target region of the subject. For example, each subregion may be classified by the classification algorithm as being associated with functional activity or not, and by combining the classifications of all subregions, a larger scale view of functional activity may be formed. The method may further comprise, for example, outputting a visualisation of the target region of the CT image, the visualisation indicating functional features in the target region as defined by the classifications of the various subregions.

It will be noted that the training set, comprising paired CT images and functional feature identifiers, output by the method described above in relation to FIG. 38 may be used to train other types of machine learning algorithm. For example, the training set may be used to train a machine learning image segmentation algorithm, particularly if the functional feature identifiers comprise segmentation masks indicating functional activity.

Figure 41:
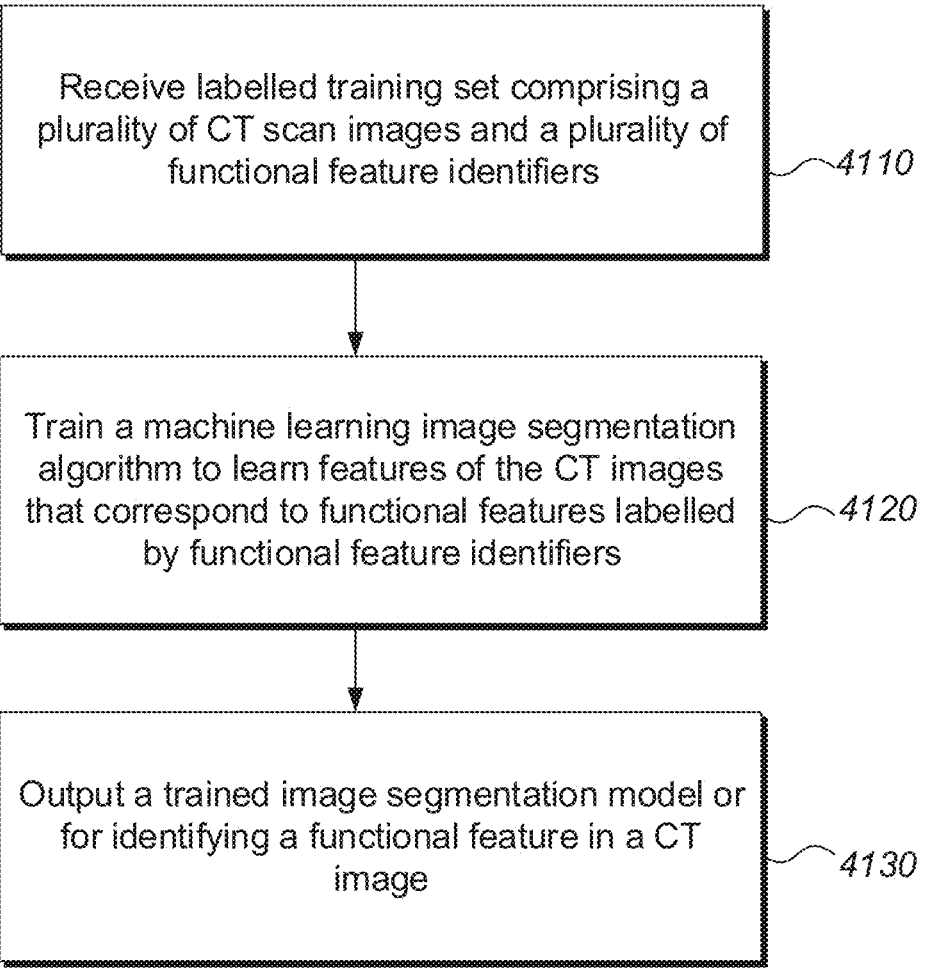
FIG. 41 shows a flowchart of a method for training a machine learning image segmentation algorithm.

FIG. 41 shows a flowchart of a general method for training a machine learning image segmentation algorithm to identify functional features from a computed tomography (CT) image.

At 4110, the method comprises receiving a labelled training set for the machine learning image segmentation algorithm. The labelled training set comprises a plurality of CT images, each CT image of the plurality of CT images representative of a target region of a subject. The labelled training set further comprises a corresponding plurality of functional feature identifiers, each functional feature identifier labelling at least one functional feature in a corresponding CT image of the plurality of CT images. The labelled training set may be derived according to a method such as that described in relation to FIG. 38.

At 4120, the method comprises training a machine learning image segmentation algorithm, using the plurality of CT images and the corresponding plurality of functional feature identifiers, to learn features of the CT images that correspond to functional features labelled by the functional feature identifiers, and output a trained image segmentation model.

The machine learning image segmentation algorithm may be any suitable machine learning image segmentation algorithm. For example, the machine learning image segmentation algorithm may comprise a neural network. For example, the machine learning image segmentation algorithm may comprise a convolutional neural network. The machine learning image segmentation algorithm may be trained by minimising a cost function involving the segmentation mask information ("ground truth") and the output of the final layer of the network. The cost function may comprise any suitable cost function such as a quadratic cost function, a cross-entropy cross function, a log-likelihood cost function. The minimisation may be performed for example by gradient descent, stochastic gradient descent or variations thereof, using backpropagation to adjust weights and biases within the neural network accordingly.

Training may involve the use of further techniques known to the skilled person, such as regularization. Mini-batch sizes and numbers of epochs may be selected and fine-tuned during training. The neural network may comprise several layers of neurons (which may be, for example, perceptrons, sigmoid neurons, tan h neurons, or rectified linear units/ rectified linear neurons), and may include one or more convolution layers, and may include one or more maxpool layers, and may include a soft-max layer.

At 4130, the method comprises outputting the trained image segmentation model usable for identifying a functional feature in a CT image. A trained image segmentation model may accordingly be understood to include all information determined in training. For example, the trained image segmentation model may include the complete collection of weights and biases for neurons established during training and details of hyperparameters such as the learning rate and mini-batch size.

The image segmentation model may comprise a generative model that may take, for example, a CT image as input and output a simulated functional image dataset indicating one or more functional features in the target region shown in the input CT image. For example, the simulated functional image dataset may comprise a visualisation of the target region identifying the functional features. For example, the visualisation may comprise a simulated PET scan image, a simulated PET-CT scan image, or a simulated SUV image.

Figure 42:
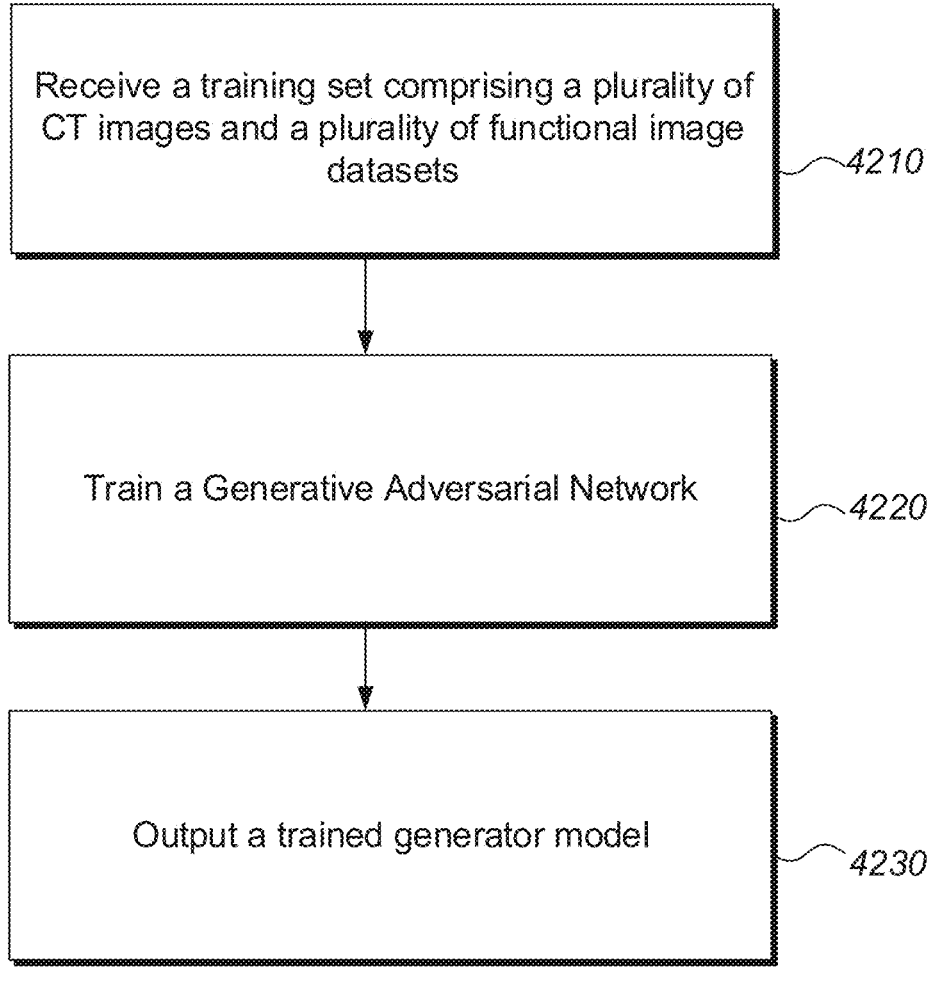
FIG. 42 shows a flowchart of a method for training a GAN.

As has been demonstrated above in relation to Experiment 2, it is possible to train a generative adversarial network (GAN) and output a generator model to translate an input NCT image into a simulated SUV or simulated inverted SUV map suitable for identifying functional features in the NCT image. More generally, it has been demonstrated that, given an appropriate training set, one can train a GAN to translate an input CT image into a simulated functional image dataset indicating one or more functional features in a target region represented in the input CT image. FIG. 42 shows a flowchart of a general method for training a generative adversarial network (GAN) to generate a simulated functional image dataset from a computed tomography (CT) image. The method may be performed by any suitable computing apparatus, such as the computing apparatus 100 described in relation to FIG. 36. For example, the processor unit(s) 104 of computing apparatus 100 may execute instructions stored in memory 106 or in a computer readable storage medium 114 in connection with the computing apparatus 100 to perform the method illustrated in FIG. 42. The GAN may comprise one or more generator networks and one or more discriminator networks. For example, the GAN may comprise a conditional GAN having one generator network and one discriminator network. The GAN may comprise a cycle-GAN having two generator networks and two discriminator networks.

At 4210, the method comprises receiving a plurality of CT images and a plurality of functional image datasets.

The CT images may be contrast-enhanced CT images or may be non-contrast CT images. Several of the CT images may pertain to the same subject. Several of the CT images may pertain to the same target region.

The plurality of functional image datasets may comprise PET images. The plurality of functional image datasets may comprise SUV or inverted SUV images.

The plurality of functional image datasets may or may not be related to the CT images. For example, in Experiment 2, the functional image datasets (in that example, inverted SUV maps) corresponded to NCT images, but this was due to the initial dataset used. A GAN does not require the CT images and the functional image datasets to correspond to one another.

At 4220, the method comprises training the GAN. Training the GAN comprises training the generator network, using the plurality of CT images and feedback from the discriminator network, to generate simulated functional image datasets. Training the GAN further comprises training the discriminator network, using the generated simulated functional image datasets and the plurality of functional image datasets, to classify received image datasets as simulated functional image datasets or genuine functional image datasets, and to provide feedback to the generator network.

At 4230, the method comprises outputting a trained generator model to translate an input CT image to a simulated functional image dataset indicating one or more functional features in the target region shown in the input CT image.

Figure 43:
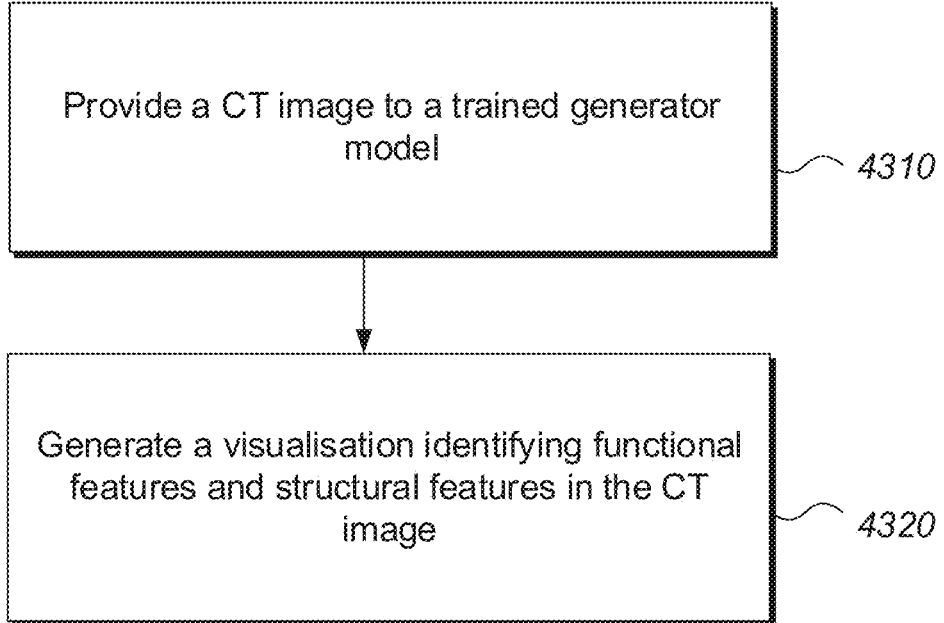
FIG. 43 shows a flowchart of a method for identifying one or more functional features in a CT image using a trained generator model.

FIG. 43 shows a flowchart of a method for identifying functional features in an computed tomography (CT) image. The method may be performed by any suitable computing apparatus, such as the computing apparatus 100 described in relation to FIG. 36. For example, the processor unit(s) 104 of computing apparatus 100 may execute instructions stored in memory 106 or in a computer readable storage medium 114 in connection with the computing apparatus 100 to perform the method illustrated in FIG. 43.

At 4310, the method comprises providing the CT image to a trained generator model, the trained generator model trained to learn features of CT images that correspond to areas of functional activity.

The generator model may have been trained as part of a GAN. For example, the generator model may have been trained using a method as described above in relation to FIG. 42.

The generator model may have been trained as an image segmentation algorithm, for example as described above in relation to FIG. 41.

At 4320, the method comprises generating, using the trained generator model, a visualisation identifying functional features and structural features in the provided CT image.

The visualisation may comprise, for example, a simulated PET scan image, a simulated PET-CT image, a simulated SUV map or simulated inverted SUV map.

The method may further comprise sampling, from the simulated functional image dataset, radiomic feature values for a set of radiomic features. The method may further comprise providing the radiomic feature values to a classification model, for example a regression model, to output a predicted clinical outcome for the subject.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention.

Accordingly, embodiments provide a program comprising code for implementing a system or method as described herein and a machine-readable storage storing such a program. Still further, embodiments of the present invention may be conveyed electronically via any medium such as a communication signal carried over a wired or wireless connection and embodiments suitably encompass the same.

Many variations of the methods described herein will be apparent to the skilled person.

For example, subject may be understood to mean a human or animal or other suitable organism having blood vessels, or a sample therefrom.

While in the above discussion the primary example of a functional image dataset has been a PET scan image, and in particular an FDG-PET scan image, the skilled person would appreciate that other image data showing functional activity may also be used, such as SPECT scan data.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

---

The invention claimed is:

1. A method for identifying one or more functional features in a computed tomography (CT) image, the method comprising:

providing the CT image to a trained generator model, the generator model trained to translate an input CT image showing a target region of a subject to a positron emission tomography (PET) scan image indicating one or more functional features in the target region represented in the input CT image, wherein the generator model has been trained on a plurality of CT images and feedback from a discriminator;

outputting, from the trained generator model, a PET scan image corresponding to the provided CT image, the PET scan image indicating one or more functional features in a target region represented in the provided CT image.

2. A method according to claim 1, wherein the CT image is a non-contrast CT (NCT) image.

3. A method according to claim 1, wherein the CT image is a contrast CT (CCT) image.

4. A method according to claim 1, wherein the PET scan image further indicates structural features in the target region.

5. A method according to claim 1, wherein the PET scan image comprises a visualisation indicating the one or more functional features in the target region represented in the CT image.

6. A method according to claim 1, wherein the trained generator model has been trained using a generative adversarial network.

7. A method according to claim 1, wherein the trained generator model comprises a trained image segmentation model.

8. A method according to claim 1, wherein the one or more functional features comprise one or more tumours, and wherein the method further comprises:

sampling, from the PET scan image, radiomic feature values for a set of radiomic features;

providing the radiomic feature values to a trained classification model, the classification model trained to take as input a set of radiomic feature values and to output a classification indicating a predicted clinical outcome for the subject having the one or more tumours.

9. A method according to claim 8, wherein the classification model comprises a regression model or a random forest.

10. A method according to claim 8, wherein the predicted clinical outcome comprises locoregional tumour recurrence, distant metastasis, or death.

11. A non-transitory computer-readable medium having stored thereon:

computer-readable code representative of a trained generator model or classification model; and instructions which, when executed by one or more processors, cause the one or more processors to implement a method according to claim 1 to identify one or more functional features in a computed tomography (CT) image.

12. A computing apparatus for identifying functional features in a computed tomography (CT) image, the apparatus comprising:

one or more memory units; and one or more processors configured to execute instructions stored in the one or more memory units to perform the method of claim 1.

13. A method for training a generative adversarial network (GAN) to generate a simulated functional image dataset from a computed tomography (CT) image, the GAN comprising a generator network and a discriminator network, the method comprising:

receiving a training set comprising:

a plurality of CT images, each CT image showing a target region of a subject; and a plurality of functional image datasets, each functional image dataset indicating functional features in a target region of a subject;

training the GAN, wherein training the GAN comprises:

training the generator network, using the plurality of CT images and feedback from the discriminator network, to generate simulated functional image datasets;

training the discriminator network, using the generated simulated functional image datasets and the plurality of functional image datasets, to classify received image datasets as simulated functional image datasets or genuine functional image datasets, and to provide feedback to the generator network; and outputting a trained generator model to translate an input CT image to a simulated functional image dataset indicating one or more functional features in the target region shown in the input CT image.

14. A method according to claim 13, wherein the GAN is a cycle-GAN.

15. A method according to claim 13, wherein the plurality of functional image datasets comprises a plurality of PET scan images, PET-CT scan images, or SUV images, and wherein the trained generator model is to translate an input CT image to a simulated PET scan image, PET-CT scan image, or SUV image.

16. A non-transitory computer-readable medium having instructions stored thereon which, when executed by one or more processors, cause the one or more processors to implement a method for training a GAN, for training a machine learning image segmentation algorithm, or for training a machine learning classification algorithm, according to claim 13.

17. A computing apparatus for training a GAN, for training a machine learning image segmentation algorithm, or for training a machine learning classification algorithm, the apparatus comprising:

one or more memory units; and one or more processors configured to execute instructions stored in the one or more memory units to perform the method of any of claim 13.

18. A method according to claim 1, wherein the one or more functional features in a target region indicate infected, inflamed or cancerous tissue.

19. A method according to claim 13, wherein the one or more functional features in a target region indicate infected, inflamed or cancerous tissue.

* * * * *